United States Patent
Ralston et al.

(10) Patent No.: US 11,737,665 B2
(45) Date of Patent: Aug. 29, 2023

(54) MULTI-MODAL EYE IMAGING WITH SHARED OPTICAL PATH

(71) Applicant: Tesseract Health, Inc., Guilford, CT (US)

(72) Inventors: Tyler S. Ralston, Clinton, CT (US); Maurizio Arienzo, New York, NY (US); Owen Kaye-Kauderer, Brooklyn, NY (US); Benjamin Rosenbluth, Hamden, CT (US); Jonathan M. Rothberg, Guilford, CT (US); Lawrence C. West, San Jose, CA (US); Paul E. Glenn, Wellesley, MA (US)

(73) Assignee: Tesseract Health, Inc., Guilford, CT (US)

( * ) Notice: Subject to any disclaimer, the term of this patent is extended or adjusted under 35 U.S.C. 154(b) by 358 days.

(21) Appl. No.: 16/907,039

(22) Filed: Jun. 19, 2020

(65) Prior Publication Data

US 2020/0397286 A1    Dec. 24, 2020

Related U.S. Application Data

(60) Provisional application No. 62/936,250, filed on Nov. 15, 2019, provisional application No. 62/865,065, filed on Jun. 21, 2019.

(51) Int. Cl.
*A61B 3/00* (2006.01)
*A61B 3/12* (2006.01)
(Continued)

(52) U.S. Cl.
CPC .............. *A61B 3/12* (2013.01); *A61B 3/0008* (2013.01); *A61B 3/102* (2013.01); *A61B 3/1176* (2013.01); *A61B 3/14* (2013.01)

(58) Field of Classification Search
CPC ......... A61B 3/12; A61B 3/0008; A61B 3/102; A61B 3/1176; A61B 3/14; A61B 3/10
See application file for complete search history.

(56) References Cited

U.S. PATENT DOCUMENTS

| 4,762,701 A | 8/1988 | Horan et al. |
| 5,973,731 A | 10/1999 | Schwab |

(Continued)

FOREIGN PATENT DOCUMENTS

| JP | 2003-085662 A | 3/2003 |
| JP | 2008-005987 A | 1/2008 |

(Continued)

OTHER PUBLICATIONS

PCT/US2020/038817, filed Sep. 15, 2020, Invitation to Pay Additional Fees.

(Continued)

*Primary Examiner* — Mustak Choudhury
(74) *Attorney, Agent, or Firm* — Wolf, Greenfield & Sacks, P.C.

(57) ABSTRACT

Aspects of the present disclosure provide improved techniques for imaging a subject's retina fundus. Some aspects relate to an imaging apparatus that may be substantially binocular shaped and/or may house multiple imaging devices configured to provide multiple corresponding modes of imaging the subject's retina fundus. Some aspects relate to techniques for imaging a subject's eye using white light, fluorescence, infrared (IR), optical coherence tomography (OCT), and/or other imaging modalities that may be employed by a single imaging apparatus. Some aspects relate to improvements in white light, fluorescence, IR, OCT, and/or other imaging technologies that may be employed alone or in combination with other techniques. Some aspects relate to multi-modal imaging techniques that enable determination of a subject's health status. Imaging (Continued)

apparatuses and techniques described herein provide medical grade retina fundus images and may be produced or conducted at low cost, thus increasing access to medical grade imaging.

29 Claims, 42 Drawing Sheets

(51) Int. Cl.
| | | |
|---|---|---|
| *A61B 3/14* | (2006.01) | |
| *A61B 3/117* | (2006.01) | |
| *A61B 3/10* | (2006.01) | |

(56) References Cited

U.S. PATENT DOCUMENTS

| | | | |
|---|---|---|---|
| 6,022,109 | A | 2/2000 | Dal Santo |
| 6,546,198 | B2 | 4/2003 | Ohtsuka |
| 7,555,148 | B1 | 6/2009 | Steinberg et al. |
| 8,184,867 | B2 | 5/2012 | Otto et al. |
| 9,041,347 | B2 | 5/2015 | Paschke et al. |
| 9,710,016 | B1 | 7/2017 | Porzio |
| 9,808,154 | B2 | 11/2017 | Cleland et al. |
| 10,653,311 | B1 | 5/2020 | Pascal et al. |
| 2002/0052551 | A1 | 5/2002 | Sinclair et al. |
| 2005/0159662 | A1 | 7/2005 | Imanishi et al. |
| 2006/0203194 | A1 | 9/2006 | Suzuki |
| 2006/0244913 | A1 | 11/2006 | Gellerman |
| 2008/0212847 | A1 | 9/2008 | Davies et al. |
| 2009/0147217 | A1 | 6/2009 | Molnar et al. |
| 2010/0110377 | A1 | 5/2010 | Maloca |
| 2010/0146308 | A1 | 6/2010 | Gioscia et al. |
| 2010/0183199 | A1 | 7/2010 | Smith et al. |
| 2010/0309303 | A1 | 12/2010 | Sanchez Ramos et al. |
| 2010/0315041 | A1 | 12/2010 | Tan |
| 2011/0043756 | A1* | 2/2011 | Kahn ............... G01N 21/55 351/206 |
| 2011/0282331 | A1* | 11/2011 | Brennan ........... G01N 21/4795 606/4 |
| 2012/0092619 | A1 | 4/2012 | Rowe |
| 2014/0146288 | A1 | 5/2014 | Anand et al. |
| 2014/0276025 | A1 | 9/2014 | Durbin et al. |
| 2015/0157505 | A1 | 6/2015 | Neev |
| 2015/0265172 | A1 | 9/2015 | Fuller et al. |
| 2015/0288687 | A1 | 10/2015 | Heshmati et al. |
| 2015/0374232 | A1* | 12/2015 | Yoshino ............. A61B 3/12 351/206 |
| 2016/0143523 | A1 | 5/2016 | Miyashita et al. |
| 2016/0270656 | A1 | 9/2016 | Samec et al. |
| 2016/0320837 | A1 | 11/2016 | Swedish et al. |
| 2017/0007843 | A1 | 1/2017 | Samec et al. |
| 2017/0079522 | A1 | 3/2017 | Artsyukhovich et al. |
| 2017/0196496 | A1 | 7/2017 | Goldstein et al. |
| 2018/0018451 | A1 | 1/2018 | Spizhevoy et al. |
| 2018/0028691 | A1 | 2/2018 | Feuerstein et al. |
| 2018/0140180 | A1 | 5/2018 | Coleman |
| 2018/0148505 | A1* | 5/2018 | Cadavid ............. A61P 43/00 |
| 2018/0235467 | A1 | 8/2018 | Celenk et al. |
| 2018/0280196 | A1 | 10/2018 | Luttrull et al. |
| 2018/0317832 | A1 | 11/2018 | Scott |
| 2018/0320145 | A1 | 11/2018 | Chalberg et al. |
| 2018/0330162 | A1 | 11/2018 | Hanna |
| 2019/0117318 | A1 | 4/2019 | Charron |
| 2019/0206054 | A1 | 7/2019 | Mao |
| 2019/0261853 | A1 | 8/2019 | Williamson |
| 2020/0191553 | A1 | 6/2020 | Rothberg et al. |
| 2020/0397285 | A1 | 12/2020 | Ralston et al. |
| 2020/0397290 | A1 | 12/2020 | Ralston et al. |
| 2021/0127969 | A1 | 5/2021 | Oggenfuss et al. |
| 2021/0145276 | A1 | 5/2021 | Yao et al. |

FOREIGN PATENT DOCUMENTS

| | | |
|---|---|---|
| JP | 4527471 B2 | 8/2010 |
| RU | 2611202 C2 | 2/2017 |
| WO | WO 2015/188142 A1 | 12/2015 |
| WO | WO 2017/030770 A1 | 2/2017 |
| WO | WO 2018/112254 A1 | 6/2018 |
| WO | WO 2018/213492 A1 | 11/2018 |

OTHER PUBLICATIONS

PCT/US2020/038817, filed Nov. 10, 2020, International Search Report and Written Opinion.
International Preliminary Report on Patentability for International Application No. PCT/US2019/066067 dated Jun. 24, 2021.
Dehoog et al., Optimal parameters for retinal illumination and imaging in fundus cameras. Optical Society of America. Dec. 20, 2008; 47(36): 6769-77.
International Search Report and Written Opinion for International Application No. PCT/US2019/066062 dated Apr. 8, 2020.
International Search Report and Written Opinion for International Application No. PCT/US2019/066067 dated Apr. 8, 2020.
International Search Report and Written Opinion for International Application No. PCT/US2019/066069 dated Apr. 24, 2020.
International Search Report and Written Opinion for International Application No. PCT/US2019/066073 dated Apr. 28, 2020.
Invitation to Pay Additional Fees for International Application No. PCT/US2019/066062 dated Feb. 13, 2020.
Invitation to Pay Additional Fees for International Application No. PCT/US2019/066067 dated Feb. 12, 2020.
Invitation to Pay Additional Fees for International Application No. PCT/US2019/066069 dated Feb. 13, 2020.
Invitation to Pay Additional Fees for International Application No. PCT/US2019/066073 dated Feb. 14, 2020.
[No Author Listed], Optomap af Diagnostic Atlas. A Retinal Reference Guide. Optos Building The Retina Company. 2016. 37 pages.
Fukuta et al., Personal Identification Based on Blood Vessels of Retinal Fundus Images. Proc of SPIE. 2008;6914:69141V. 9 pages, doi: 10.1117/12.769330.
Lahiri et al., Retinal Vessel Segmentation under Extreme Low Annotation: A Generative Adversarial Network Approach. arXiv:1809. 01348v1. Sep. 5, 2018. 9 pages.
Mazumdar et al., Retina Based Biometric Authentication System: A Review. International Journal of Advanced Research in Computer Science. 2018;9(1):711-718. DOI:http://dx.doi.org/10.26483/ijarcs. v9i1.5322.
Son et al., Retinal Vessel Segmentation in Fundoscopic Images with Generative Adversarial Networks. arXiv:1706.09318v1. Jun. 28, 2017. 9 pages.
U.S. Appl. No. 16/712,831, filed Dec. 12, 2019, Rothberg et al.
U.S. Appl. No. 16/906,763, filed Jun. 19, 2020, Ralston et al.
U.S. Appl. No. 16/906,615, filed Jun. 19, 2020, Ralston et al.
PCT/US2019/066062, Apr. 8, 2020, International Search Report and Written Opinion.
PCT/US2019/066062, Feb. 13, 2020, Invitation to Pay Additional Fees
PCT/US2019/066067, Apr. 8, 2020, International Search Report and Written Opinion.
PCT/US2019/066067, Feb. 12, 2020, Invitation to Pay Additional Fees.
PCT/US2019/066069, Apr. 24, 2020, International Search Report and Written Opinion.
PCT/US2019/066069, Feb. 13, 2020, Invitation to Pay Additional Fees.
PCT/US2019/066073, Apr. 28, 2020, International Search Report and Written Opinion.
PCT/US2019/066073, Feb. 14, 2020, Invitation to Pay Additional Fees.
Invitation to Pay Additional Fees for International Application No. PCT/US2020/038817, dated Sep. 15, 2020.
International Search Report and Written Opinion for International Application No. PCT/US2020/038817, dated Nov. 10, 2020.
International Preliminary Report on Patentability dated Dec. 30,

(56) References Cited

OTHER PUBLICATIONS 2021, in connection with International Application No. PCT/US2020/038817.

Extended European Search Report dated Oct. 5, 2022, in connection with European Application No. 19897369.5.

Dysli et al. Fluorescence lifetime imaging ophthalmoscopy. Progress in Retinal and Eye Research. 2017;60:120-143.

Suhling et al. Fluorescence lifetime imaging (FLIM): Basic Concepts and Some recent developments. Medical Phonics. Mar. 2015;27:3-40.

* cited by examiner

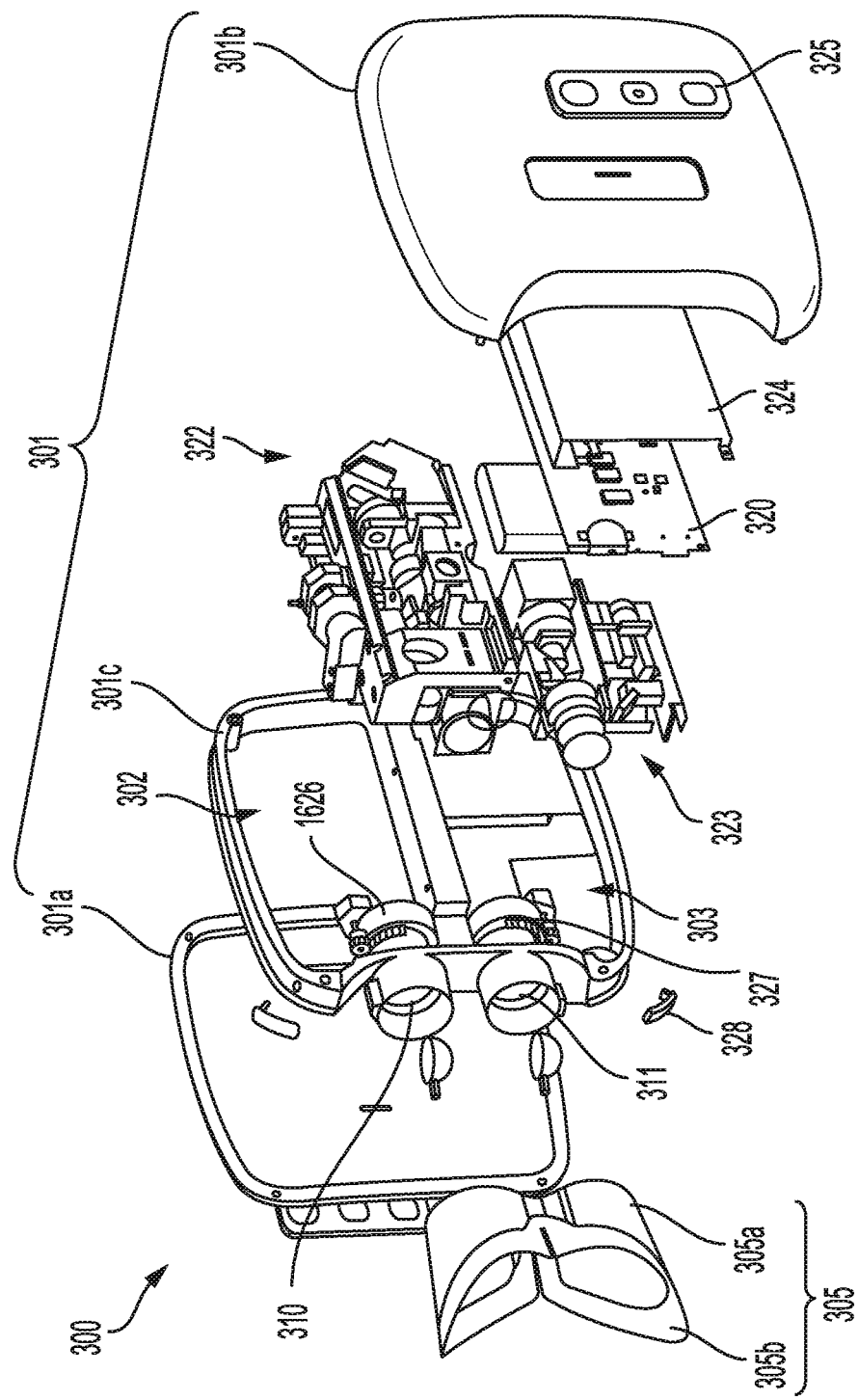

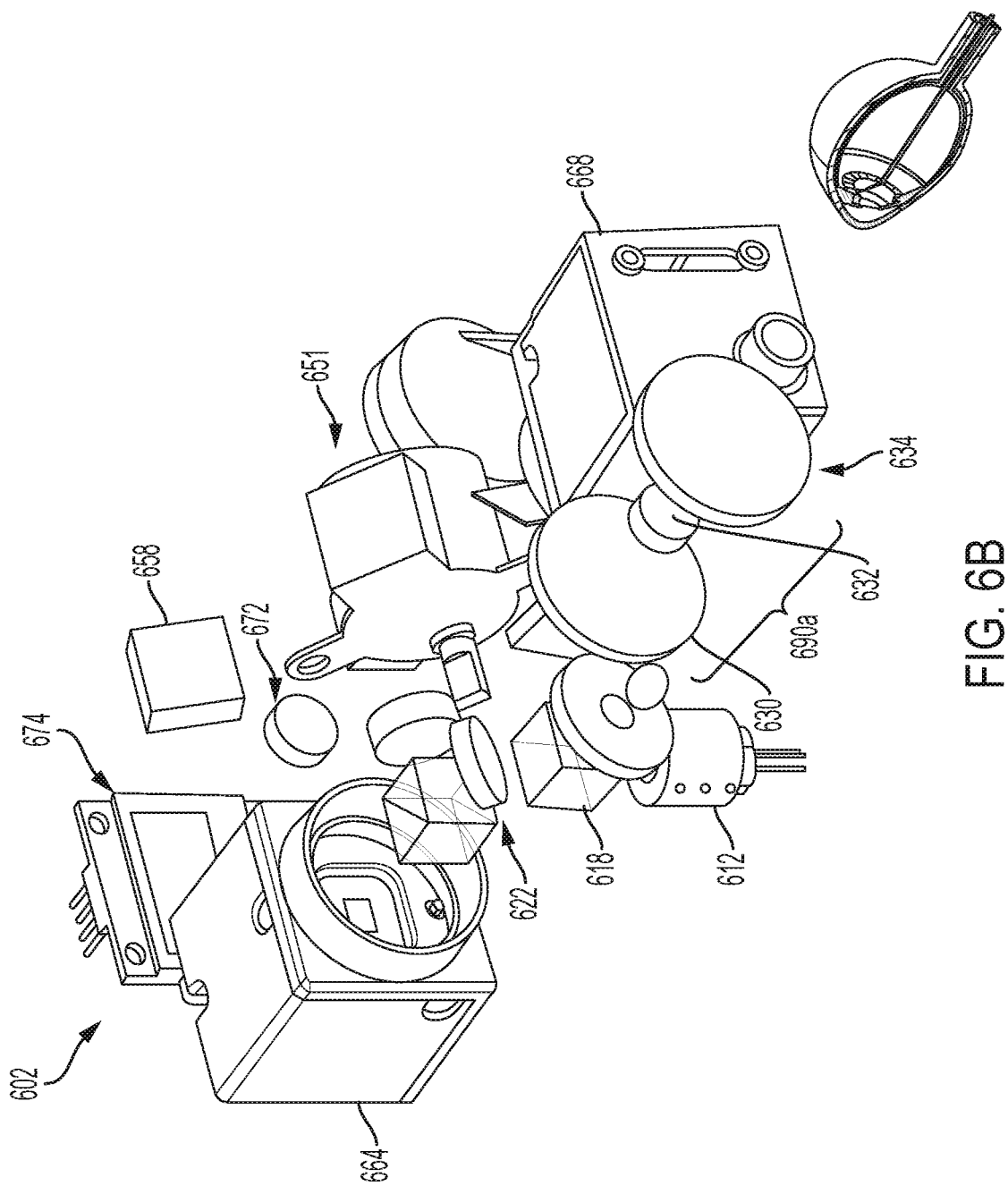

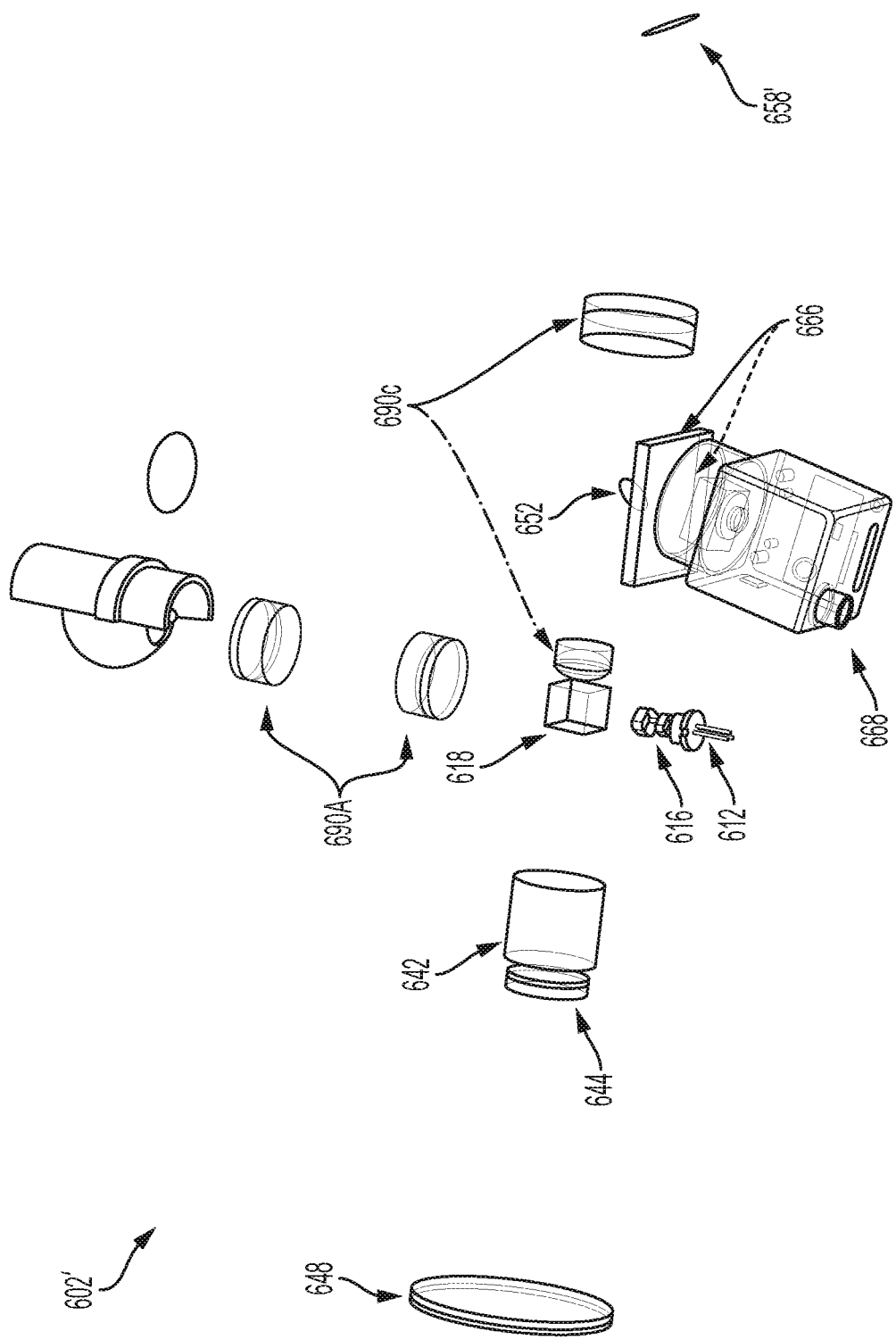

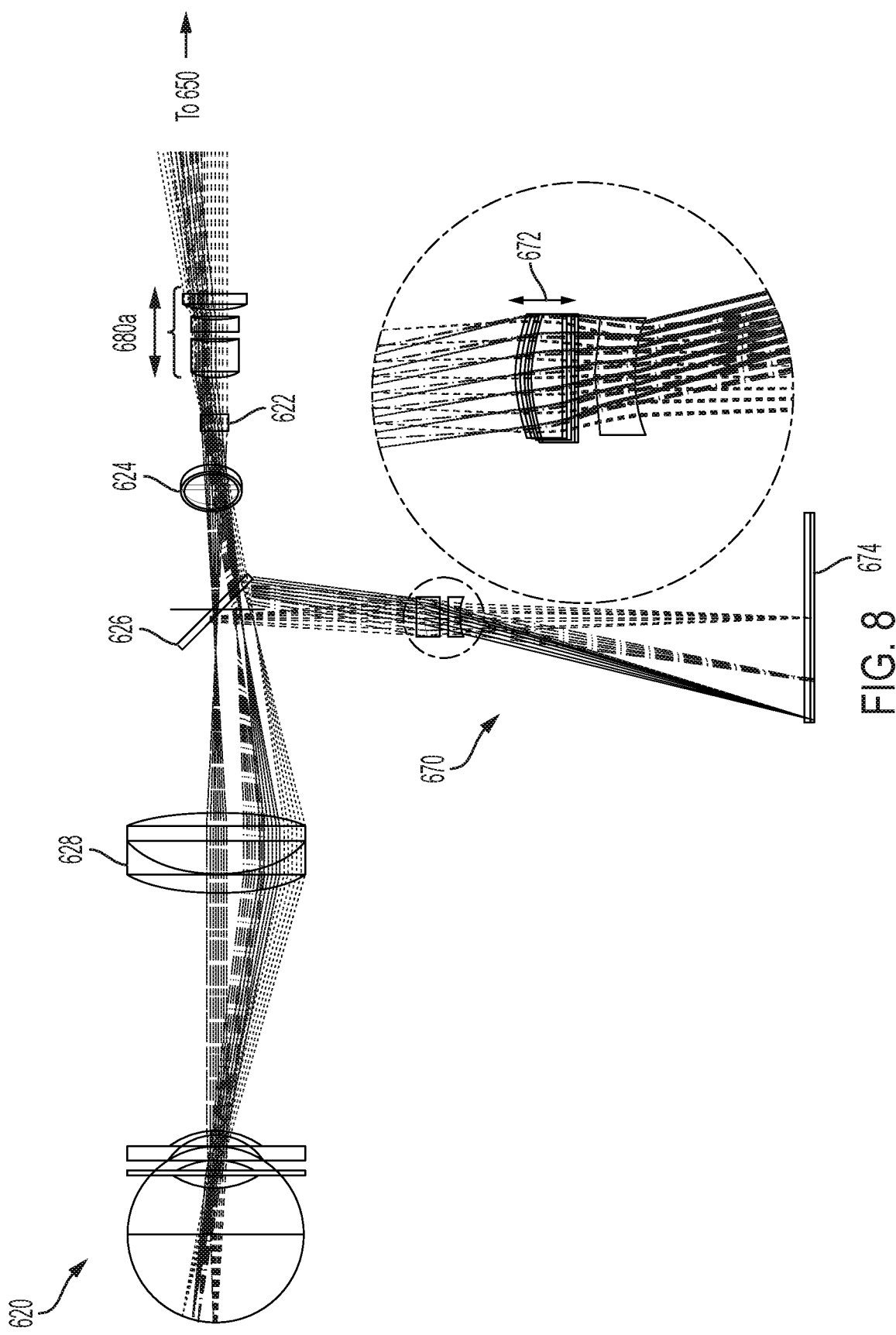

MULTI-MODAL EYE IMAGING WITH SHARED OPTICAL PATH

CROSS REFERENCE TO RELATED APPLICATIONS

This application claims priority under 35 U.S.C. § 119(e) to U.S. Provisional Application Ser. No. 62/936,250, filed Nov. 15, 2019, and entitled, "FLUORESCENCE LIFETIME AND/OR OPTICAL IMAGING AND/OR MEASUREMENT OF THE FUNDUS," and U.S. Provisional Application Ser. No. 62/865,065, filed Jun. 21, 2019, and entitled, "MULTIMODAL FUNDUS IMAGING," each application of which is hereby incorporated by reference in its entirety.

BACKGROUND

The retinal fundus of an eye may be conventionally imaged using a conventional digital camera. Present techniques for imaging the retina fundus would benefit from improvement.

SUMMARY

Some aspects of the present disclosure relate to an apparatus for imaging and/or measuring a retina fundus of a subject, the apparatus comprising a housing, a white light imaging device supported by the housing, and a fluorescence imaging device supported by the housing, wherein the white light imaging device and the fluorescence imaging device share at least a portion of a shared optical path within the housing.

In some embodiments, the white light imaging device and the fluorescence imaging device share an imaging sensor.

In some embodiments, the white light imaging device comprises a white light source, the fluorescence imaging device comprises at least one laser, and the apparatus further comprises an optical element configured to combine an optical path of light emitted from the white light source with an optical path of light emitted from the at least one laser such that the light emitted from the white light source and the light emitted from the at least one laser share the shared optical path.

In some embodiments, the fluorescent imaging device comprises a first laser configured to emit light at a first wavelength and a second laser configured to emit light at a second wavelength and the apparatus comprises a first optical element configured to combine the optical path of light emitted from the white light source with an optical path of light emitted from the first laser and a second optical element configured to combine the optical path of the light emitted from the white light source and the optical path of the light emitted from the first laser with an optical path of light emitted from the second laser, such that the light emitted from the white light source, the light emitted from the first laser, and the light emitted from the second laser share the shared optical path.

In some embodiments, the shared optical path includes a path from the first optical element to an eye of the subject, and from the eye of the subject to the imaging sensor.

In some embodiments,, the apparatus further comprises a reflector in the shared optical path, the reflector comprising an opening configured to allow light reflected from the retina fundus to pass through the reflector.

In some embodiments, the apparatus further comprises a beam splitter configured to transmit light for the fluorescence imaging device to a fluorescence imaging sensor and reflect light for the white light imaging device to a white light image sensor.

In some embodiments, a transmissivity of the beam splitter is greater than a reflectivity of the beam splitter.

In some embodiments, the fluorescence imaging sensor is configured to detect a fluorescence lifetime of at least one molecule in the subject's eye.

In some embodiments, the fluorescence imaging sensor is configured to detect a fluorescence wavelength of at least one molecule in the subject's eye.

Some aspects of the present disclosure relate to a method comprising imaging a retina fundus of a subject with a white light imaging device and a fluorescence imaging device which share, at least in part, an optical path.

Some aspects of the present disclosure relate to a method comprising imaging and/or measuring the retina fundus of a subject using an apparatus comprising at least two imaging and/or measuring devices selected from a group comprising a white light imaging device, a fluorescence imaging device, and an optical coherence tomography device, and determining a medical status of the subject based on an image captured during imaging and/or measuring;.

In some embodiments, determining the medical status comprises determining whether the subject suffers from an ocular disease.

In some embodiments, wherein the ocular disease comprises age-related macular degeneration (AMD).

In some embodiments, the ocular disease comprises Stargardt's disease.

In some embodiments, the ocular disease comprises diabetic retinopathy.

In some embodiments, the ocular disease comprises macular edema.

In some embodiments, the ocular disease comprises a macular hole.

In some embodiments, the ocular disease comprises eye floaters.

In some embodiments, the ocular disease comprises glaucoma.

In some embodiments, the ocular disease comprises retinal detachment.

In some embodiments, the ocular disease comprises cataracts.

In some embodiments, the ocular disease comprises macular telangiectasia.

In some embodiments, determining the medical status comprises determining whether the subject suffers from a non-ocular disease.

In some embodiments, the non-ocular disease comprises Alzheimer's.

In some embodiments, determining whether the subject suffers from Alzheimer's comprises determining a thickness of a retinal nerve fiber layer of the subject using the image.

In some embodiments, the non-ocular disease comprises Parkinson's.

In some embodiments, determining whether the subject suffers from Parkinson's comprises determining a thickness of a retinal nerve fiber layer of the subject using the image.

In some embodiments, determining whether the subject suffers from Parkinson's comprises determining a measure of eye-tracking capability using the image.

In some embodiments, the non-ocular disease comprises a concussion.

The foregoing summary is not intended to be limiting. Moreover, various aspects of the present disclosure may be implemented alone or in combination.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIG. 3B is an exploded view of the multimodal imaging apparatus of FIG. 3A, according to some embodiments.

FIG. 6B is a side perspective view of components of the OCT and IR imaging device of FIG. 6A, according to some embodiments.

FIG. 6C is an exploded view of alternative components that may be included in the OCT and IR imaging device of FIGS. 6A-6B, according to some embodiments.

FIG. 8 is a top view of sample and fixation components of the OCT and IR imaging device of FIGS. 6A-7A, according to some embodiments.

DETAILED DESCRIPTION

Figure 1A:
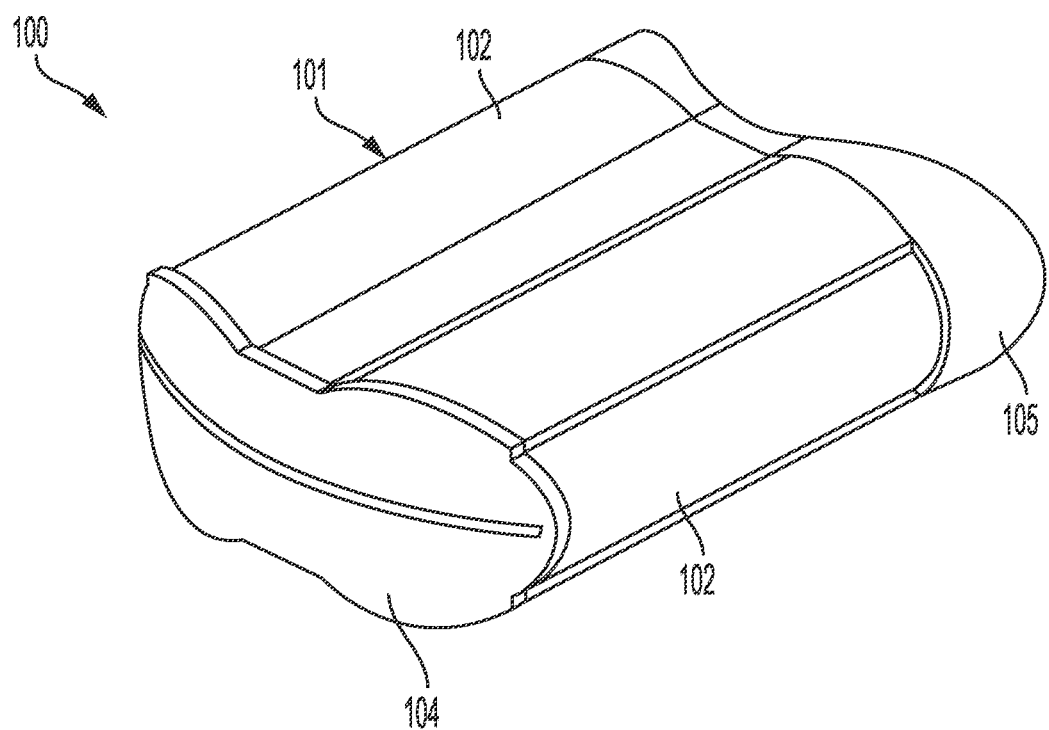
FIG. 1A is a front perspective view of a multimodal imaging apparatus, according to some embodiments.

Aspects of the present disclosure provide improved techniques for imaging a subject's retina fundus. Some aspects relate to an imaging apparatus that may be substantially binocular shaped and/or may house multiple imaging devices configured to provide multiple corresponding modes of imaging the subject's retina fundus. Some aspects relate to techniques for imaging a subject's eye using white light, fluorescence, infrared (IR), optical coherence tomography (OCT), and/or other imaging modalities that may be employed by a single imaging apparatus. Some aspects relate to improvements in white light, fluorescence, IR, OCT, and/or other imaging technologies that may be employed alone or in combination with other techniques. Some aspects relate to multi-modal imaging techniques that enable determination of a subject's health status. Imaging apparatuses and techniques described herein provide medical grade imaging quality and may be produced or conducted at low cost, thus increasing access to medical grade imaging.

The inventors have recognized and appreciated that a person's eyes provide a window into the body that may be used to not only to determine whether the person has an ocular disease, but to determine the general health of the person. However, conventional systems of imaging the fundus only provide superficial information about the subject's eye and cannot provide sufficient information to diagnose certain diseases. Accordingly, in some embodiments, multiple modes of imaging are used to more fully image the fundus of a subject. For example, two or more techniques may be used to simultaneously image the fundus. In some embodiments, the techniques of optical imaging, fluorescent imaging, and optical coherence tomography may be used to provide multimodal imaging of the fundus. The inventors have recognized that by using multimodal imaging, as compared to conventional two-dimensional imaging, a greater amount of information may be obtained about the fundus than that may be used to determine the health of the subject. In some embodiments, two or more of two-dimensional optical imaging, optical coherence tomography (OCT), fluorescent spectral imaging, and fluorescent lifetime imaging (FLIM) may be used to provide multidimensional images of the fundus. By way of example, a device that jointly uses two-dimensional optical imaging, optical coherence tomography (OCT), fluorescent spectral imaging, and fluorescent lifetime imaging (FLIM) provides five-dimensional imaging of the fundus.

The inventors have recognized and appreciated that the limits of conventional two-dimensional optical imaging of the fundus may be overcome by providing one or more of the aforementioned additional modes of imaging. For example, OCT provides information about characteristics of the fundus that lie below the surface of the fundus. This information is not accessible by conventional imaging techniques. Similarly, fluorescent imaging (using spectral and/or lifetime discrimination) provides information about the molecular consistency of the fundus and/or the presence or absence of biomarkers (if being used) that are not possible to distinguish using conventional optical imaging or OCT.

The inventors have recognized and appreciated that these extra dimensions of information contain additional information that may be used by a specialist and/or machine learning techniques to diagnose a wide range of diseases that are not limited to ocular health, but include the general health of the subject. Accordingly, some embodiments are directed to a real-time universal diagnostic apparatus that is capable of determining, for example, ophthalmological health, vitals, presence of an infection, cardiovascular health, inflammation, and/or neurological health, as well as the health status of an individual including a person's propensity to contract certain health conditions. By way of example, 34% of cardiovascular disease can be effectively treated by identifying at risk patients at an early stage. Childhood blindness can be diagnosed and prevented by screening premature babies for glaucoma and other ocular diseases. The inventors have recognized that diagnostic tools, such as the apparatus described in some embodiments, provide non-invasive techniques for determining whether a subject has a condition or is predisposed to such a condition.

The inventors have further recognized and appreciated that making the device portable, handheld, and affordable would have the greatest impact on global health. Countries or regions that cannot afford specialized facilities for diagnosing certain diseases and/or do not have the medical specialists to analyze data from imaging tests are often left behind to the detriment of the overall health of the population. A portable device that may be brought to any low-income community allowing greater access to important healthcare diagnostics. Accordingly, some embodiments are directed to an apparatus that includes multiple modes of imaging the fundus within a housing that is portable and, in some examples, handheld. In some embodiments, the apparatus has a binocular form factor such that a subject may hold the apparatus up to the eyes for fundus imaging. In some embodiments, one or more of the modes of imaging may share optical components to make the apparatus more compact, efficient, and cost effective. For example, an optical imaging device and the fluorescent imaging device may be housed in a first half of the binocular housing of the apparatus and the OCT device may be housed in the second half of the binocular housing. Using such an apparatus, both eyes of the subject may be imaged simultaneously using the different devices. For example, the subject's left eye may be imaged using the optical imaging device and/or the fluorescent imaging device while the subject's right eye is imaged using the OCT device. After the initial imaging is complete, the subject can reverse the orientation of the binocular apparatus such that each eye is then measured with the devices disposed in the other half of the binocular housing, e.g., the left eye is imaged using the OCT device and the right eye is imaged using the optical imaging device and/or the fluorescent imaging device. To ensure the apparatus can operate in both orientations, the front surface of the apparatus that is placed near the subject's eyes may be substantially symmetric. Additionally or alternatively, the two halves of the apparatus's housing may be connected by a hinge that allows the two halves to be adjusted to be either orientation.

The inventors have further recognized and appreciated that providing the apparatus with an interface to a deep learning system to enable the system to learn and become smarter, allows ease of use by non-professionals. In low-income communities, access to specialists that are able to operate complex apparatuses and/or analyze the resulting images acquired by such equipment is limited. In addition, the apparatus may communicate in either direction with a smart device (e.g., cellular telephone or tablet) and/or cloud based storage device, such that the apparatus can be controlled by, and/or upload images to, the smart device and/or cloud. By providing an apparatus that interfaces with a deep learning system, the multimodal images acquired by the apparatus of some embodiments may be automatically analyzed to determine one more health indicators of the subject without the need of a specialist at the point of care.

I. Multi-Modal Imaging Apparatus

The inventors have developed novel and improved imaging apparatuses having enhanced imaging functionality and a versatile form factor. In some embodiments, imaging apparatuses described herein may include multiple imaging devices, such as at least two members selected from OCT, IR, white light, and/or FLIM devices within a common housing. For example, a single imaging apparatus may include a housing shaped to support various imaging devices (white light, IR, fluorescence, and/or OCT, etc.) within the housing. In some embodiments, the different imaging devices may be divided between two sides of the housing, where imaging devices on each side of the housing are configured to image one of the subject's eyes. In some embodiments, all of the imaging devices may be configured to image a same one of the subject's eyes. In some embodiments, a single multi-modal imaging device positioned in portion of the housing may be configured to support multiple modes of imaging (e.g., IR and OCT, white light and FLIM, etc.). In some embodiments, the housing may further include electronics for performing imaging, processing or pre-processing images, and/or accessing the cloud for image storage and/or transmission. In some embodiments, electronics onboard the imaging apparatus may be configured to determine a health status or medical condition of the user.

In some embodiments, imaging apparatus described herein may have a form factor that is conducive to imaging both of a person's eyes (e.g., simultaneously). In some embodiments, imaging apparatus described herein may be configured for imaging each eye with a different imaging device of the imaging apparatus. For example, as described further below, the imaging apparatus may include a pair of lenses held in a housing of the imaging apparatus for aligning with a person's eyes, and the pair of lenses may also be aligned with respective imaging devices of the imaging apparatus. In some embodiments, the imaging apparatus may include a substantially binocular shaped form factor with an imaging device positioned on each side of the imaging apparatus. During operation of the imaging apparatus, a person may simply flip the vertical orientation of the imaging apparatus (e.g., by rotating the device about an axis parallel to the direction in which imaging is performed). Accordingly, the imaging apparatus may transition from imaging the person's right eye with a first imaging device to imaging the right eye with a second imaging device, and likewise, transition from imaging the person's left eye with the second imaging device to imaging the left eye with the first imaging device. In some embodiments, imaging apparatus described herein may be configured for mounting on a table or desk, such as on a stand. For example, the stand may permit rotation of the imaging apparatus about one or more axes to facilitate rotation by a user during operation.

It should be appreciated that aspects of the imaging apparatus described herein may be implemented using a different form factor than substantially binocular shaped. For instance, embodiments having a form factor different than substantially binocular shaped may be otherwise configured in the manner described herein in connection with the exemplary imaging apparatus described below. For example, such imaging apparatus may be configured to image one or both of a person's eyes simultaneously using one or more imaging devices of the imaging apparatus.

Figure 1B:
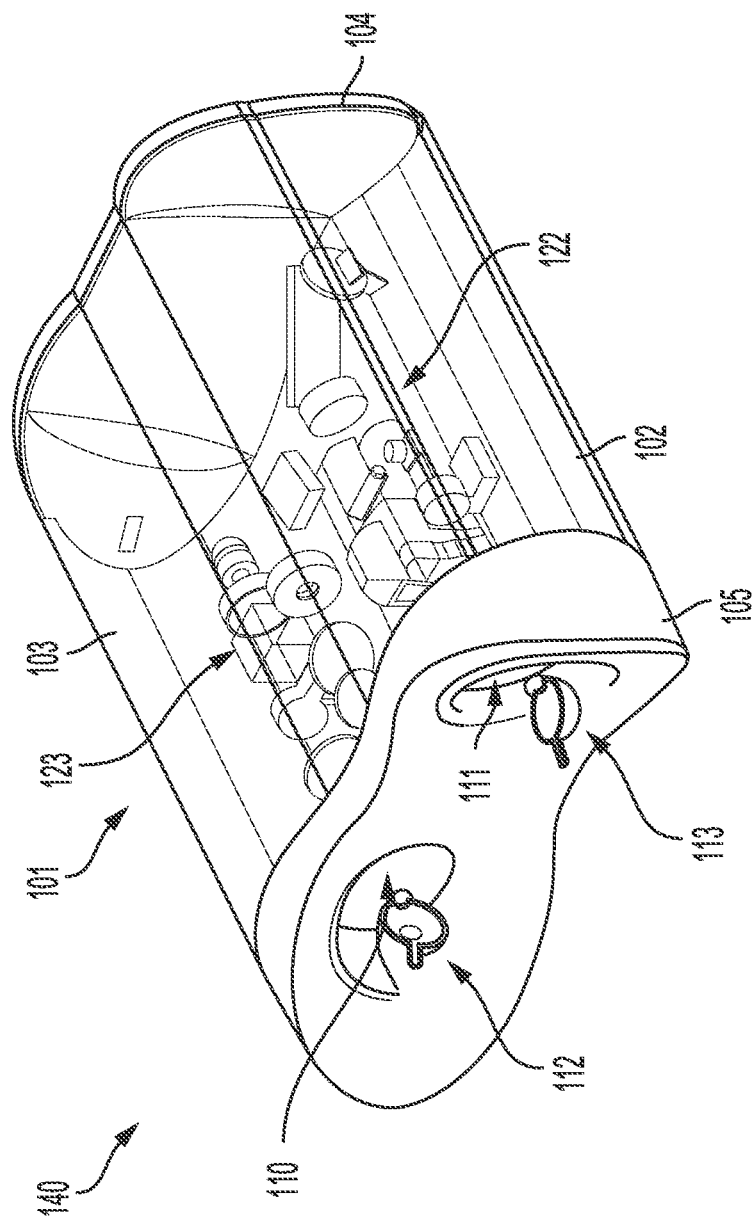
FIG. 1B is a rear perspective view of the multimodal imaging apparatus of FIG. 1B, according to some embodiments.

One example of an imaging apparatus according to the technology described herein is illustrated in FIGS. 1A-1B. As shown in FIG. 1A, imaging apparatus 100 includes a housing 101 with a first housing section 102 and a second housing section 103. In some embodiments, the first housing section 102 may accommodate a first imaging device 122 of the imaging apparatus 100, and the second housing section 103 may accommodate a second imaging device 123 of the imaging apparatus. As illustrated in FIGS. 1A-1B, housing 101 is substantially binocular shaped.

In some embodiments, the first and second imaging devices 122 and 123 may include an optical imaging device, a fluorescent imaging device, and/or an OCT imaging device. For example, in one embodiment, the first imaging device 122 may be an OCT imaging device, and the second imaging device 123 may be an optical and fluorescent imaging device. In some embodiments, the imaging apparatus 100 may include only a single imaging device 122 or 123, such as only an optical imaging device or only a fluorescent imaging device. In some embodiments, first and second imaging devices 122 and 123 may share one or more optical components such as lenses (e.g., convergent, divergent, etc.), mirrors, and/or other imaging components. For instance, in some embodiments, first and second imaging devices 122 and 123 may share a common optical path. It is envisioned that the devices may operate independently or in common. Each may be an OCT imaging device, each may be a fluorescent imaging device, or both may be one or the other. Both eyes may be imaged and/or measured simultaneously, or each eye may be imaged and/or measured separately.

Housing sections 102 and 103 may be connected to a front end of the housing 101 by a front housing section 105. In the illustrative embodiment, the front housing section 105 is shaped to accommodate the facial profile of a person, such as having a shape that conforms to a human face. When accommodating a person's face, the front housing section 105 may further provide sight-lines from the person's eyes to the imaging devices 122 and/or 123 of the imaging apparatus 100. For example, the front housing section 105 may include a first opening 110 and a second opening 111 that correspond with respective openings in the first housing section 102 and the second housing section 103 to provide minimally obstructed optical paths between the first and second optical devices 122 and 123 and the person's eyes.

In some embodiments, the openings 110 and 110 may be covered with one or more transparent windows (e.g., each having its own window, having a shared window, etc.), which may include glass or plastic.

First and second housing sections 102 and 103 may be connected at a rear end of the housing 101 by a rear housing section 104. The rear housing section 104 may be shaped to cover the end of the first and second housing sections 102 and 103 such that light in an environment of the imaging apparatus 100 does not enter the housing 101 and interfere with the imaging devices 122 or 123.

In some embodiments, imaging apparatus 100 may be configured for communicatively coupling to another device, such as a mobile phone, desktop, laptop, or tablet computer, and/or smart watch. For example, imaging apparatus 100 may be configured for establishing a wired and/or wireless connection to such devices, such as by USB and/or a suitable wireless network. In some embodiments, housing 101 may include one or more openings to accommodate one or more electrical (e.g., USB) cables. In some embodiments, housing 101 may have one or more antennas disposed thereon for transmitting and/or receiving wireless signals to or from such devices. In some embodiments, imaging devices 122 and/or 123 may be configured for interfacing with the electrical cables and/or antennas. In some embodiments, imaging devices 122 and/or 123 may receive power from the cables and/or antennas, such as for charging a rechargeable battery disposed within the housing 101.

During operation of the imaging apparatus 100, a person using the imaging apparatus 100 may place the front housing section 105 against the person's face such that the person's eyes are aligned with openings 110 and 111. In some embodiments, the imaging apparatus 100 may include a gripping member (not shown) coupled to the housing 101 and configured for gripping by a person's hand. In some embodiments, the gripping member may be formed using a soft plastic material, and may be ergonomically shaped to accommodate the person's fingers. For instance, the person may grasp the gripping member with both hands and place the front housing section 105 against the person's face such that the person's eyes are in alignment with openings 110 and 111. Alternatively or additionally, the imaging apparatus 100 may include a mounting member (not shown) coupled to the housing 101 and configured for mounting the imaging apparatus 100 to a mounting arm, such as for mounting the imaging apparatus 100 to a table or other equipment. For instance, when mounted using the mounting member, the imaging apparatus 100 may be stabilized in one position for use by a person without the person needing to hold the imaging apparatus 100 in place.

In some embodiments, the imaging apparatus 100 may employ a fixator, such as a visible light projection from the imaging apparatus 100 towards the person's eyes, such as along a direction in which the openings 110 and 111 are aligned with the person's eyes, for example. In accordance with various embodiments, the fixator may be a bright spot, such as a circular or elliptical spot, or an image, such as an image or a house or some other object. The inventors recognized that a person will typically move both eyes in a same direction to focus on an object even when only one eye perceives the object. Accordingly, in some embodiments, the image apparatus 100 may be configured to provide the fixator to only one eye, such as using only one opening 110 or 111. In other embodiments, fixators may be provided to both eyes, such as using both openings 110 and 111.

Figure 2:
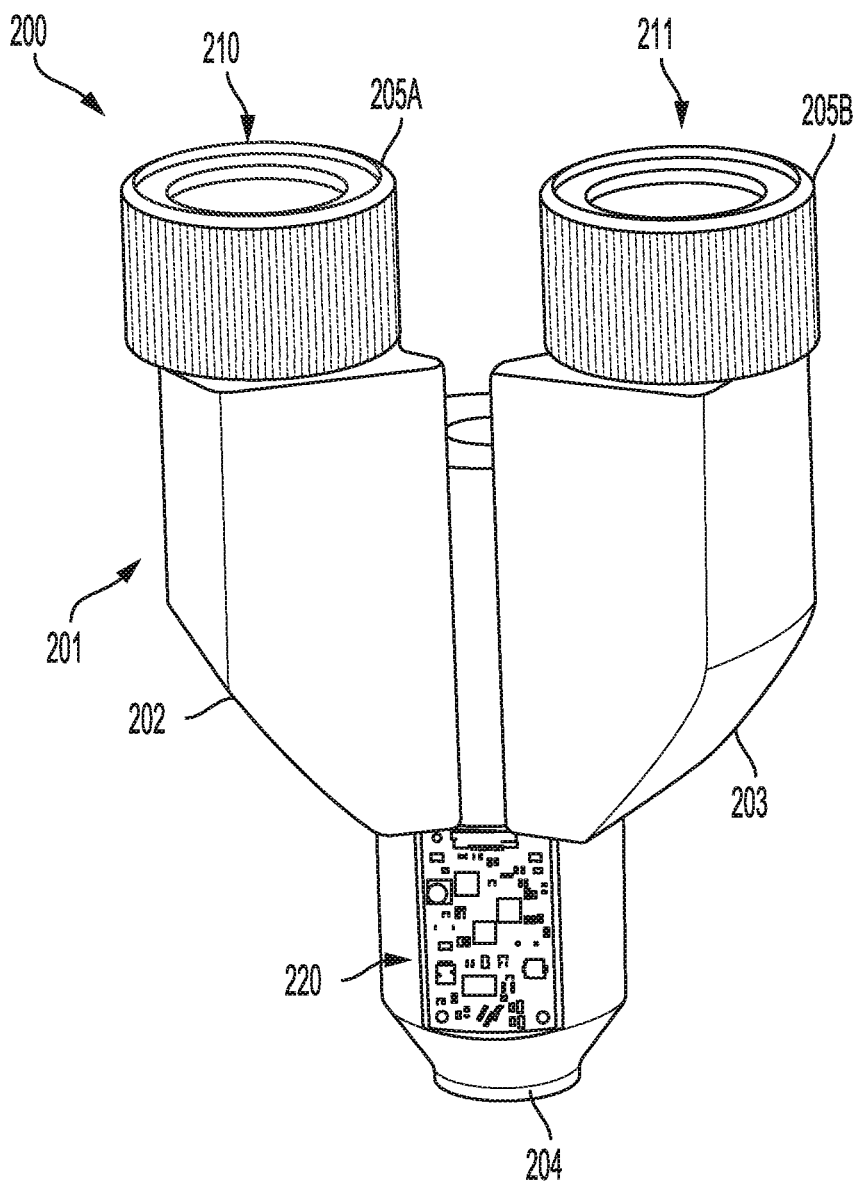
FIG. 2 is a bottom perspective view of an alternate embodiment of a multimodal imaging apparatus, according to some embodiments.

FIG. 2 illustrates a further embodiment of an imaging apparatus 200, in accordance with some embodiments. As shown, imaging apparatus 200 includes housing 201, within which one or more imaging devices (not shown) may be disposed. Housing 201 includes first housing section 202 and second housing section 203 connected to a central housing portion 204. The central housing portion 204 may include and/or operate as a hinge connecting the first and second housing sections 202 and 203, and about which the first and second housing portions 202 and 203 may rotate. By rotating the first and/or second housing sections 202 and/or 203 about the central housing portion 204, a distance separating the first and second housing sections 202 and 203 may be increased or decreased accordingly. Before and/or during operation of the imaging apparatus 200, a person may rotate the first and second housing sections 202 and 203 to accommodate a distance separating the person's eyes, such as to facilitate alignment of the person's eyes with openings of the first and second housing sections 202 and 203.

The first and second housing sections 202 and 203 may be configured in the manner described for first and second housing sections 102 and 103 in connection with FIGS. 1A-1B. For instance, each housing section may accommodate one or more imaging devices therein, such as an optical imaging device, a fluorescent imaging device, and/or an OCT imaging device. In FIG. 2, each housing section 202 and 203 is coupled to a separate one of front housing sections 205A and 205B. Front housing sections 205A and 205B may be shaped to conform to the facial profile of a person using the imaging apparatus 200, such as conforming to portions of the person's face proximate the person's eyes. In one example, the front housing sections 205A and 205B may be formed using a pliable plastic that may conform to the person's facial profile when placed against the person's face. Front housing sections 205A and 205B may have respective openings 211 and 210 that correspond with openings of first and second housing sections 202 and 203, such as in alignment with the openings of the first and second housing sections 202 and 203 to provide minimally obstructed optical paths from the person's eyes to the imaging devices of the imaging apparatus 200. In some embodiments, the openings 210 and 211 may be covered with a transparent window made using glass or plastic.

In some embodiments, the central housing section 204 may include one or more electronic circuits (e.g., integrated circuits, printed circuit boards, etc.) for operating the imaging apparatus 200. In some embodiments, one or more processors may be disposed in central housing section 204, such as for analyzing data captured using the imaging devices. The central housing section 204 may include wired and/or wireless means of electrically communicating to other devices and/or computers, such as described for imaging apparatus 100. For instance, further processing may be performed by the devices and/or computers communicatively coupled to imaging apparatus 200. In some embodiments, the electronic circuits onboard the imaging apparatus 200 may process captured image data based on instructions received from such communicatively coupled devices or computers. In some embodiments, the imaging apparatus 200 may initiate an image capture sequence based on instructions received from a devices and/or computers communicatively coupled to the imaging apparatus 200.

As described herein including in connection with imaging apparatus 100, imaging apparatus 200 may include a gripping member and/or a mounting member, and/or a fixator.

Figure 3A:
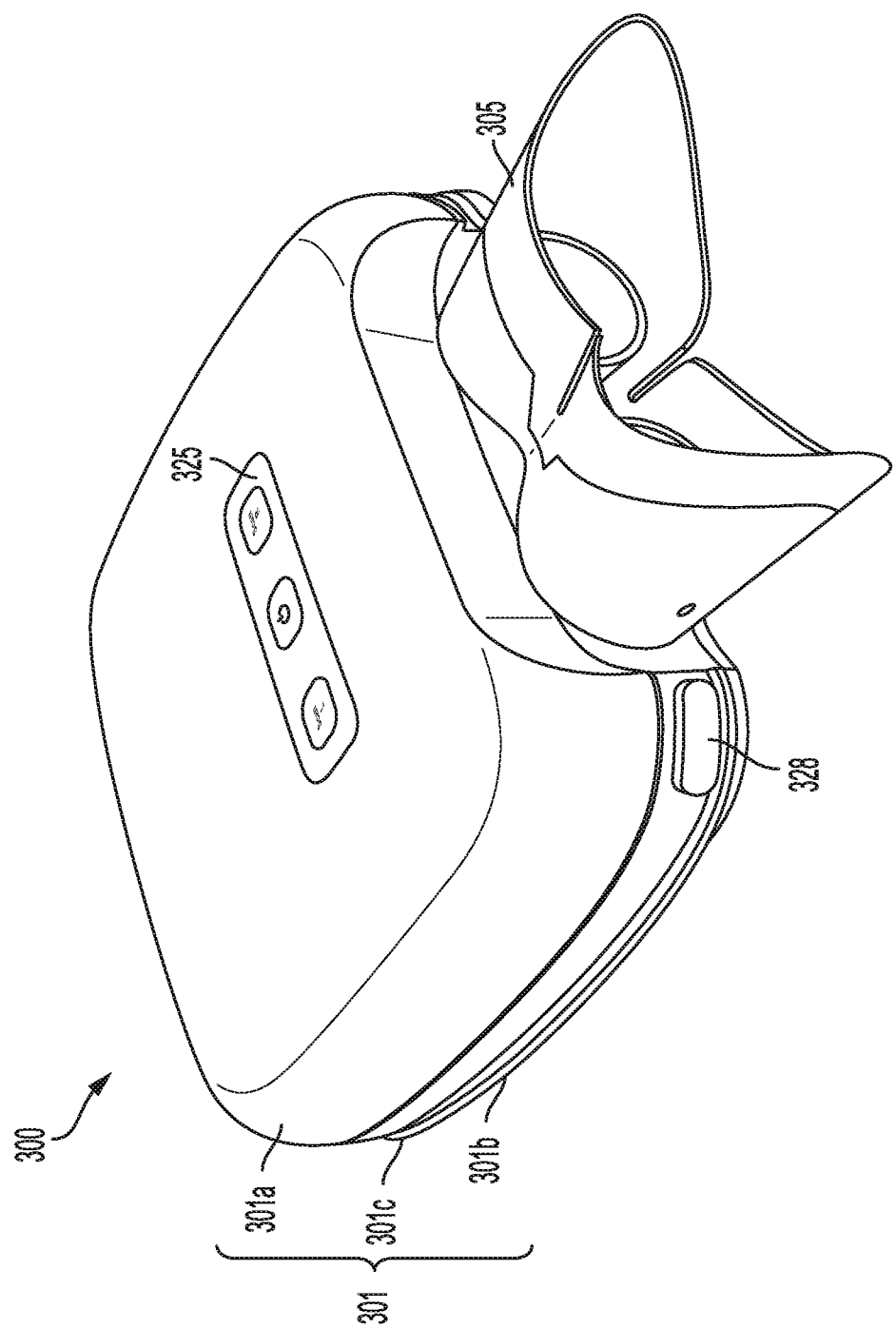
FIG. 3A is a rear perspective view of a further alternative embodiment of a multimodal imaging apparatus, according to some embodiments.
Figure 3C:
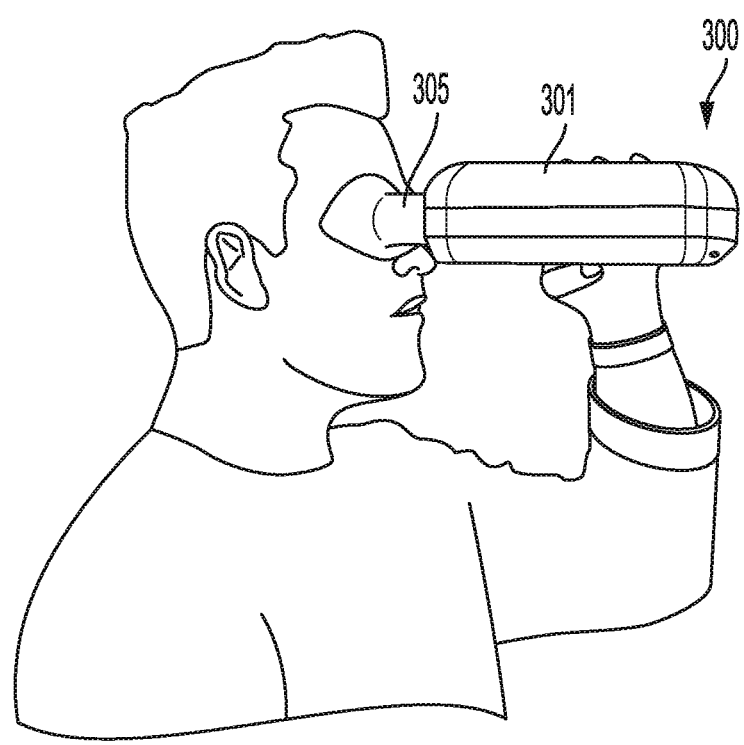
FIG. 3C is a side view of a subject operating the multimodal imaging apparatus of FIGS. 3A-3B, according to some embodiments.
Figure 3D:
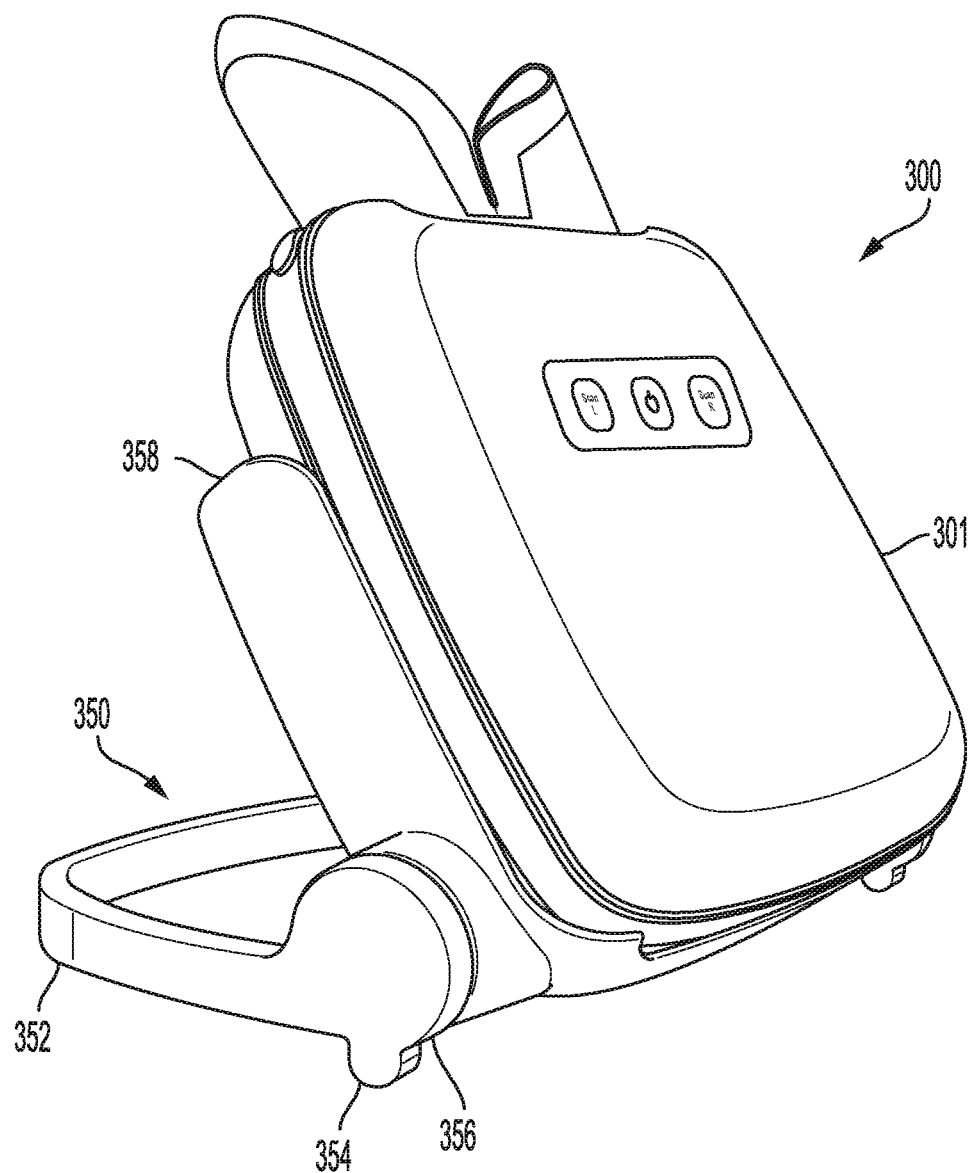
FIG. 3D is a side perspective view of the multimodal imaging apparatus of FIGS. 3A-3C supported by a stand, according to some embodiments.

FIGS. 3A-3D illustrate a further embodiment of an imaging apparatus 300, according to some embodiments. As shown in FIG. 3A, imaging apparatus 300 has a housing 301, including multiple housing portions 301a, 301b, and 301c. Housing portion 301a has a control panel 325 including multiple buttons for turning imaging apparatus 300 on or off, and for initiating scan sequences. FIG. 3B is an exploded view of imaging apparatus 300 illustrating components disposed within housing 301, such as imaging devices 322 and 323 and electronics 320. Imaging devices 322 and 323 may include one or more of: white light imaging components, a fluorescence imaging components, infrared (IR) imaging components, and/or OCT imaging components, in accordance with various embodiments. In one example, imaging device 322 may include an OCT imaging components and/or an IR imaging components, and imaging device 323 may include a white light imaging device and/or a fluorescence imaging device. Imaging apparatus further includes front housing portion 305 configured to receive a person's eyes for imaging, as illustrated, for example, in FIG. 3C. FIG. 3D illustrates imaging apparatus 300 seated in stand 350, as described further herein.

As shown in FIGS. 3A-3D, housing portions 301a and 301b may substantially enclose imaging apparatus 300, such as by having all or most of the components of imaging apparatus 300 disposed between housing portions 301a and 301b. Housing portion 301c may be mechanically coupled to housing portions 301a and 301b, such as using one or more screws fastening the housing 301 together. As illustrated in FIG. 3B, housing portion 301c may have multiple housing portions therein, such as housing portions 302 and 303 for accommodating imaging devices 322 and 323. For example, in some embodiments, the housing portions 302 and 303 may be configured to hold imaging devices 322 and 323 in place. Housing portion 301c is further includes a pair of lens portions in which lenses 310 and 311 are disposed. Housing portions 302 and 303 and the lens portions may be configured to hold imaging devices 322 and 323 in alignment with lenses 310 and 311. Housing portions 302 and 303 may accommodate focusing parts 326 and 327 for adjusting the foci of lenses 310 and 311. Some embodiments may further include securing tabs 328. By adjusting (e.g., pressing, pulling, pushing, etc.) securing tabs 328, housing portions 301a, 301b, and/or 301c may be decoupled from one another, such as for access to components of imaging apparatus 300 for maintenance and/or repair purposes.

Electronics 320 may be configured in the manner described for electronics 320 in connection with FIG. 2. Control panel 325 may be electrically coupled to electronics 320. For example, the scan buttons of control panel 325 may be configured to communicate a scan command to electronics 320 to initiate a scan using imaging device 322 and/or 323. As another example, the power button of control panel 325 may be configured to communicate a power on or power off command to electronics 320. As illustrated in FIG. 3B, imaging apparatus 300 may further include electromagnetic shielding 324 configured to isolate electronics 320 from sources of electromagnetic interference (EMI) in the surrounding environment of imaging apparatus 300. Including electromagnetic shielding 324 may improve operation (e.g., noise performance) of electronics 320. In some embodiments, electromagnetic shielding 324 may be coupled to one or more processors of electronics 320 to dissipate heat generated in the one or more processors.

In some embodiments, imaging apparatus described herein may be configured for mounting to a stand, as illustrated in the example of FIG. 3D. In FIG. 3D, imaging apparatus 300 is supported by stand 350, which includes base 352 and holding portion 358. Base 352 is illustrated including a substantially U-shaped support portion and has multiple feet 354 attached to an underside of the support portion. Base 352 may be configured to support imaging apparatus 300 above a table or desk, such as illustrated in the figure. Holding portion 358 may be shaped to accommodate housing 301 of imaging apparatus 300. For example, an exterior facing side of holding portion 358 may be shaped to conform to housing 301.

As illustrated in FIG. 3D, base 352 may be coupled to holding portion 358 by a hinge 356. Hinge 356 may permit rotation about an axis parallel to a surface supporting base 352. For instance, during operation of imaging apparatus 300 and stand 350, a person may rotate holding portion 358, having imaging apparatus 300 seated therein, to an angle comfortable for the person to image one or both eyes. For example, the person may be seated at a table or desk supporting stand 350. In some embodiments, a person may rotate imaging apparatus 300 about an axis parallel to an optical axis along which imaging devices within imaging apparatus image the person's eye(s). For instance, in some embodiments, stand 350 may alternatively or additionally include a hinge parallel to the optical axis.

In some embodiments, holding portion 358 (or some other portion of stand 350) may include charging hardware configured to transmit power to imaging apparatus 300 through a wired or wireless connection. In one example, the charging hardware in stand 350 may include a power supply coupled to one or a plurality of wireless charging coils, and imaging apparatus 300 may include wireless charging coils configured to receive power from the coils in stand 350. In another example, charging hardware in stand 350 may be coupled to an electrical connector on an exterior facing side of holding portion 358 such that a complementary connector of imaging apparatus 300 interfaces with the connector of stand 350 when imaging apparatus 300 is seated in holding portion 358. In accordance with various embodiments, the wireless charging hardware may include one or more power converters (e.g., AC to DC, DC to DC, etc.) configured to provide an appropriate voltage and current to imaging apparatus 300 for charging. In some embodiments, stand 350 may house at least one rechargeable battery configured to provide the wired or wireless power to imaging apparatus 300. In some embodiments. Stand 350 may include one or more power connectors configured to receive power from a standard wall outlet, such as a single-phase wall outlet.

In some embodiments, front housing portion 305 may include multiple portions 305a and 305b. Portion 305a may be formed using a mechanically resilient material whereas front portion 305b may be formed using a mechanically compliant material, such that front housing portion 305 is comfortable for a user to wear. For example, in some embodiments, portion 305a may be formed using plastic and portion 305b may be formed using rubber or silicone. In other embodiments, front housing portion 305 may be formed using a single mechanically resilient or mechanically compliant material. In some embodiments, portion 305b may be disposed on an exterior side of front housing portion 305, and portion 305a may be disposed within portion 305b.

II. Optical Coherence Tomography and/or Infrared (IR) Imaging Techniques

The inventors have developed improved OCT and IR imaging techniques that may be implemented alone or in combination within a multi-modal imaging apparatus. In some embodiments, combinations of OCT and IR imaging components described further herein may be included together in one or both of the first and second housing sections of a multi-modal imaging apparatus. In some embodiments, the OCT imaging components may be disposed in one of the first or second housing sections, and IR imaging components may be disposed in the other housing section. The inventors recognized that combining OCT and IR components, such that at least a portion of the components shared an imaging path, reduces the form factor and cost of producing a multi-modal imaging apparatus.

In some embodiments, OCT techniques may focus broadband light on a subject's retina fundus and also at a reference surface, and then combine light reflected from the subject's retina fundus with light reflected by the reference surface to obtain information about structures in the retina fundus. The information may be determined based on detected interference between the light received from the subject's retina fundus and the light received from the reference surface. In some embodiments, OCT techniques may provide depth imaging information pertaining to structures beneath the surface of the retina fundus. In some embodiments, a beam splitter may split source light between sample components, which provide the light to the subject's retina fundus, and reference components, which provide the light to the reference surface. The beam splitter may then combine the light reflected from the sample and reference components and provide the combined light to the interferometer. In some embodiments, the interferometer may detect interference by determining a phase difference between the sampled light and the reference light.

In some embodiments, OCT may be performed in the time domain to scan the depth of a subject's retina fundus. For example, in some embodiments, the difference in path length between the reference components and the sample components may be adjusted. In some embodiments, OCT may be performed in the frequency domain by using an interferometer to detect interference in a particular light spectrum. Embodiments described herein may be configured to perform time domain and/or frequency domain OCT.

In some embodiments, IR imaging components may perform IR imaging of the subject's retina fundus, which may provide depth and/or temperature information of the subject's retina fundus. In some embodiments, at least some IR and OCT imaging components described herein may share an optical path. For example, in some embodiments, IR imaging and OCT imaging may be performed at different times using at least some of the same optical components, as described herein.

It should be appreciated that OCT and IR techniques described herein may be used alone or in combination within a single mode or multi-modal imaging apparatus. Moreover, some embodiments may include only OCT components or only IR components, as techniques described herein may be implemented alone or in combination.

Figure 4A:
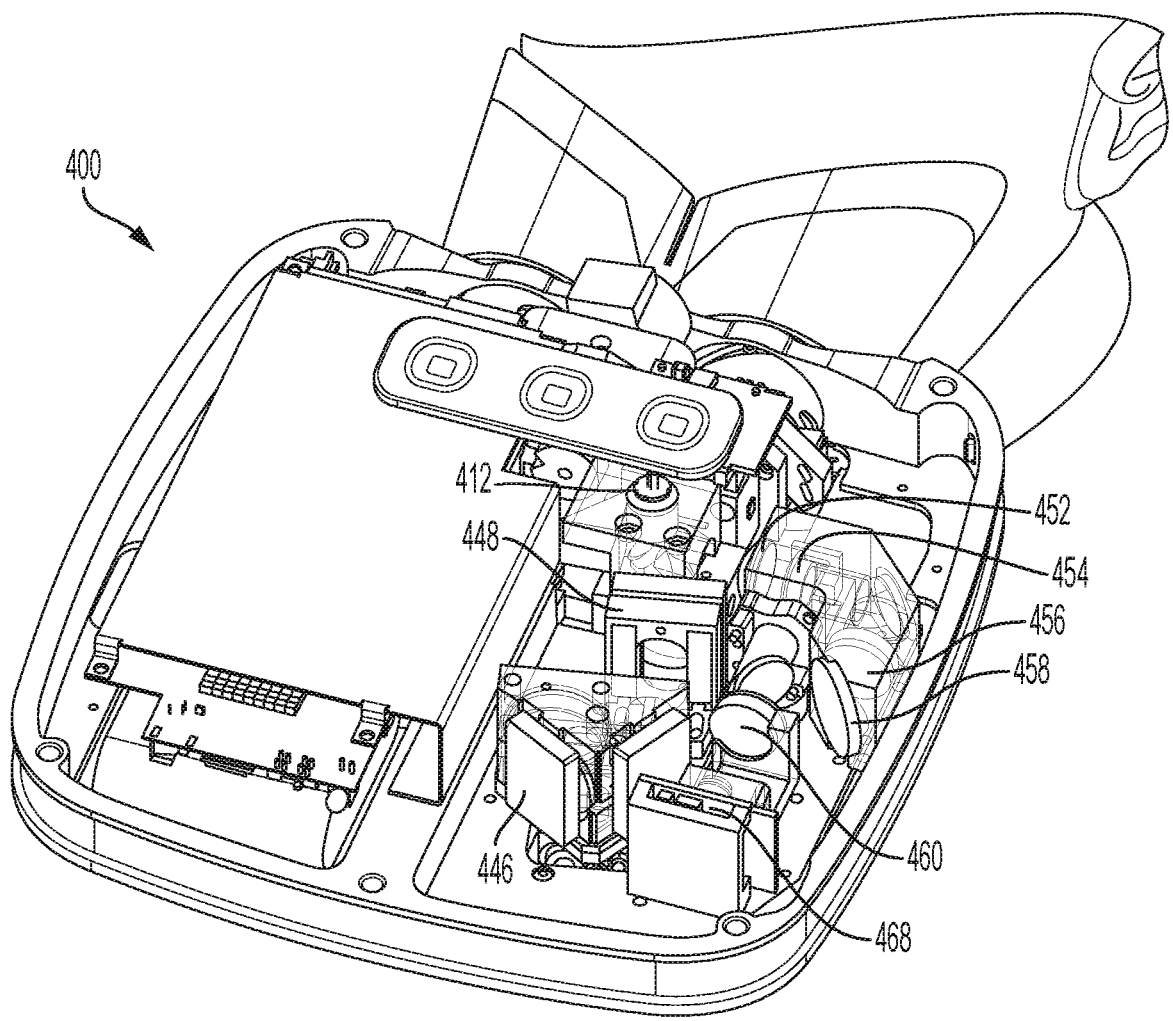
FIG. 4A is a top perspective view of a multimodal imaging apparatus comprising a combination Optical Coherence Tomography (OCT) and infrared (IR) imaging device, according to some embodiments.
Figure 4B:
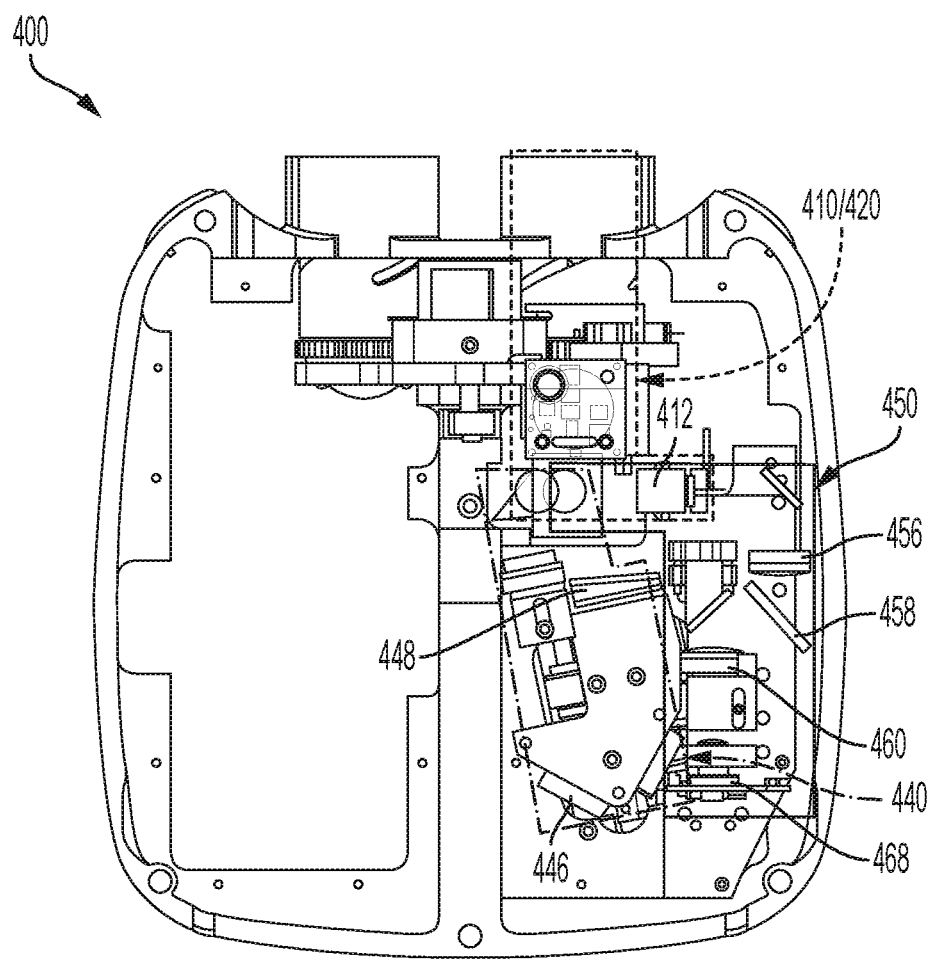
FIG. 4B is a top view of the multimodal imaging apparatus of FIG. 4A with a portion of the housing and some of the imaging devices removed, according to some embodiments.
Figure 4C:
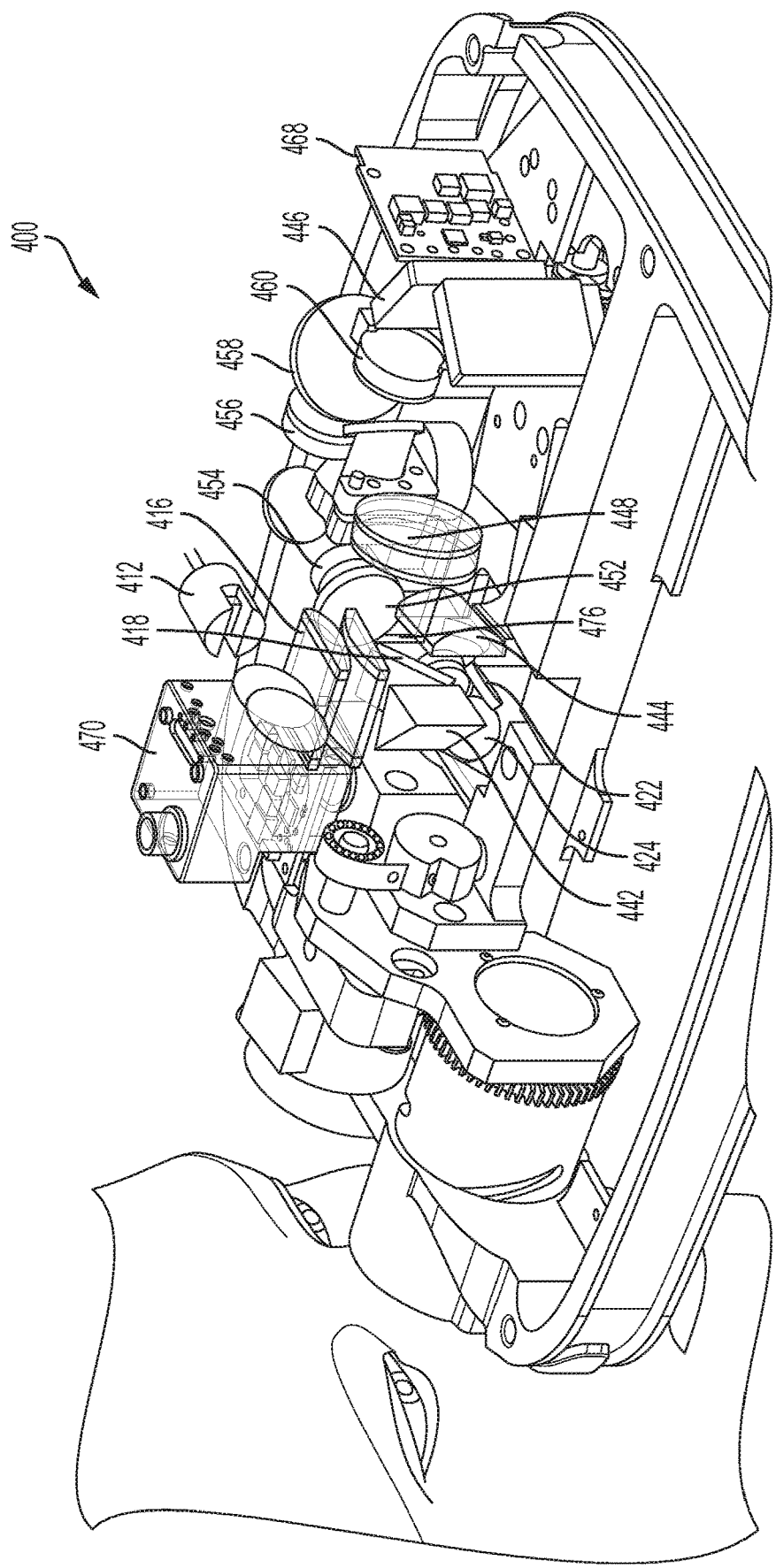
FIG. 4C is a side perspective view of the multimodal imaging apparatus as shown in FIG. 4B, according to some embodiments.

FIGS. 4A-4C illustrate a multimodal imaging apparatus 400 comprising a combination OCT/IR imaging device with OCT source components 410, sample components 420, reference components 440, and detection components 450, according to some embodiments. FIG. 4A is a top perspective view of imaging apparatus 400, FIG. 4B is a top view of imaging apparatus 400, and FIG. 4C is a side perspective view of imaging apparatus 400. In some embodiments, source components 410 may include one or more sources of light, such as a super-luminescent diode, as well as optical components configured to focus light from the source(s). Of source components 410, light source 412, cylindrical lenses 416, and beam splitter 418 are shown in FIGS. 4A-4C. In some embodiments, sample components 420 may be configured to provide light from source components 410 to the eye of a subject via one or more optical components. Of sample components 420, scanning mirror 422, and fixation dichroic 424 are shown in FIGS. 4A-4C. In some embodiments, reference components 440 may be configured to provide light from source components 410 to one or more reference surfaces via one or more optical components. Of reference components 440, dispersion compensator 442, cylindrical lens 444, fold mirrors 446, and reference surface 448 are shown in FIGS. 4A-4C. In some embodiments, detection components 450 may be configured to receive reflected light from sample components 420 and reference components 440 responsive to providing light from source components 410 to sample components 420 and reference components 440. Of detection components 450, aspherical lens 452, plano-concave lens 454, achromatic lens 456, transmissive grating 458, and achromatic lens 460 are shown in FIGS. 4A-4C.

Figure 4D:
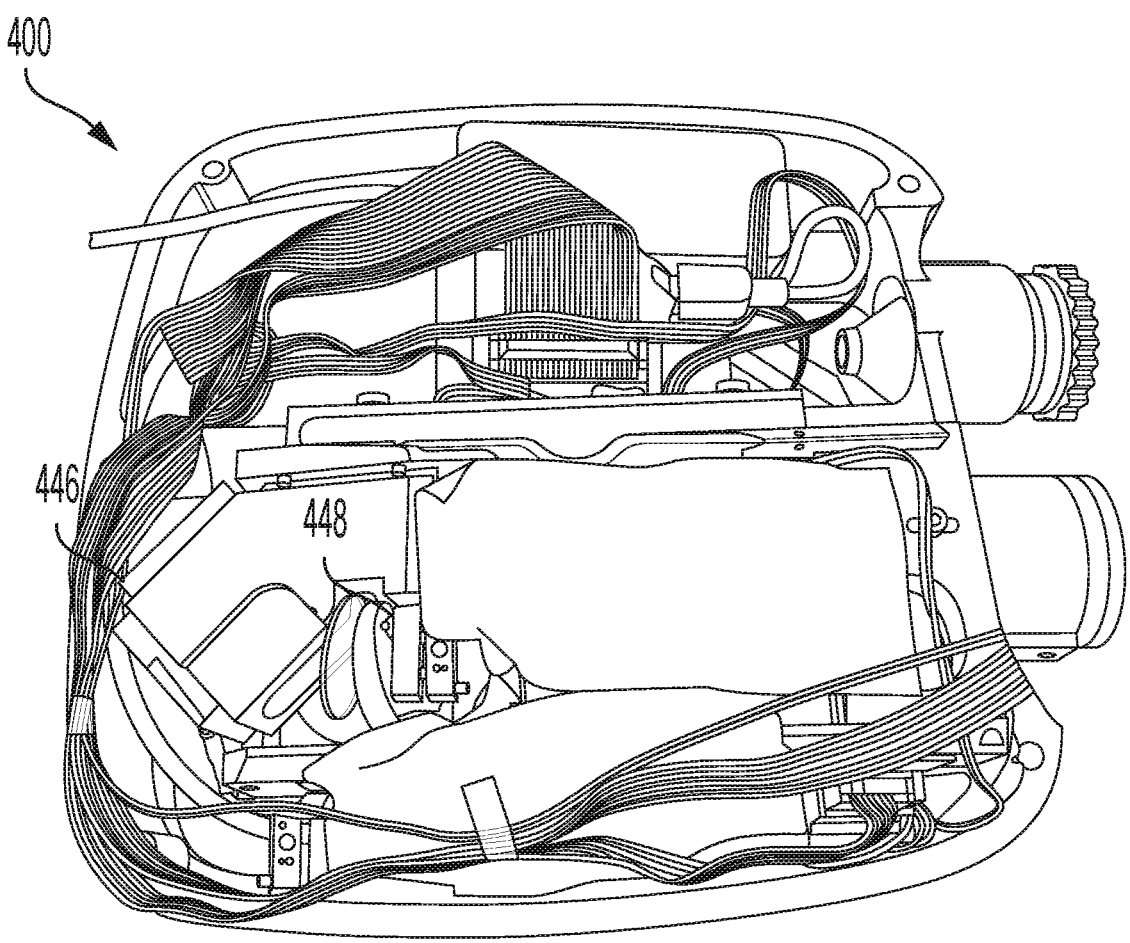
FIG. 4D is a top view of the multimodal imaging apparatus of FIG. 4A with the top portion of the housing removed, according to some embodiments.
Figure 4E:
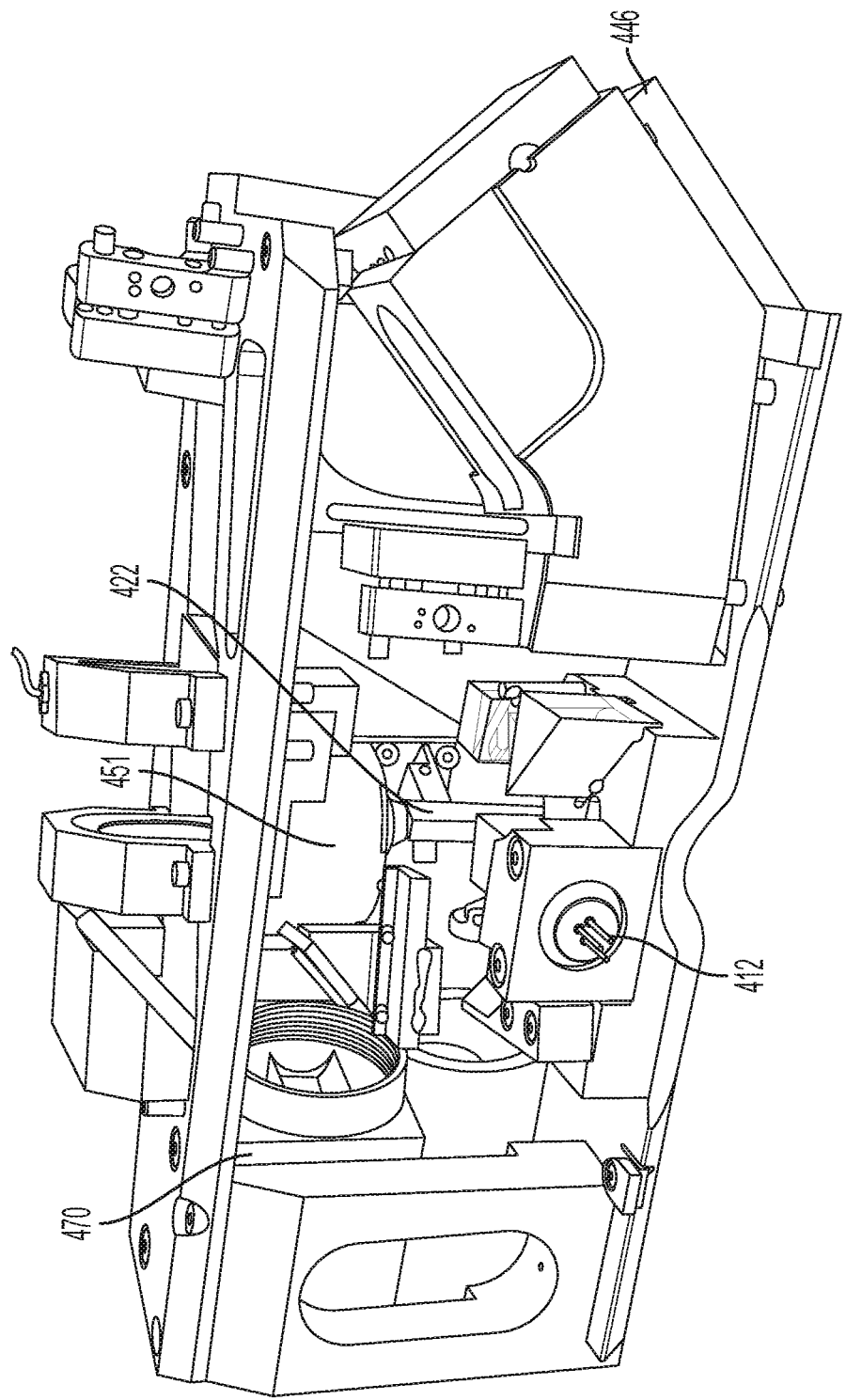
FIG. 4E is a side perspective view of components of the OCT and IR imaging device of the multimodal imaging apparatus of FIGS. 4A-4D, according to some embodiments.

FIG. 4D is a top view of imaging apparatus 400 with the top portion of the housing removed, according to some embodiments. Some of reference components 440, such as fold mirrors 446 and reference surface 448 are shown in FIG. 4D. FIG. 4E is a side perspective view of components of the OCT and IR imaging device of imaging apparatus 400, according to some embodiments. IR camera 470, light source 412, scanning mirror 422, and OCT motor scanning window 451 are shown in FIG. 4E.

Further examples of source components 410, sample components 420, reference components 440, and detection components 450 that may be included in imaging apparatus 400 are described herein including with reference to FIGS. 5A-5I.

Figure 5A:
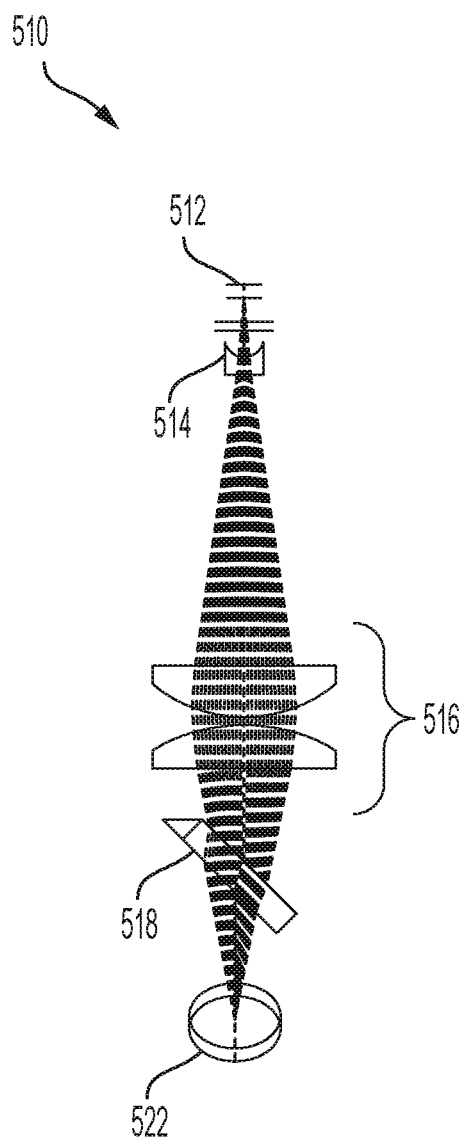
FIG. 5A is a top view of source components of the OCT imaging device of FIGS. 4A-4C, according to some embodiments.

FIG. 5A is a top view of exemplary source components 510, according to some embodiments. In some embodiments, source components 510 may be included as source components 410 in OCT imaging device 400. In some embodiments, source components 510 may be configured to provide light to other OCT components, such as sample and/or reference components. For example, source components 510 may be configured to provide light to sample components for providing to a subject's eye, and to reference components for providing to a reference surface such that light detected from the subject's eye responsive to providing light via the sample components can be compared to light provided to the reference surface.

In FIG. 5A, source components 510 include light source 512, beam-spreader 514, cylindrical lenses 516, and beam splitter 518. In some embodiments, light source 512 may include a super-luminescent diode. In some embodiments, light source 512 may be configured to provide polarized light (e.g., linearly, circularly, elliptically, etc.). In some embodiments, light source 512 may be configured to provide broadband light, such as including white light and IR light. In some embodiments, light source 512 may include a super-luminescent diode having a spectral width of greater than 40 nm and a central wavelength between 750 nm and 900 nm. In one example, light source 512 may have a central wavelength at 850 nm, where scattering by the tissue of the subject is lower than at other wavelengths. In some embodiments, light source 512 may include a super-luminescent diode having a single lateral spatial mode. In some embodiments, light source 512 may include a vertical-cavity surface-emitting laser (VCSEL) with an adjustable mirror on one side. In some embodiments, the VCSEL may have a tuning range of greater than 100 nm using a micro-mechanical movement (MEMs). In some embodiments, the light source 512 may include a plurality of light sources that, together, have a broad spectral width. In one example, light source 512 may include a plurality of laser diodes in close proximity. Laser diodes are cost-effective because they are less expensive than super-luminescent diodes and have higher brightness and shorter pulse duration than superluminescent diodes. In some embodiments, the spectrum of each laser diode may be superimposed by the grating over separate wavelength on the CMOS sensor.

In some embodiments, beam-spreader 514 may include a cylindrical beam-spreader. In some embodiments, beam-spreader 514 may include an aspherical lens. In some embodiments, beam-spreader 514 and/or cylindrical lenses 516 may be configured to form light from light source 512 into an elongated line for scanning a subject's retina fundus. For example, when the light reaches the subject's retina fundus, the light may be focused in a first direction and elongated in a second direction perpendicular to the first direction. In some embodiments, a fold mirror may be positioned between beam-spreader 514 and cylindrical lenses 516. In some embodiments, cylindrical lenses 516 may be configured to spatially focus source light on a scanning mirror 522, which may be included with other sample components coupled to source components 510. In some embodiments, scanning mirror 522 may be actuated with one or more stepper motors, galvanometers, polygonal scanners, micro-electromechanical switch (MEMS) mirrors, and/or other moving mirror devices. As shown in FIG. 5A, cylindrical lenses 516 face opposite directions, with rounded surfaces facing one another.

In some embodiments, beam splitter 518 may be configured to couple light from light source 512 to other OCT components, such as sample components and/or reference components. In some embodiments, beam splitter 518 may be configured to couple light to sample components such as scanning mirror 522, which in turn may be configured to provide the light to other sample components. In some embodiments, beam splitter 518 may be configured as a long-pass filter. In some embodiments, beam splitter 518 may be configured to reflect white source light and transmit IR source light incident from light source 512. In some embodiments, beam splitter 518 may be configured to transmit IR light to sample components and reflect white light to reference components. In some embodiments, beam splitter 518 may be configured to provide half of the source light to the sample components and half of the source light to the reference components. In some embodiments, beam splitter 518 may be configured to provide more source light to the sample components than to the reference components. In some embodiments, beam splitter 518 may be further configured to provide interfering light from the sample and reference components to detection components. In some embodiments, beam splitter 518 may be a plate beam splitter.

Figure 5B:
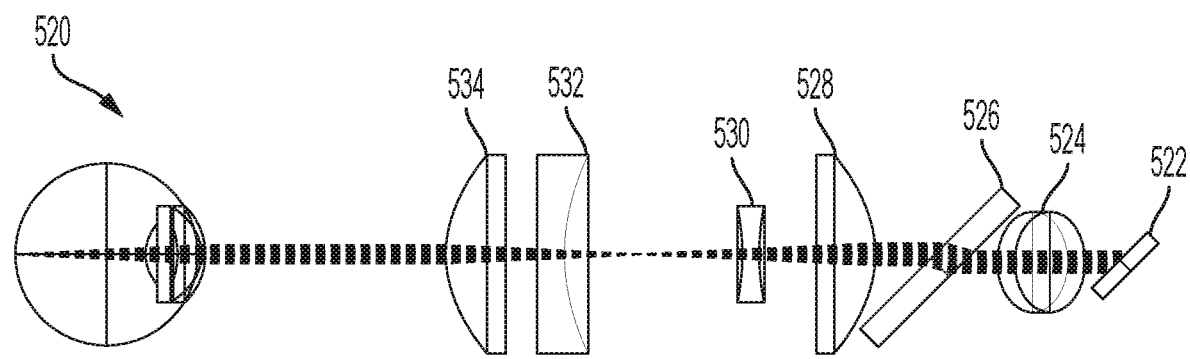
FIG. 5B is a side view of sample components of the OCT imaging device of FIG. 5A, according to some embodiments.
Figure 5C:
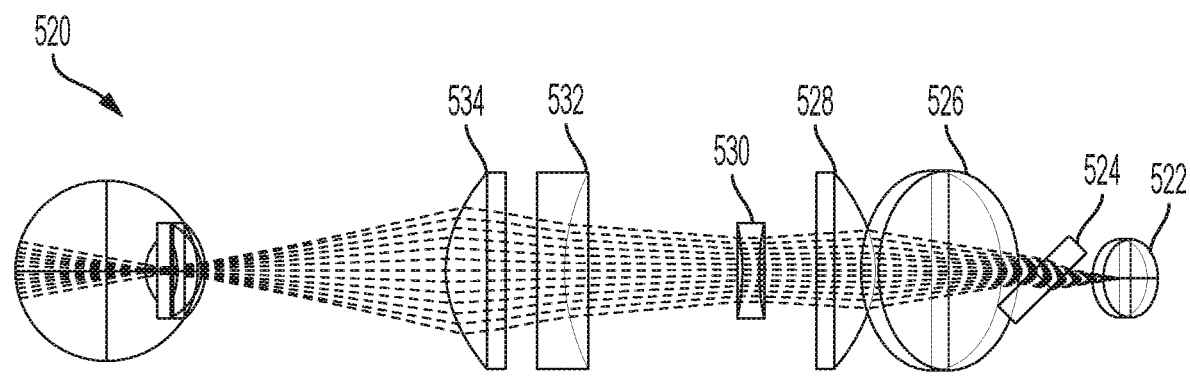
FIG. 5C is a top view of the sample components shown in FIG. 5B, according to some embodiments.

FIG. 5B is a side view of exemplary sample components 520, and FIG. 5C is a top view of sample components 520, according to some embodiments. In some embodiments, sample components 520 may be included as sample components 420 in OCT imaging device 400. As shown in FIGS. 5B-5C, sample components include scanning mirror 522, fixation dichroic 524, IR fundus dichroic 526, plano-convex lens 528, biconcave lens 530, plano-concave lens 532, and plano-convex lens 534. In some embodiments, fixation dichroic 524 may be configured to reflect some of the source light towards fixation components such as a fixation display. In some embodiments, fixation dichroic 524 may be configured as a long-pass filter, such that short wavelength (e.g., visible) light is reflected by fixation dichroic 524. In some embodiments, IR fundus dichroic 526 may be configured as a short-pass filter, such that long wavelength (e.g., IR) light is reflected by IR fundus dichroic 526. In some embodiments, IR fundus dichroic 526 may be configured to reflect IR light and transmit white light. In some embodiments, lenses 528, 530, 532, and/or 534 may be adjusted to provide diopter compensation. In some embodiments, these lenses may be adjusted to compensate for subjects having different corrections, hyperopia or presbyopia. FIGS. 5B and 5C further illustrate how sample components 520 may focus source light on the retina of a subject. As shown in FIG. 5B, the light provided by sample components 510 may focus on a point at the back of the eye when viewed from the side. As shown in FIG. 5C, the light provided by sample components 510 may focus on a point at the front of the eye (e.g., the pupil) such that the light is spread over a line of points at the back of the eye when viewed from the top.

Figure 5D:
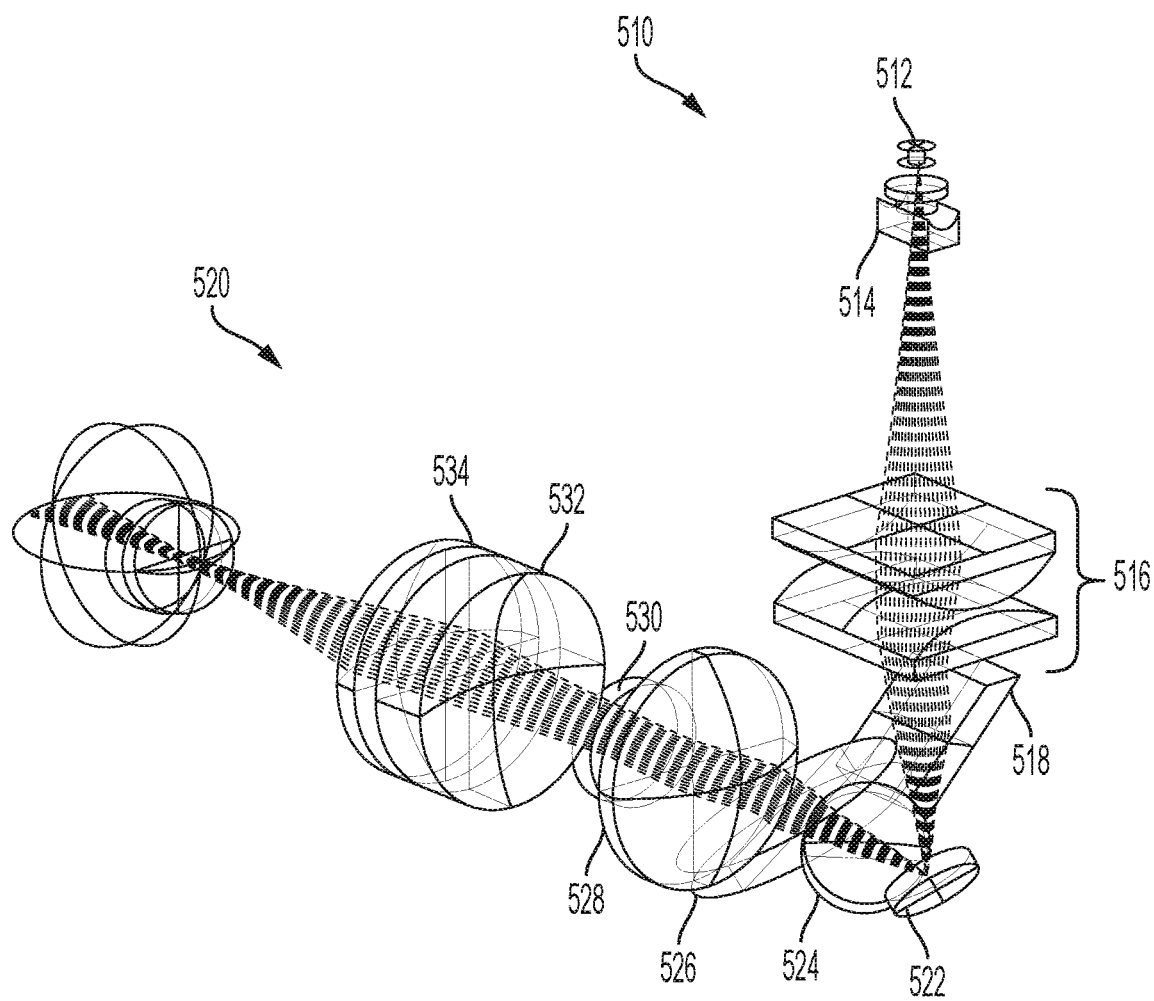
FIG. 5D is a perspective view of the source and sample components shown in FIGS. 5A-5C, according to some embodiments.

FIG. 5D is a perspective view of source components 510 and sample components 520 in an optically coupled configuration, according to some embodiments. In FIG. 5D, scanning mirror 522 is shown configured to couple light from source components 510 to sample components 520. In some embodiments, scanning mirror 522 may be configured to couple IR light from source components 510 to sample components 520. In some embodiments, sample components 520 may focus light reflected back from a subject's eye on scanning mirror 522 to provide the reflected light to beam splitter 518. In some embodiments, beam splitter 518 may be further configured to provide reflected light to detection components.

Figure 5E:
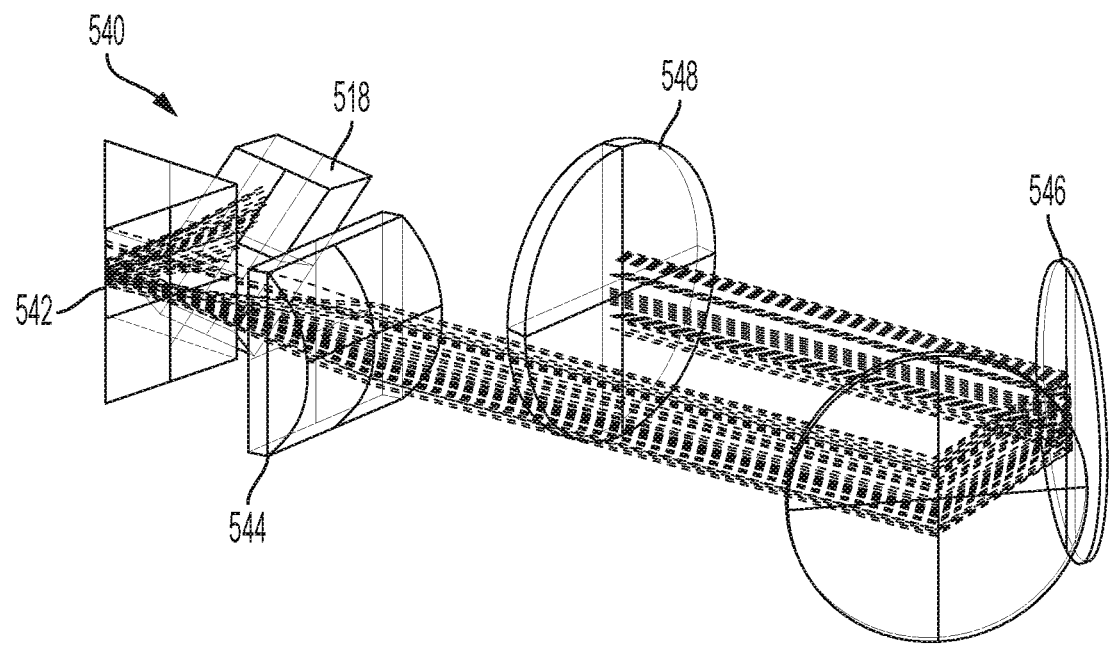
FIG. 5E is a perspective view of reference components of the OCT imaging device of FIGS. 4A-4C, according to some embodiments.

FIG. 5E is a perspective view of exemplary reference components 540, according to some embodiments. In some embodiments, reference components 540 may be included as reference components 440 in OCT imaging device 400. As shown in FIG. 5E, reference components 540 include dispersion compensator 542, collimating lens 544, fold mirrors 546, and reference surface 548. As shown in FIG. 5E, beam splitter 518 of source components 510 may be configured to reflect white light to reference components 540. In some embodiments, dispersion compensator 542 may include a mirror. In some embodiments, dispersion compensator 542 may be configured to provide a same amount of dispersion into light passing through reference components 540 as provided to light passing through sample components 520 by a subject's eye. In some embodiments, collimating lens 544 may include a cylindrical plano-convex lens. In some embodiments, reference surface 548 may include wedge glass. In some embodiments, reference surface 548 may include a diffuse reflector configured to reflect similarly to the human eye, as each point of reflection acts as a point source. In some embodiments, reference surface 548 may include a mirror. In some embodiments, reference components 540 may have an adjustable path length of +/−5 mm.

Figure 5F:
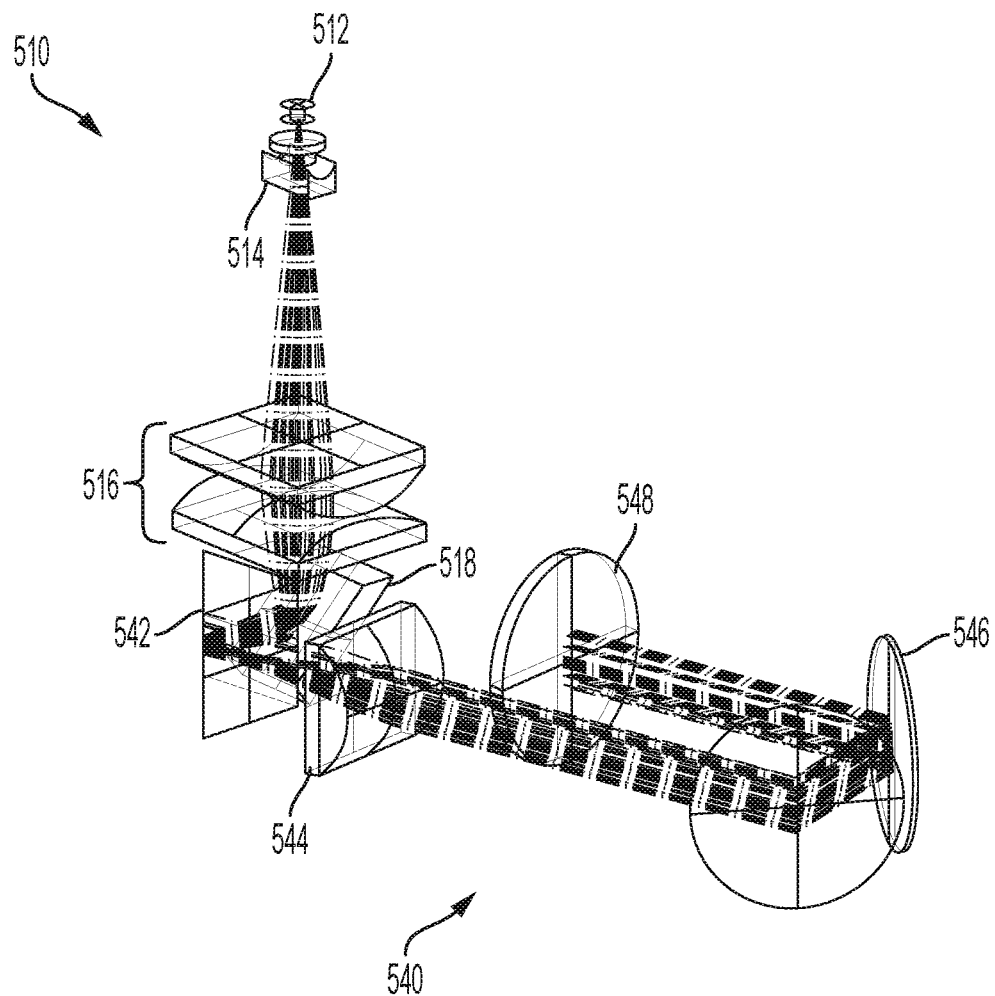
FIG. 5F is a perspective view of the source and reference components shown in FIGS. 5A and 5E, according to some embodiments.

FIG. 5F is a perspective view of source components 510 and reference components 540 in an optically coupled configuration, according to some embodiments. In FIG. 5F, beam splitter 518 is shown configured to couple light from light source 512 of source components 510 to reference components 540. In some embodiments, reference components 540 may be configured to return light from reference surface 548 to beam splitter 518, which may provide the returned reference light to detection components.

Figure 5G:
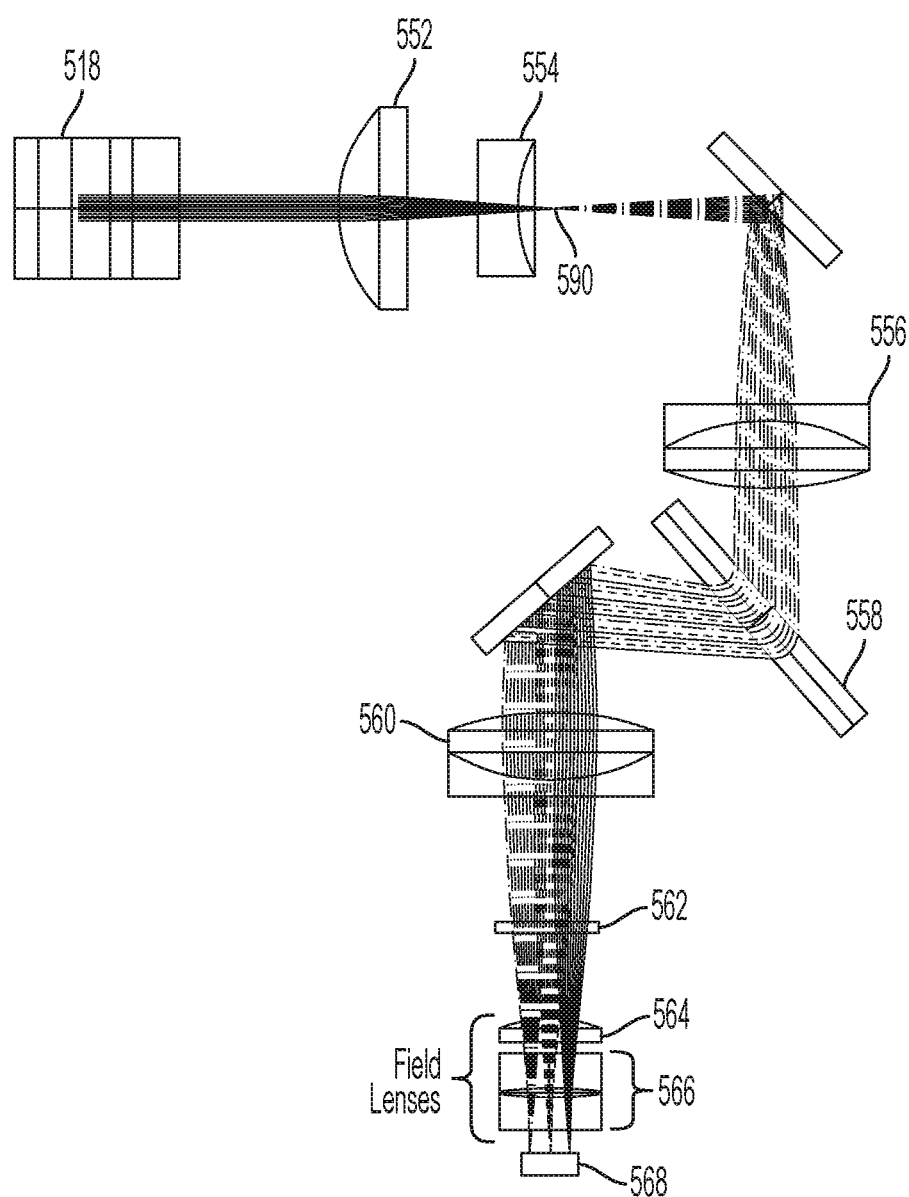
FIG. 5G is a top view of detection components of the OCT imaging device of FIGS. 4A-4C, according to some embodiments.

FIG. 5G is a top view of exemplary detection components 550, according to some embodiments. In some embodiments, detection components 550 may be included as detection components 450 in OCT imaging device 400. As shown in FIG. 5G, detection components 550 include aspherical lens 552, plano-concave lens 554, achromatic lens 556, transmissive grating 558, achromatic lens 560, polarizer 562, field lenses including plano-convex lens 564 and plano-concave lenses 566, and OCT camera 568. In some embodiments, aspherical lens 552, plano-concave lens 554, and achromatic lens 556 may be configured to expand detected light received from beam splitter 518. For example, the received light may include reflected light from a subject's eye from sample components, as well as light reflected by reference surface 548 of reference components 540. In some embodiments, OCT camera 568 may include an interferometer, such as a Mach-Zehnder interferometer and/or a Michelson interferometer.

In some embodiments, transmissive grating 558 may improve the spectral signal to noise ratio for light received by OCT camera 568. In some embodiments, transmissive grating 558 may be configured provide light at normal incidence to OCT camera 568. In some embodiments, transmissive grating 558 may enhance the noise performance of the transfer function of OCT camera 568.

In some embodiments, transmissive grating 558 may be configured to increase symmetry and reduce aberrations in the received light. In some embodiments, transmissive grating 558 may be configured to transmit the received light at a Littrow angle. In some embodiments, transmissive grating 558 may be configured to split the received light by wavelength. In some embodiments, transmissive grating 558 may have a dispersion grating between 1200-1800 lines/mm. In some embodiments, transmissive grating 558 may have a dispersion grating between 1500-1800 lines/mm. In some embodiments, transmissive grating 558 may have a dispersion grating of 1800 lines/mm.

In some embodiments, achromatic lens 560 and the field lenses may be configured to focus the light from transmissive grating 558 toward OCT camera 568, which may be configured to detect the focused light. Polarizer 562 is shown positioned between achromatic lens 560 and the field lenses. In some embodiments, polarizer 562 may have a same polarization as light source 512 of source components 510, such that light having a different polarization from light source 512 may be filtered out. In some embodiments, polarizer 562 may have a different polarization from light source 512, such as for transmitting light received from a subject's eye having been reflected by the eye with a different (e.g., opposite) polarization. In some embodiments, the field lenses may be configured to flatten the field of the received light. In some embodiments, the field lenses may be configured to adjust the chief ray angle of the received light. In some embodiments, the field lenses may be configured to effect diverging rays in the received light.

Figure 5H:
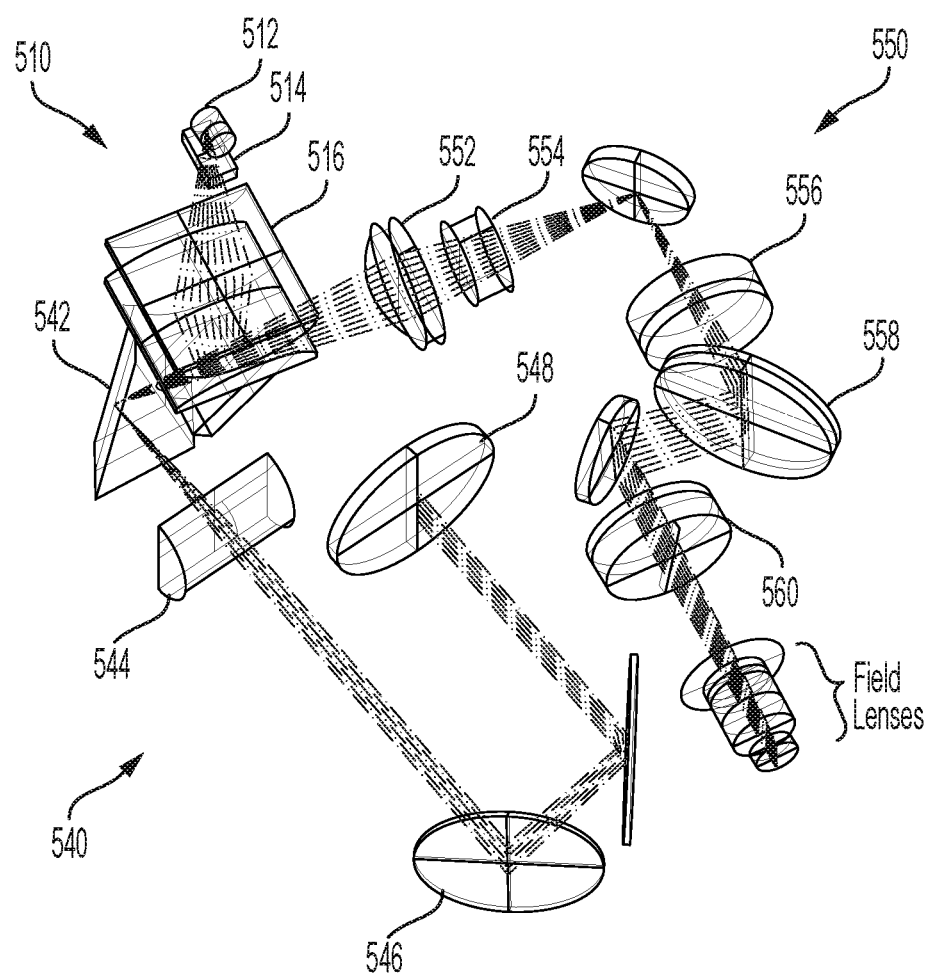
FIG. 5H is a perspective view of the source, reference, and detection components shown in FIGS. 5A and 5E-5G, according to some embodiments.

FIG. 5H is a perspective view of source components 510, reference components 540, and detection components 550 in an optically coupled configuration, according to some embodiments. In FIG. 5H, beam splitter 518 is shown configured to couple light from source components 510 to reference components 540 and provide light received from reference components 540 to detection components 550.

Figure 5I:
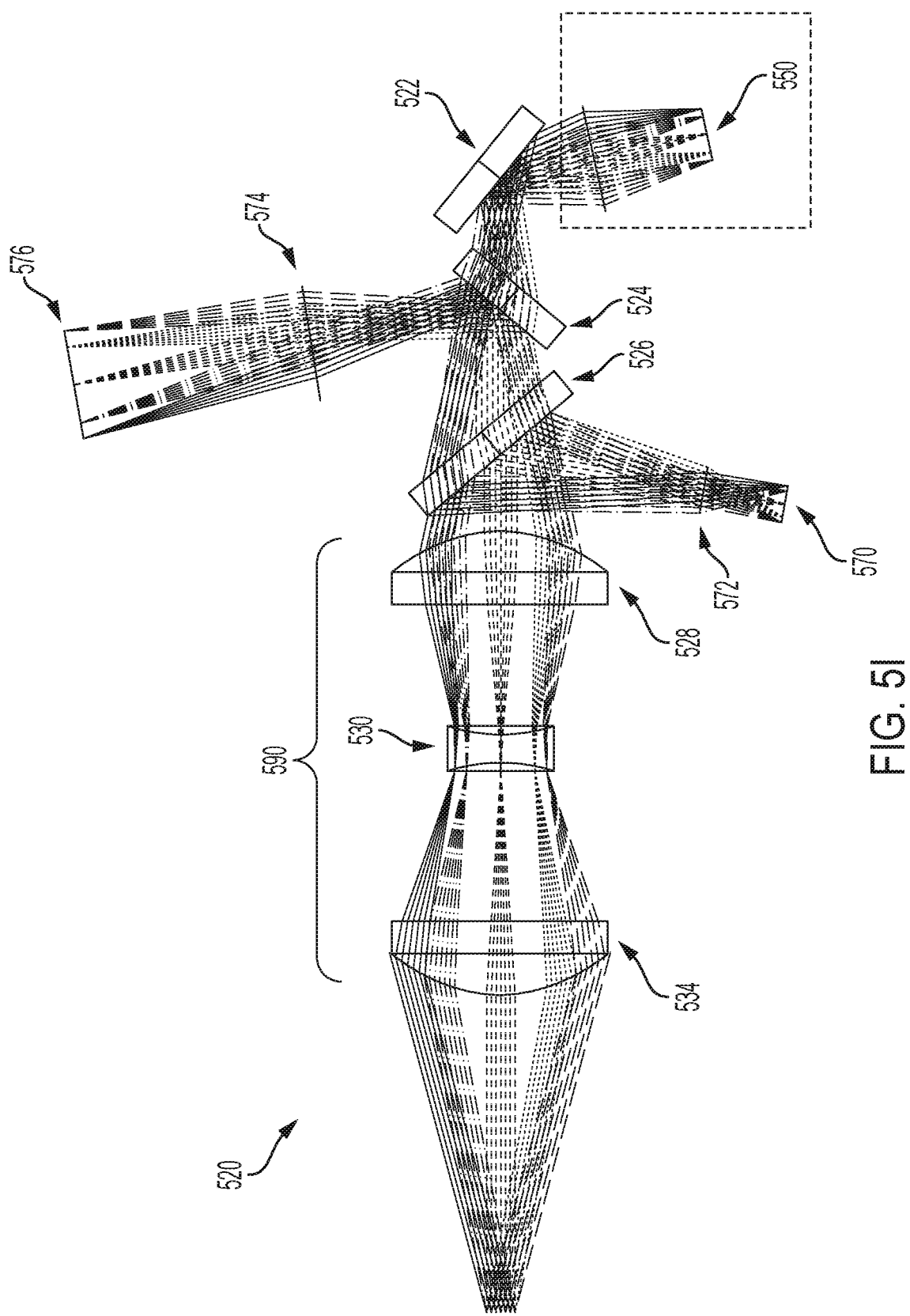
FIG. 5I is a perspective view of the sample components of FIGS. 5B-5D coupled to an infrared (IR) camera and fixation components, according to some embodiments.

FIG. 5I is a perspective view of sample components 520 coupled to detection components 550, IR camera 570, and fixation components, including focusing lens 574 and fixation display 576, according to some embodiments. As shown in FIG. 5I, lenses 528, 530, and 534 may be configured as pupil relay components 590. In some embodiments, biconcave lens 530 may be configured to provide a negative focal length. In some embodiments, the pupil relay components may provide comparable spreads of spectra and spatial and/or reduce spatial spread. In one example, the pupil relay components may reduce spatial spread by a factor of 5.

As shown in FIG. 5I, at least some IR light received from a subject's eye via lenses 534, 530, and 528 may reflect off IR fundus dichroic 526 and be provided by focusing lens 527 to IR camera 570. In some embodiments, focusing lens 572 may be configured with ring illumination. For example, focusing lens 572 may include a ring of IR light emitting diodes (LEDs). In some embodiments, IR LEDs may have a wavelength of 910 nm. In some embodiments, IR LEDs may have a wavelength of 940 nm. Also shown in FIG. 5I, at least some visible light received from the subject's eye may reflect off fixation dichroic 524 and be provided by focusing lens 574 to fixation display 576. As shown in FIG. 5I, some visible and IR light is also provided to detection components 550 via scanning mirror 522 for OCT imaging. In FIG. 5I, lenses 528, 530, and 534 provide a shared optical path for OCT and IR imaging.

Figure 6A:
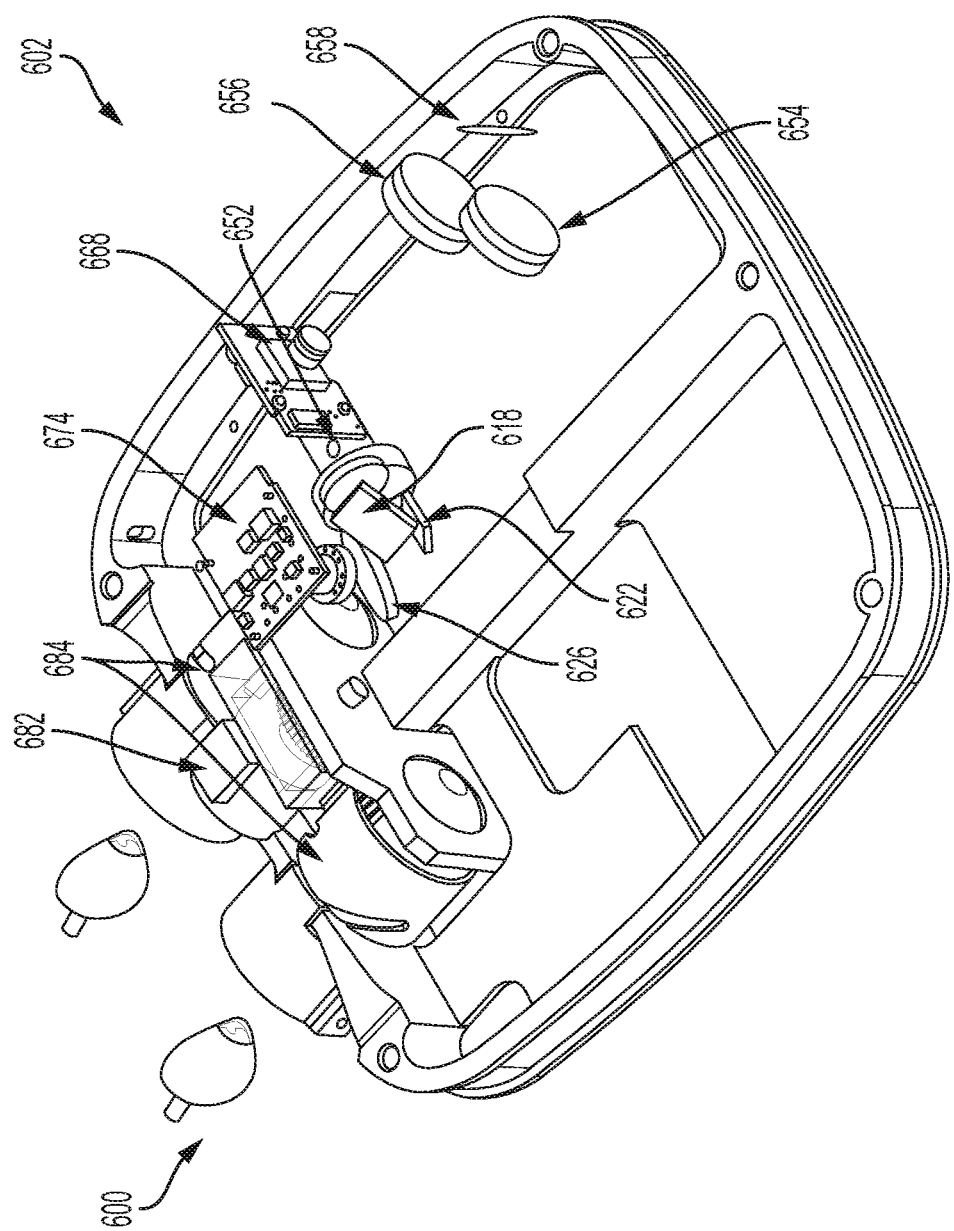
FIG. 6A is a top perspective view of an alternative embodiment of a multimodal imaging apparatus comprising a combination Optical Coherence Tomography (OCT) and infrared (IR) imaging device, according to some embodiments.

FIG. 6A is a top perspective view of an alternative embodiment of a multimodal imaging apparatus 600 comprising a combination Optical Coherence Tomography (OCT) and infrared (IR) imaging device, according to some embodiments. In some embodiments, components of imaging apparatus 600 may be configured in the manner described in connection with FIGS. 4A-4C and 5A-5I. As shown in FIG. 6A, the imaging apparatus 600 includes OCT and IR components 602, including source components, sample components, reference components, and detection components. Of the sample components, beam splitter 618, scanning mirror 622, and IR fundus dichroic 626 are shown in FIG. 6A. In some embodiments, beam splitter 618 may be a plate beam splitter. Of the detection components, achromatic lenses 654 and 656, transmissive grating 658, and OCT camera 668 are shown in FIG. 6A. FIG. 6A also shows fixation display 674 and diopter components including diopter motors 682 and diopter mechanics 684. In some embodiments, OCT camera 668 may include an interferometer such as a Mach-Zehnder interferometer and/or a Michelson interferometer. In some embodiments, scanning mirror 622 may be actuated with one or more stepper motors, galvanometers, polygonal scanners, micro-electromechanical switch (MEMS) mirrors, and/or other moving mirror devices. As shown in FIG. 5A, cylindrical lenses 516 face opposite directions, with rounded surfaces facing one another.

FIG. 6B is a side perspective view of components 602 of imaging apparatus 600, according to some embodiments. FIG. 6B shows OCT and IR components 602, IR camera 664, and fixation components including fixation lenses 672 and fixation display 674. OCT and IR components 602 include source components, sample components, reference components, and detection components. Of the source components, light source 612 and beam splitter 618 are shown in FIG. 6B, where light source 612 may be a superluminescent diode. Of the sample components, scanning mirror 622, plano-convex lens 630, biconcave lens 632, and plano-convex lens 634 are shown in FIG. 6B. Lenses 630, 632, and 634 are diopter-adjustable components 690. In some embodiments, these lenses may be adjusted to compensate for subjects having different corrections, hyperopia or presbyopia. Of the detection components, transmissive grating 658 and OCT camera 668 are shown in FIG. 6B. FIG. 6B also shows motor and scanning window 651.

FIG. 6C is an exploded view of alternative components 602' that may be included in imaging apparatus 600, according to some embodiments. FIG. 6C shows light source 612 and collimating lenses 616 of source components 610, dispersion compensator 642, collimating lens 644, and reference surface 648 of reference components 640, and pickoff mirror 652, reflective grating 658', field lenses 666, and OCT camera 668 of detection components 650. In some embodiments, cylindrical lens 616, alone or in combination with a cylindrical or aspherical beam-spreader, may be configured to form light from light source 612 into an elongated line for scanning a subject's retina fundus. For example, when the light reaches the subject's retina fundus, the light may be focused in a first direction and elongated in a second direction perpendicular to the first direction.

FIG. 6C also shows pupil relay lenses 690a of sample components 620 and pupil relay lenses 690c of detection components 690c. In some embodiments, pupil relay lenses 690c may include a first lens disposed proximate beam splitter 618 and a second lens disposed proximate reflective grating 658', where the first lens has a smaller focal length than the second lens such that the second lens magnifies the interfered light from beam splitter 618, thereby reducing the angular range of the interfered light. In some embodiments, reflective grating 658' may be configured to reflect and diffract the interfered light, causing the different wavelengths of the light to propagate in different directions toward the second lens. In some embodiments, the direction of the spread of the different wavelengths may be perpendicular to the direction of the elongated axis of the light line. As shown in FIG. 6C, the second lens may focus the diffracted light on to pickoff mirror 652, which reflects the diffracted light towards OCT camera 668. In some embodiments, light reflected by pickoff mirror 652 may pass through cylindrical lens pair 666 toward OCT camera 668. In some embodiments, cylindrical lens pair 666 may be configured to flatten the light field and equalize the focal length between the light spread in the spectral direction due to reflective grating 658' and the light spread in the spatial direction of the line.

In some embodiments, OCT camera 668 may be configured to capture a two-dimensional image using the received light. In some embodiments, OCT camera 668 may be configured to spread light in two directions, with a first direction corresponding to the spectral spread of the light due to the reflective grating 658' and a second direction corresponding to the spatial spread of the light due to the cylindrical lens 616 used to form the light line. In some embodiments, OCT camera 668 may be configured to perform a Fourier transform along the spectral direction to obtain depth information. In some embodiments, a two-dimensional image of the portion of the subject's retina fundus illuminated by the line may be obtained corresponding to the elongated direction of the line and depth. In some embodiments, OCT camera 668 may be configured to capture a three-dimensional image. In some embodiments, OCT camera 668 may be configured to capture multiple images while components 602' scan the line across the subject's retina fundus. In some embodiments, each image acquired may correspond to a slice of the retina fundus in a direction perpendicular to the elongated direction of the line and perpendicular to the depth direction. In one example, 15-30 images may be captured, with each image corresponding to a different slice of the retina fundus.

In some embodiments, components 602' may be configured to scan the line across the subject's retina fundus to acquire the multiple images. In some embodiments, a scanning mirror (e.g., scanning mirror 622) may be positioned between the beam splitter 618 and the pupil relay lenses 690c. In some embodiments, the scanning mirror may be attached to a stepper motor (e.g., motor and scanning window 651) configured to rotate the scanning mirror such that the line illuminates different slices of the subject's retina fundus at different orientations of the scanning mirror. In other embodiments, no moving parts may be used to scan the line across the eye. In one example, a fixation display may include a moving fixator object such that scanning may be performed as the subject's eyes follow the fixator object.

Figure 7A:
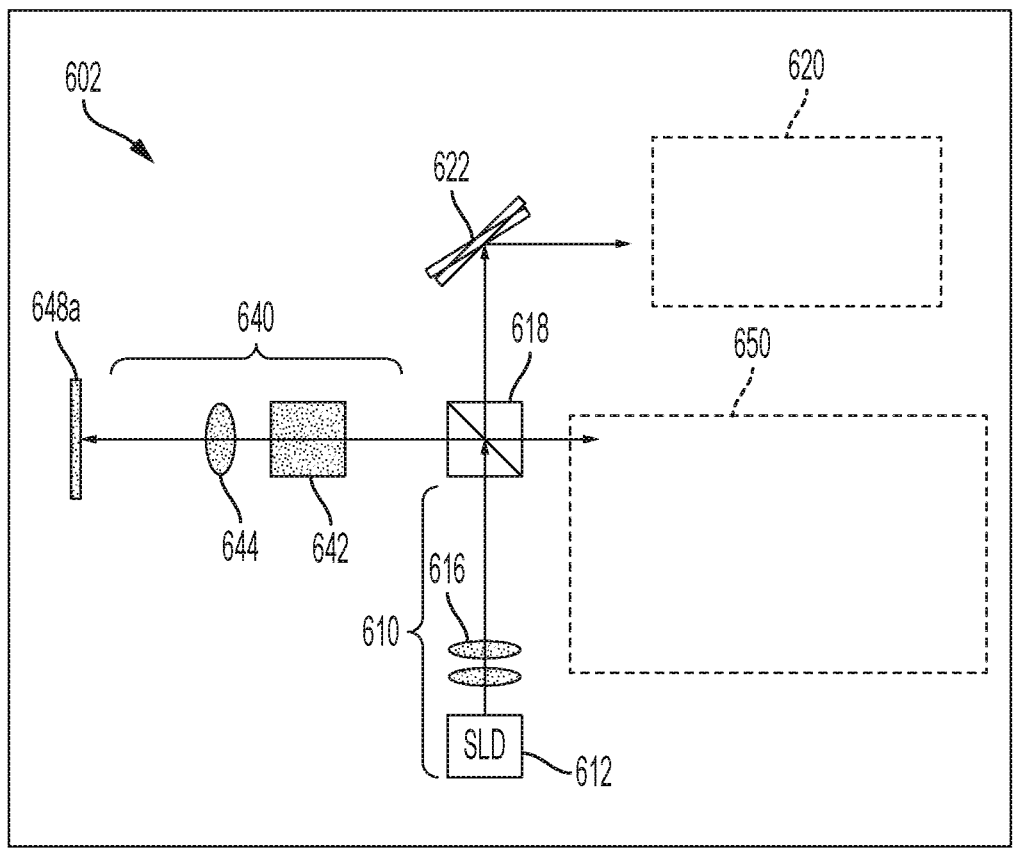
FIG. 7A is a block diagram illustrating components of the OCT and IR imaging device of FIGS. 6A-6B, according to some embodiments.

FIG. 7A is a block diagram illustrating OCT components 602 of imaging apparatus 600, according to some embodiments. As shown in FIG. 7A, OCT components 602 include source components 610, sample components 620 (shown in greater detail in FIGS. 8 and 11A), reference components 640, and detection components 650 (shown in greater detail in FIG. 10). Source components 610 include light source 612, which is shown as a super-luminescent diode, collimating lenses 616, and beam splitter 618. In some embodiments, collimating lenses 616 may include cylindrical collimating lenses and/or aspherical lenses. In FIG. 6, beam splitter 618 is configured to split light from light source 612 between sample components 620 and reference components 640 and to direct reflected light from sample components 620 and reference components 640 to detection components 650. Scanning mirror 622 of sample components 620 is also shown in FIG. 6B. Reference components 640 include dispersion compensator 642, collimating lens 644, which may be a cylindrical collimating lens in some embodiments, and reference surface 648a, which is shown as a single mirror. In some embodiments, reference surface 648a may include a diffuse reflector configured to reflect similarly to the human eye, as each point of reflection acts as a point source.

Figure 7B:
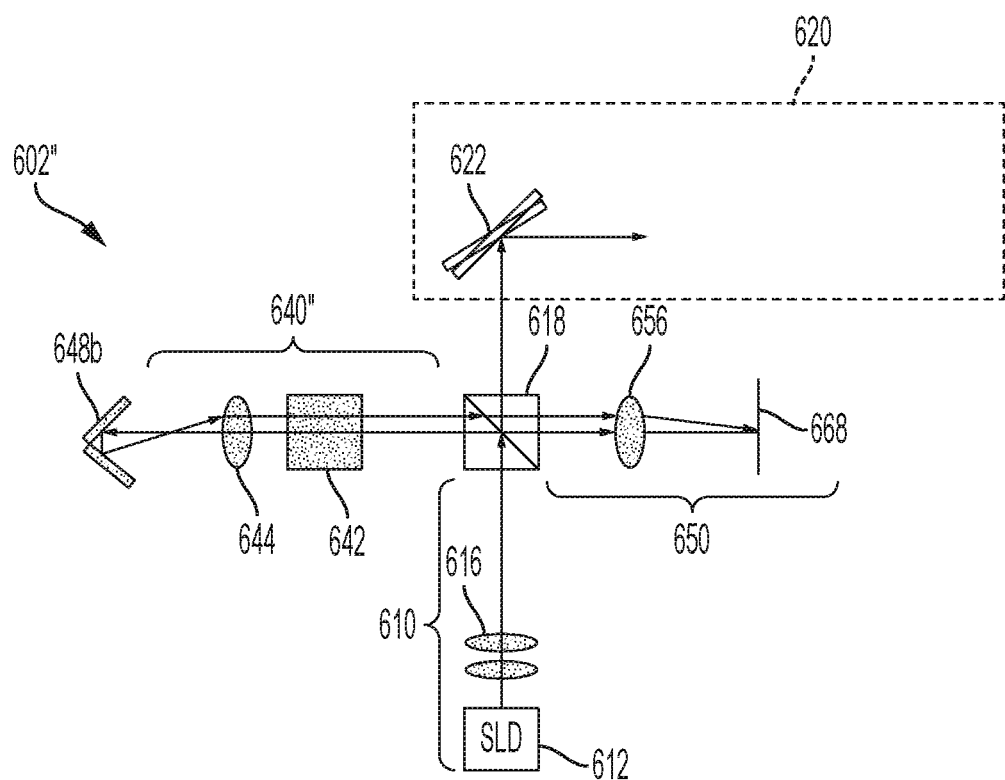
FIG. 7B is a block diagram illustrating alternative components that may be included in the OCT and IR imaging device of FIGS. 6A-6B, according to some embodiments.

FIG. 7B is a block diagram illustrating alternative components 602" that may be included in the OCT and IR imaging device of FIGS. 6A-6B, according to some embodiments. In some embodiments, components 602" may be configured to perform off-axis scanning of a subject's retina fundus. For example, in some embodiments, fold mirrors of reference surface 648b may be oriented off-axis such that multiple reflections so as to provide reflected light along multiple paths to detection components 650. As shown in FIG. 7B, components 602" may be configured in the same manner as components 602, except that reference surface 648b of reference components 640" includes a pair of fold mirrors. Reference surface 648b is shown reflecting light along multiple paths to detection components 650, with at least one of the paths being spatially offset from light received via sample components 620. FIG. 7B further illustrates achromatic lens 556 and OCT camera 668 of detection components 650.

In some embodiments, off-axis illumination may provide a means to remove DC and/or autocorrelation components that would otherwise interfere with OCT imaging. In some embodiments, off-axis illumination may allow for recovery of complex spectra, thereby enabling complex analytic signal recovery for full range imaging. In some embodiments, increasing range of imaging may reduce imaging speed (including sampling fewer spectral signals, and vice versa.

In some embodiments, a relative orientation angle of an illuminated line received by a camera may modulate the spatial direction of the light. In some embodiments, the cross-correlation modulation can be represented as:

$$I_\alpha(k, x) = I_{cc}(k, x)e^{-j\alpha x q} + I_{DC}(k, x) + I_{AC}(k, x)$$

$$FT_x[I_\alpha(k, x)] = I_{cc}(k, \tilde{q} - \alpha) + I_{DC}(k, \tilde{q}) + I_{AC}(k, q)$$

In some embodiments, a may be set to an angle that provides a spatial frequency between 50% to 90% of the Nyquist rate (e.g., between 1 to 6 degrees). In some embodiments, oversampling by a factor of 1.2 or more in both directions may provide a better signal to noise ratio and improved demodulation. In some embodiments, pre-processing an OCT image may include cropping, subtracting mean spectrum (e.g., DC component), and/or employing one or more window functions. In some embodiments, processing an OCT image may include one or more Fast Fourier Transforms (FFTs, e.g., x-space FFTs), demodulation (e.g., shifting spatial frequencies of interest to baseband), and/or cropping DC and AC components of the received signal. In some embodiments, processing may further include applying an inverse-FF, and/or k-space resampling and Fast Fourier Transform.

FIG. 8 is a top view of sample components 620 and fixation components 670, according to some embodiments. As shown in FIG. 8, sample components 620 include scanning mirror 622, IR fundus dichroic 624, fixation dichroic 626, and objective lens 628, which may be an achromatic lens. Also shown in FIG. 8 are diopter adjustable components 680a, which include plano-convex lenses 630 and 634 and biconcave lens 632 shown in FIG. 6B, receiving light via scanning mirror 622. In some embodiments, diopter adjustable components 680a may be configured to accommodate diopter adjustment of up to +/−10 diopters. In some embodiments, diopter adjustable components 680a may be configured to avoid inducing excessive pupil de-space, which might interfere with image quality. For the IR funduscopy system, an imaging system that will look through a scanning window, to the image sensor and fixation target, is envisioned. In some embodiments, diopter adjustable components 680a may be configured to substantially reduce the effect of back-reflections from IR components and the subject's cornea. In some embodiments, diopter adjustable components 680a may be configured to eliminate or substantially reduce visibility of fluorescence from the subject's eye's crystal lens. In some embodiments, diopter adjustable components 680a may employ the Schweitzer technique.

As shown in FIG. 8, fixation components 670 include fixation dichroic 626 and fixation display 674. In some embodiments, fixation dichroic may be configured as a long-pass filter that reflects short wavelength (e.g., visible) light toward fixation display 674 via fixation lenses 672 and transmits long wavelength (e.g., IR) light. In some embodiments, fixation display 674 may be configured to display a visible fixation image. In some embodiments, fixation display 674 may be a color display configured to display the visible fixation image. In some embodiments, fixation display 674 may be a New Haven Display International model NHD 0.6-6464G display. In some embodiments, fixation display 674 may be a monochrome Sony IMX273 sensors having a resolution of 1440×1080 at 3.45 square microns. In some embodiments, fixation components 670 may include Sony IMX273 sensors having a resolution of 1440×1080 at 3.45 square microns. In some embodiments, a short dimension of fixation display 674 (e.g., vertical for aspect ratios of 4:3, 16:9, or 16:10) map(s) to a 30 degree field-of-view looking into the eye. In some embodiments, fixation display 674 may be substantially free from vignetting over a full circular 30 degree diameter field-of-view, or other field-of-view as appropriate. In some embodiments, fixation display 674 (e.g., a square array) maps to a 20 degree by 20 degree field-of-view as seen by the eye.

In some embodiments, some IR light may also be transmitted through to detection components 650. In some embodiments, fixation lenses 672 may be adjustable to provide diopter compensation. IR fundus dichroic 624 is shown as a short-pass filter that reflects long wavelength (e.g., IR) light toward IR detection components (shown in FIGS. 9A and 9D-9E) and transmits short wavelength (e.g., visible) light to detection components 650.

Figure 9A:
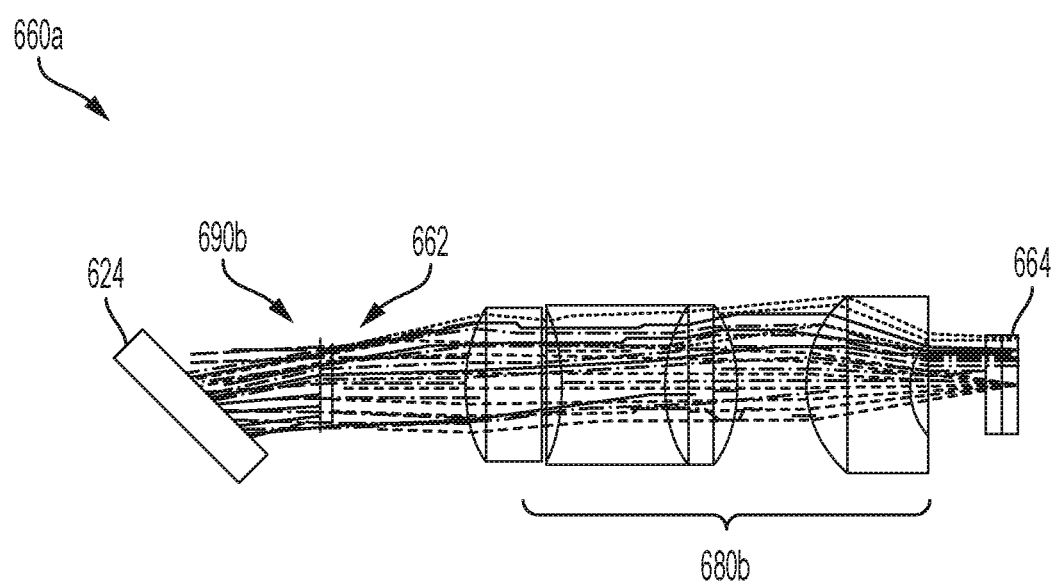
FIG. 9A is a side view of IR detection components that may be coupled to the sample components of FIG. 8, according to some embodiments.
Figure 9B:
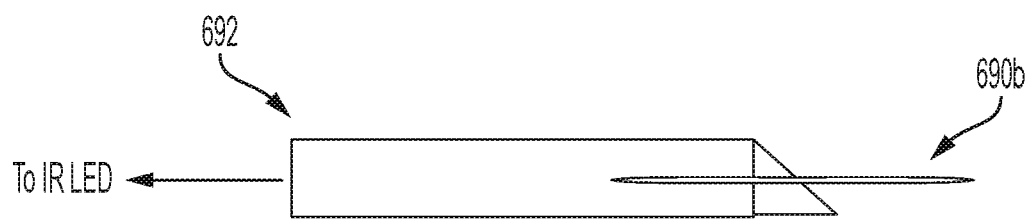
FIG. 9B is a side view of the pupil relay shown in FIG. 9A, according to some embodiments.
Figure 9C:
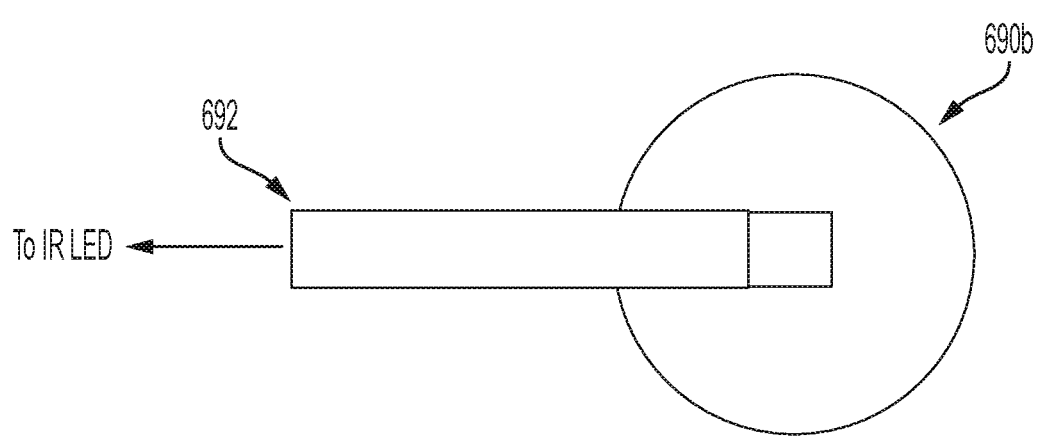
FIG. 9C is a top view of the pupil relay of FIGS. 9A-9B, according to some embodiments.

FIG. 9A is a side view of IR detection components 660a that may be coupled to sample components 660a, according to some embodiments. As shown in FIG. 9A, IR detection components 660a include IR fundus dichroic 624, IR pupil relay 690b, astigmatic corrector 662, diopter adjustable lenses 680c, and IR camera 664. FIG. 9B is a side view of pupil relay 690b and fiber 692, according to some embodiments. FIG. 9C is a top view of pupil relay 690b and fiber 692, according to some embodiments.

Figure 9D:
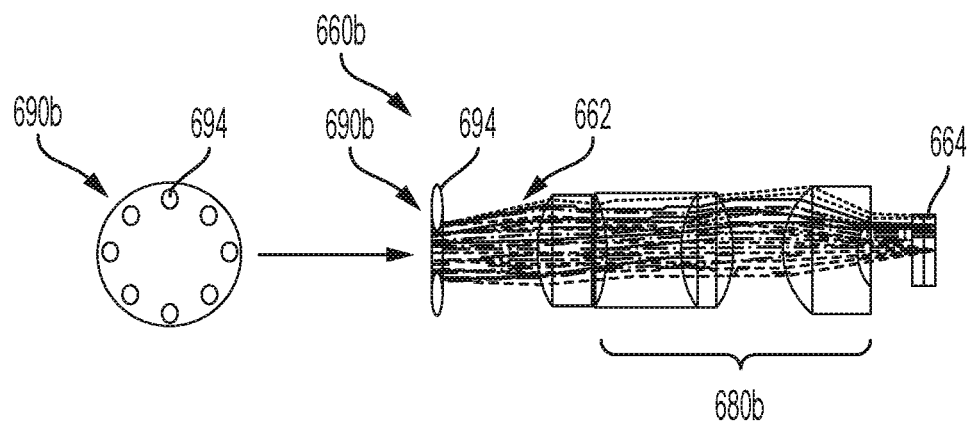
FIG. 9D is a side view of alternative IR detection components that may be coupled to the sample components of FIG. 8, according to some embodiments.

FIG. 9D is a side view of alternative IR detection components 660b that may be coupled to sample components 620, according to some embodiments. Like IR detection components 660a, IR detection components 660b include astigmatic corrector 662, diopter adjustable lenses 680b, and IR camera 664. IR detection components 660b further include pupil relay 690b, which includes a plurality of off-axis LEDs 694. In some embodiments, pupil relay 690b may further include a holographic plate to place a low-intensity spot on the reflective part of the front objective lens, thereby reducing coupling between the reflective part and the imaging plane.

Figure 9E:
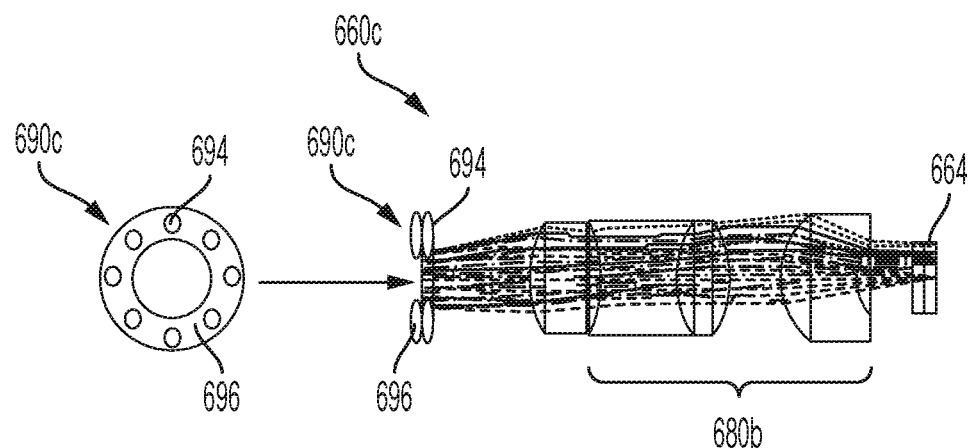
FIG. 9E is a side view of further alternative IR detection components that may be coupled to the sample components of FIG. 8, according to some embodiments.

FIG. 9E is a side view of further alternative IR detection components 660c that may be coupled to sample components 620, according to some embodiments. Like IR detection components 660a and 660b, IR detection components 660c include astigmatic corrector 662, diopter adjustable lenses 680b, and IR camera 664. IR detection components 660c further include pupil relay 690c, which includes a plurality of off-axis LEDs 694 and a diffractive plate 696. In some embodiments, diffractive plate 696 may be configured to place a low-intensity spot on the reflective part of the front objective lens, thereby reducing coupling between the reflective part and the imaging plane.

Figure 10:
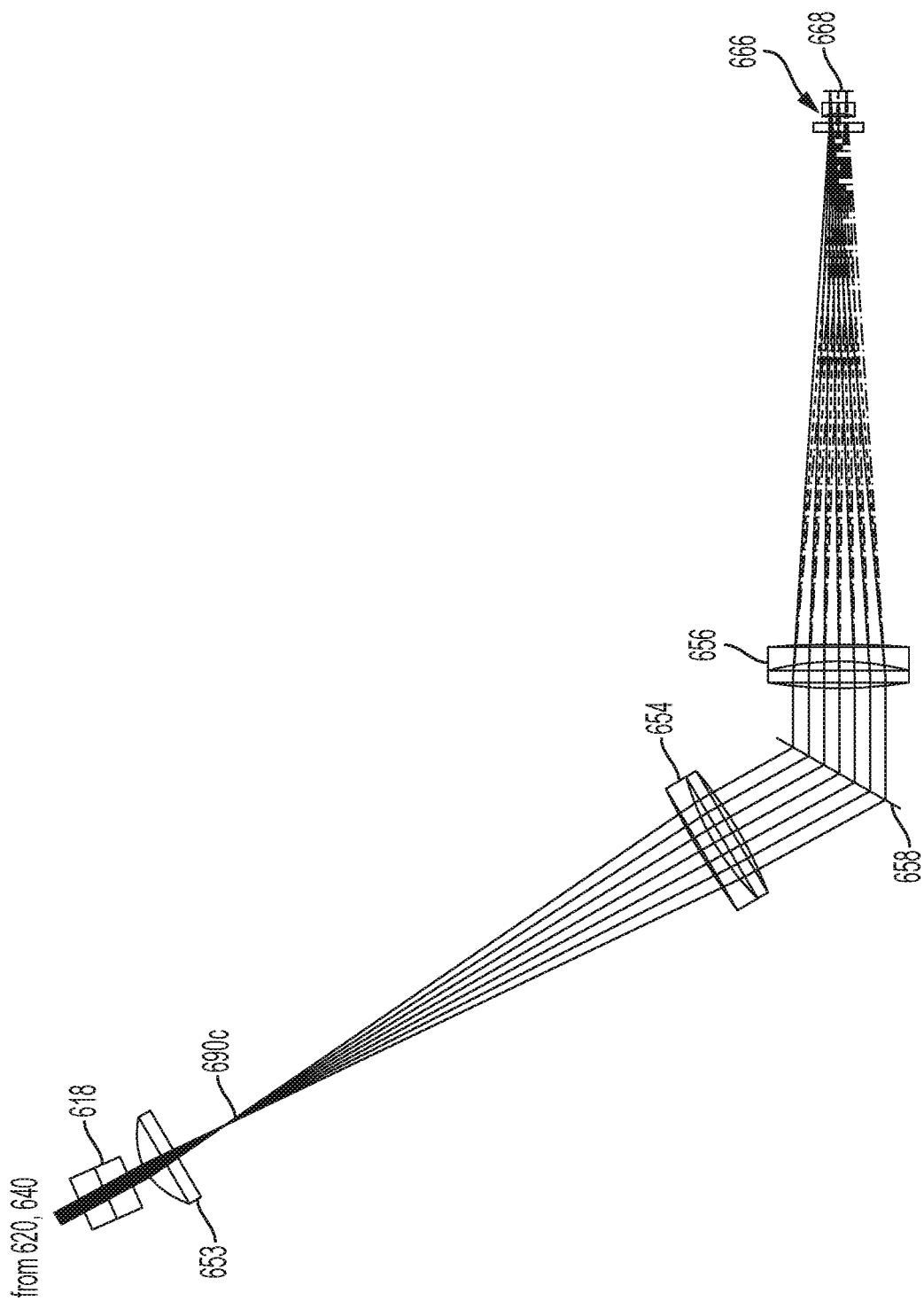
FIG. 10 is a top view of detection components of the OCT imaging device of FIGS. 6A-6B, according to some embodiments.

FIG. 10 is a top view of detection components 650 coupled to beam splitter 618, according to some embodiments. As shown in FIG. 10, detection components 650 include aspherical lens 653, achromatic lenses 654 and 656, transmissive grating 658, field lenses 666, and OCT camera 668. In some embodiments, transmissive grating 658 may be configured as described for transmissive grating 558. In some embodiments, transmissive grating 558 may improve the spectral signal to noise ratio for light received by OCT camera 568. In some embodiments, transmissive grating 558 may be configured provide light at normal incidence to OCT camera 568. In some embodiments, transmissive grating 558 may enhance the noise performance of the transfer function of OCT camera 568. In some embodiments, aspherical lens 653 may be configured to provide a pupil relay 690c before achromatic lens 654. In some embodiments, aspherical lens 653 may be configured to reduce spatial spread by 5 times. In some embodiments, achromatic lens 654 may be configured to collimate received light toward transmissive grating 658. In some embodiments, achromatic lens 656 may be configured to focus light on OCT camera 668. In some embodiments, field lenses 666 may be configured to flatten the field, adjust the chief ray angle, and achieve diverging chief rays.

Figure 11A:
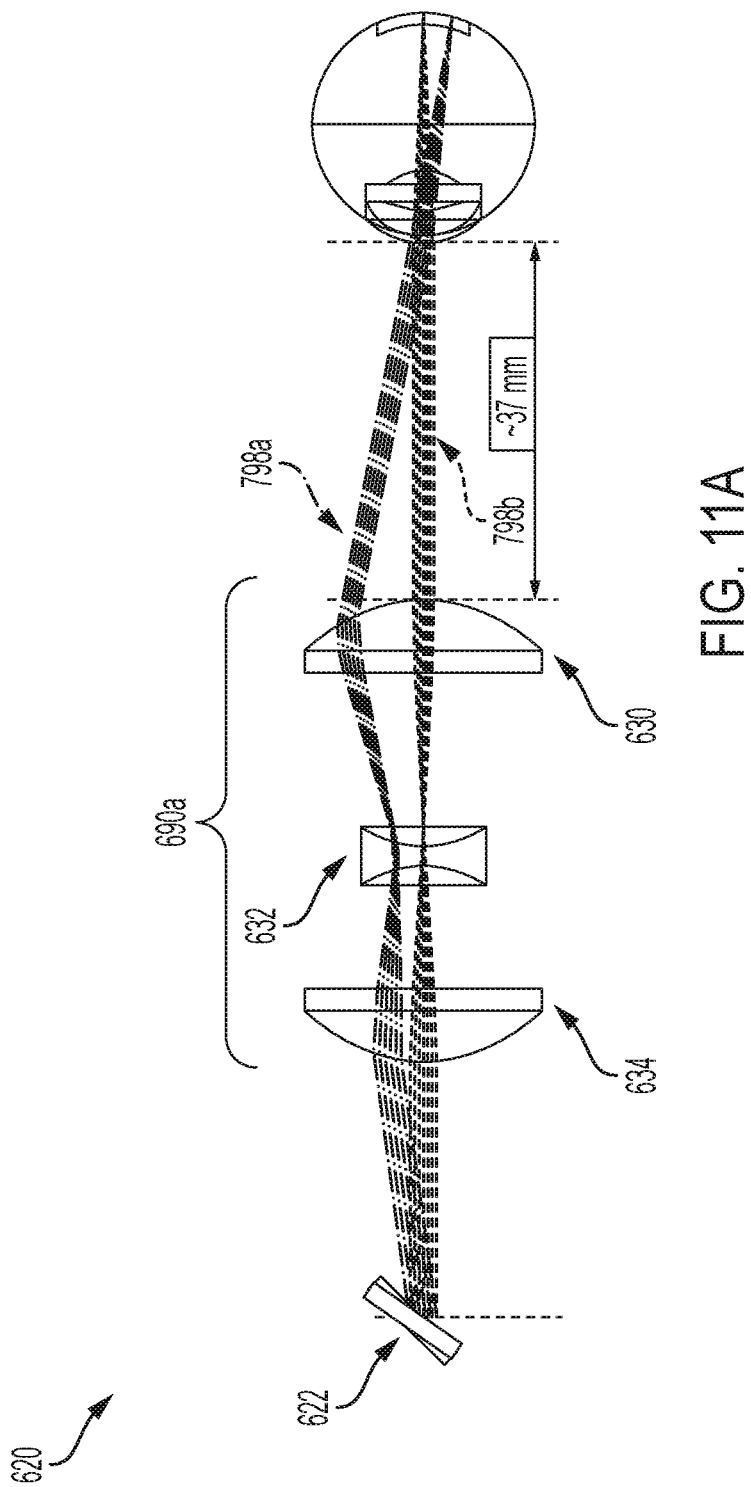
FIG. 11A is a side view of the sample components of FIG. 8 illustrating scanning paths of the OCT and IR imaging device, according to some embodiments.

FIG. 11A is a side view of sample components 620 illustrating scanning paths of the OCT and IR imaging device, according to some embodiments. Horizontal scanning path 798a and vertical scanning path 798b are shown passing through lenses 630, 632, and 634 from scanning mirror 622.

Figure 11B:
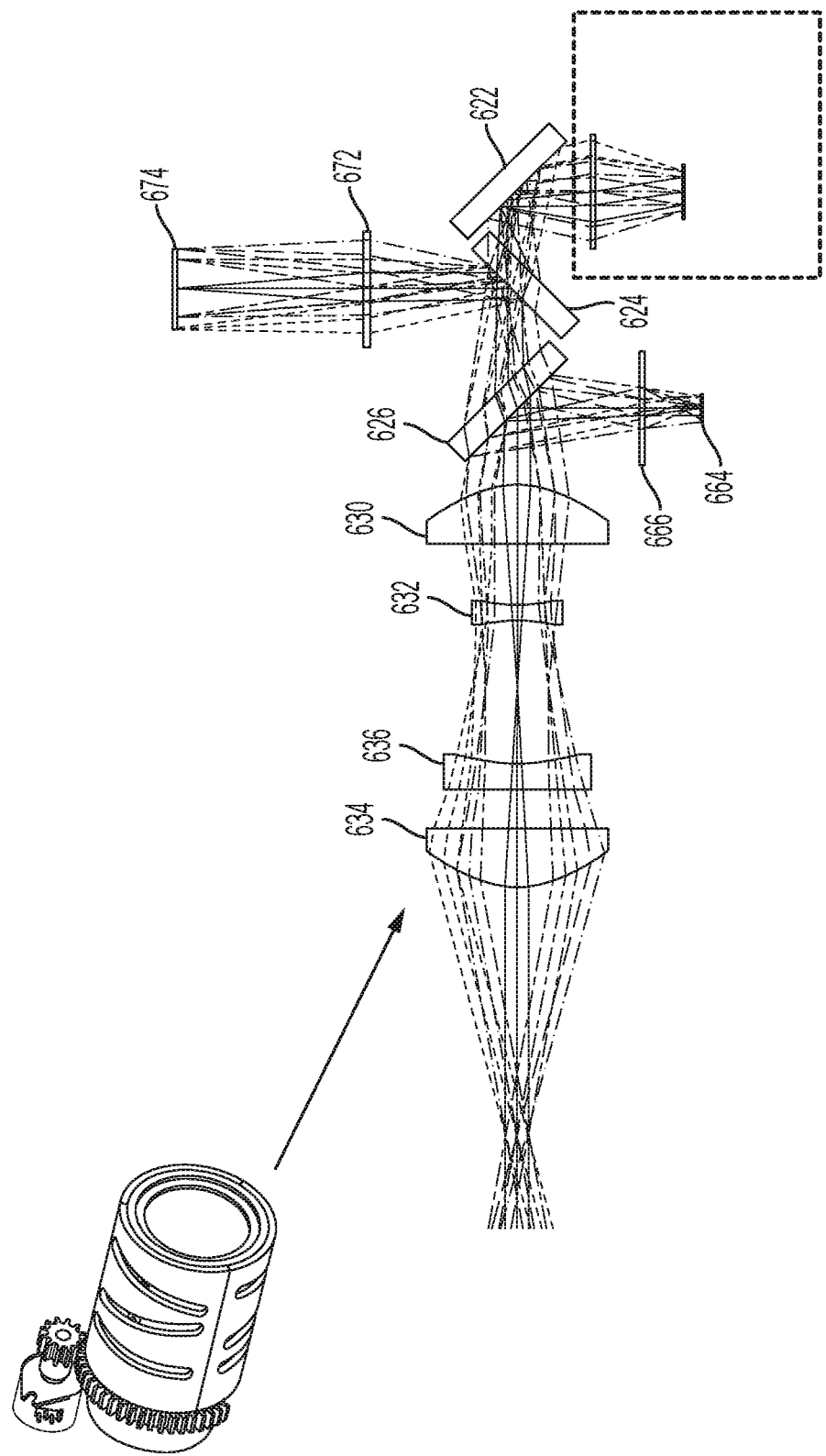
FIG. 11B is a side view of the sample components shown in FIG. 11A including diopter compensation components, according to some embodiments.

FIG. 11B is a side view of sample components 620 including scanning mirror 622, fixation dichroic 624, IR fundus dichroic 626, and diopter adjustable lenses 630, 632, 634, and 636. In some embodiments, lenses 630, 632, 634, and/or 636 may be movable along the optical axis from scanning mirror 622 to the subject's eye to provide diopter compensation. In some embodiments, IR camera 664 and/or lens 666 may include an IR LED, such as a 910 nm LED or a 940 nm LED.

It should be appreciated that, in some embodiments, imaging apparatuses described herein (e.g., in connection with FIGS. 4A-11B) may be configured to perform time domain OCT. In some embodiments, a scanning mirror of the imaging apparatus may be configured to scan the depth of a subject's retina fundus. In some embodiments, the scanning mirror may serve as reference surface 548 or 648 among reference components 540 or 640, respectively. In some embodiments, a piezoelectric actuator of the imaging apparatus may be configured to control scanning of the scanning mirror.

In some embodiments, imaging apparatuses described herein (e.g., in connection with FIGS. 4A-11B) may be configured to capture two images in rapid succession to form a single depth image. In some embodiments, two images taken in rapid succession are taken close enough together in time to ensure no eye movement occurs between the two images. The inventors recognized that the frame rate of a conventional camera may be too slow to guarantee this. For example, to keep the price of the imaging apparatus low, a camera with a frame rate that is less than 276 frames per second may be used. In some embodiments, such a camera may be configured to operate at a much higher frame rate by limiting the imaging field-of-view. To overcome the drawbacks associated with using a slow frame rate, the light source of the imaging apparatus may be pulsed towards the end of one frame and at the beginning of the next frame, as described herein including with reference to FIG. 7.

Figure 12:
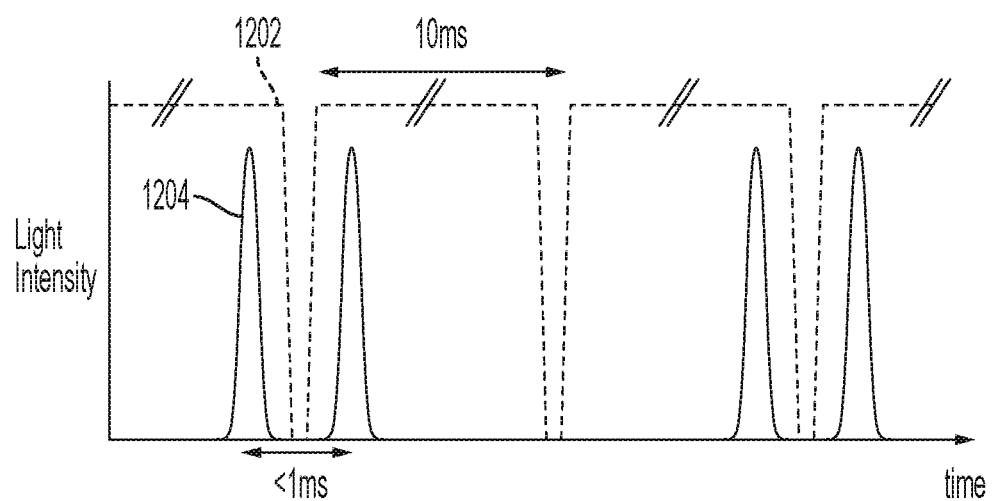
FIG. 12 is a graph of light intensity over time for a light source of an imaging apparatus, as the light source pulses in synchronization with one or more cameras of the imaging apparatus, according to some embodiments.

FIG. 12 is a graph of light intensity over time for a light source of an imaging apparatus (e.g., of FIGS. 4A-11B), as the light source pulses in synchronization with one or more cameras of the imaging apparatus, according to some embodiments. In FIG. 12, dashed lines 1202 represent the duration of an imaging frame and solid lines 1204 represent the duration of light pulses. By synchronizing the light pulses with the frame rate of the image sensor, two images of the fundus taken less than 1 ms apart may be obtained using an image sensor with a much longer frame period (e.g., 10 ms).

Figure 13:
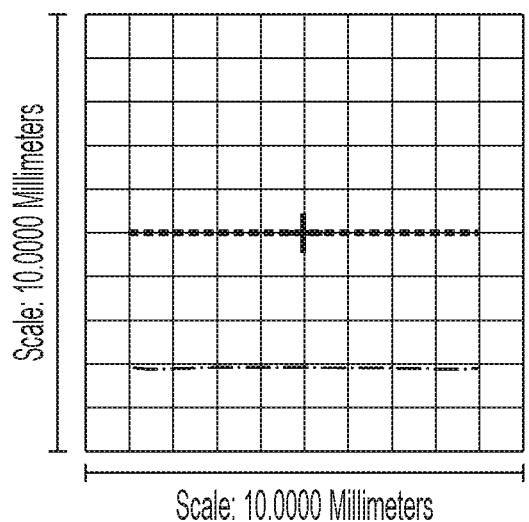
FIG. 13 is a graph illustrating retinal spot diagrams for pupil relay components that may be included in an imaging apparatus, according to some embodiments.
Figure 20A:
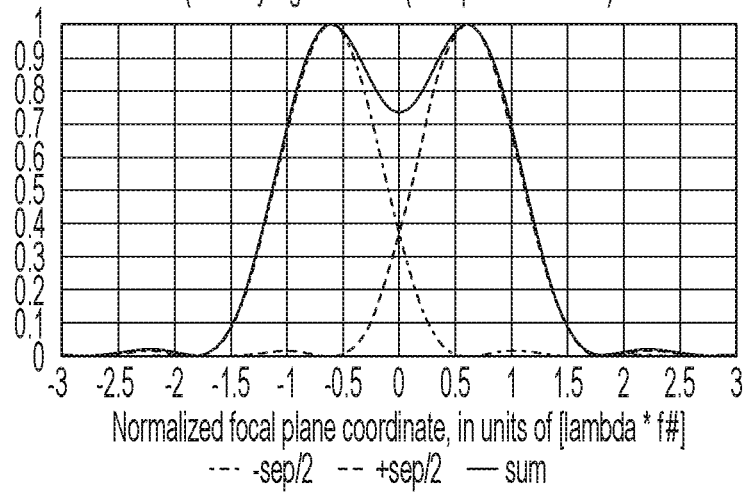
FIG. 20A is a graph of optical patterns generated using two airy disks separated by a distance of 1.22 wavelengths, according to some embodiments.
Figure 20B:
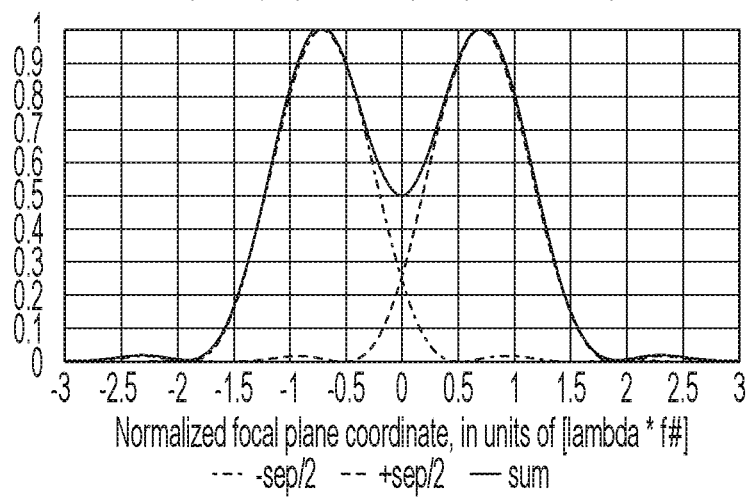
FIG. 20B is a graph of optical patterns generated using two airy disks separated by a distance of 1.41 wavelengths, according to some embodiments.
Figure 20C:
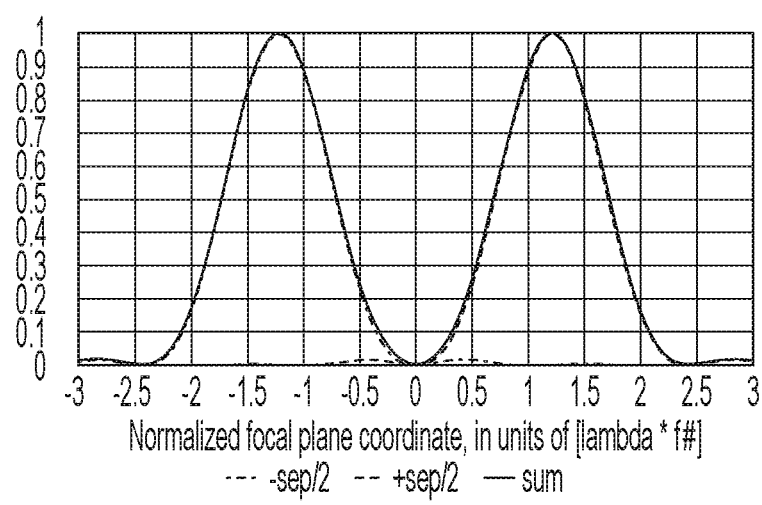
FIG. 20C is a graph of optical patterns generated using two airy disks separated by a distance of 2.44 wavelengths, according to some embodiments.

FIG. 13 is a graph illustrating retinal spot diagrams for pupil relay components that may be included in an imaging apparatus (e.g., of FIGS. 4A-11B), according to some embodiments. In FIG. 13, the scale is 1 mm per grid, and a 30 mm diameter field-of-view corresponds to an 8.5 mm diameter disk. In some embodiments, pupil relay components described herein may be configured to provide a 50% peak reduction. In some embodiments, pupil relay components may include two airy disks separated at a distance of 1.41 wavelengths as the baseline interpretation of resolution, rather than the twice-Rayleigh criterion of 2.44 wavelengths. In one example, the nominal IR imaging wavelength is 910 nm, the pupil diameter is 2.5 mm, and the in-air ocular focal length is 22.2 mm, which provides a diffraction-limited resolution of 11 um. In another example, the center white light wavelength is 550 nm, which results in a decreased resolution to 7 um. A desired imaging of an 8.5 mm disk on the retina fundus onto a 1080-row camera results in a Nyquist limit of 1 cycle per 16 um, resulting in an imaging quality goal of 50% MTF. Exemplary optical patterns for various airy disk separations are illustrated in FIGS. 20A-20C. FIG. 20A is a graph of optical patterns generated using two airy disks separated by a distance of 1.22 wavelengths, according to some embodiments. FIG. 20B is a graph of optical patterns generated using two airy disks separated by a distance of 1.41 wavelengths, according to some embodiments. FIG. 20C is a graph of optical patterns generated using two airy disks separated by a distance of 2.44 wavelengths, according to some embodiments.

In some embodiments, a scanning mirror may be disposed at a position conjugate to a pupil of the subject's eye's and configured to relay a collimated beam generated by the imaging apparatus to a collimated beam at the subject's pupil. In one example, the scanning mirror may be configured to produce a first surface reflection at an incidence angle of 45+/−6 degrees and a scanning thickness of 3 mm. In some embodiments, the scanning mirror may be configured as a variable angle window.

Figure 14A:
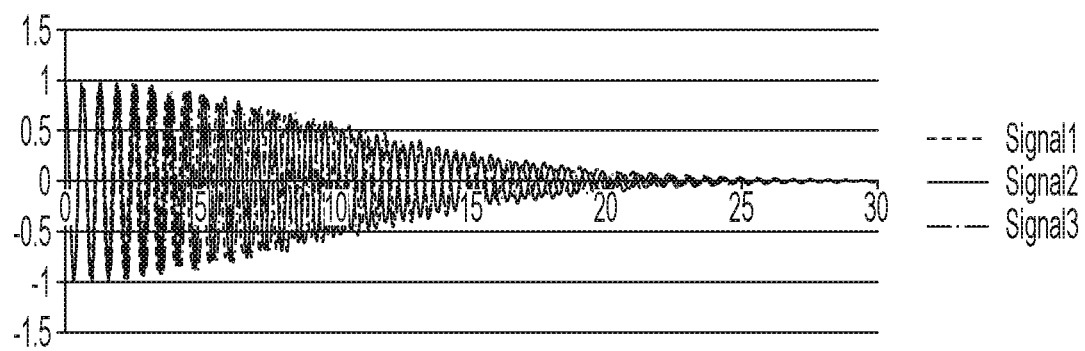
FIG. 14A illustrates individual interference amplitudes for three different light sources in an optical coherence tomography (OCT) device, according to some embodiments.
Figure 14B:
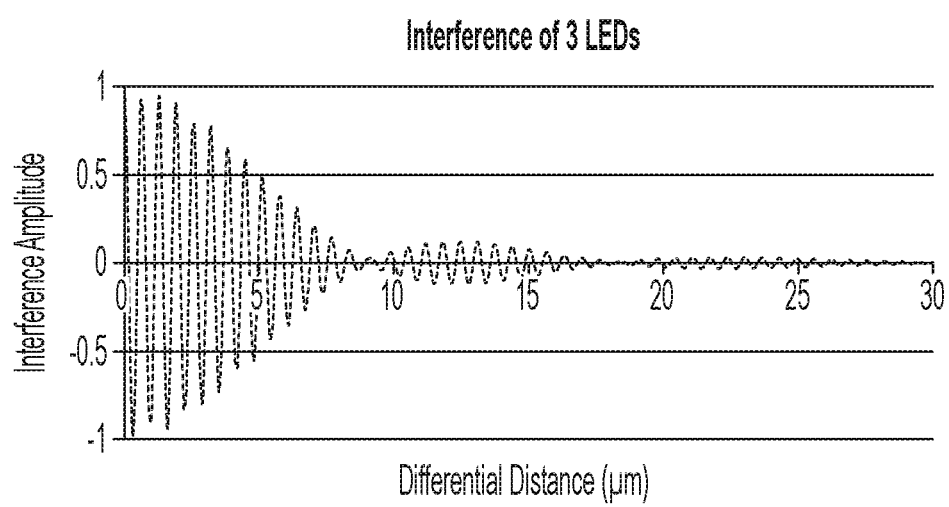
FIG. 14B illustrates the combined interference amplitude for the three different light sources in an optical coherence tomography device, according to some embodiments.

FIG. 14A illustrates the combined interference amplitude for three different light sources that may be included in an OCT imaging device (e.g., of FIGS. 4A-11B). FIG. 14B illustrates individual interference amplitudes for three different diode lasers that may be included in an OCT imaging device (e.g., of FIGS. 4A-11B). As shown in FIG. 14B, the depth resolution for the three combined laser diodes is greater than the depth resolution of any one of the individual laser diodes.

Figure 15A:
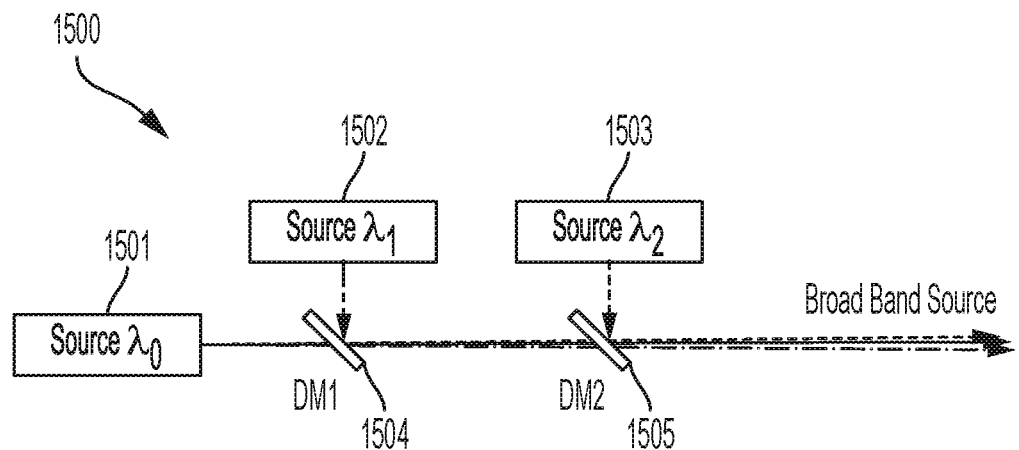
FIG. 15A illustrates a light emitter with multiple light sources for use in an optical coherence tomography device, according to some embodiment.
Figure 15B:
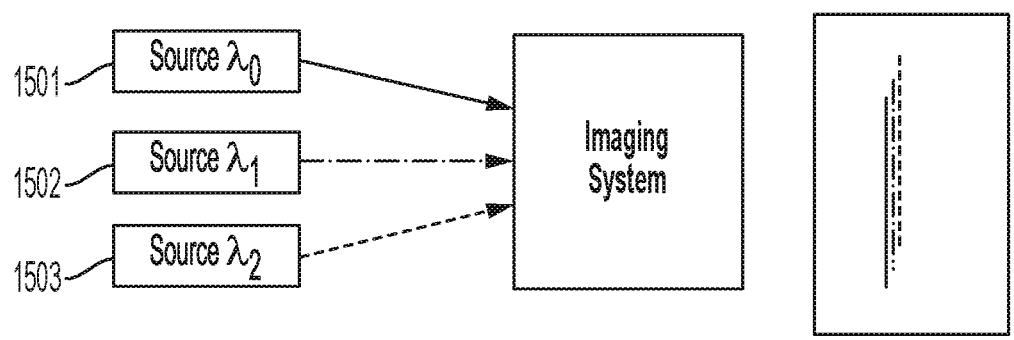
FIG. 15B illustrates a light emitter with multiple light sources that emit lines of light for use in an optical coherence tomography device, according to some embodiment.

FIG. 15A illustrates one possible technique for combining multiple diode lasers to form a broadband emitter 1501. The broadband emitter 1501 includes a first diode laser 1501, a second diode laser 1502, and a third diode laser 1503. The first diode laser 1501 emits light of a first wavelength that is greater than the wavelength of the light emitted by the second diode laser 1502, which itself is greater than the wavelength of the light emitted by the third diode laser 1503. The light from the first diode laser 1501 is combined with the light from the second diode laser 1502 at a first dichroic mirror 1504. The light from the first diode laser 1501 and the light from the second diode laser 1502 are combined with light from the third diode laser 1503 at a second dichroic mirror 1505. Thus, the resulting output from the second dichroic mirror 1505 is a broadband light that may be used in an imaging apparatus. FIG. 15B illustrates each of the laser diodes feeding into an imaging system.

In some embodiments, the laser wavelengths are not separated by more than 1.5 times the spectral width of the neighboring lasers. In one example, a 40 nm bandwidth light emitter may be created by having each of the three lasers have a 10 nm bandwidth with a 5 nm gap between the spectral peaks of neighboring lasers is 5 nm.

III. Fluorescence and/or White Light Imaging Techniques

The inventors have developed improved white light and fluorescence imaging techniques that may be implemented alone or in combination with a multi-modal imaging apparatus, as described herein. In some embodiments, one or more white light and/or fluorescence imaging devices may be included in one or both of the first and second housing sections of the apparatus. In some embodiments, a fluorescent imaging device and a white light imaging device are included in the same housing section such that one eye is imaged by both imaging devices over a short period of time (e.g., seconds). In some embodiments, devices described herein may be configured to capture white light and fluorescence images without the subject having to move or reorient the subject's eyes. According to various examples, white light and fluorescence imaging devices may be configured to capture the respective white light and fluorescence images over a period of less than 5 seconds, less than 3 seconds, and/or less than 1 second. Moreover, in embodiments in which imaging devices are included in two housing sections of the imaging apparatus, imaging components within each housing section may be configured to capture an image, simultaneously and/or over a short period of time as described above.

In some embodiments, white light imaging may be performed by illuminating the subject's retina fundus with light from a white light source (or a plurality of color LEDs) and sensing reflected light from the retina fundus using a white light camera. In one example, a plurality of color LEDs may illuminate the subject's retina fundus at different points in time and the camera may capture multiple images corresponding to the different color LEDs, and the images may be combined to create a color image of the subject's retina fundus. In some embodiments, fluorescence imaging may be performed by illuminating the subject's retina fundus with an excitation light source (e.g., one or more narrow-band LEDs) and sensing fluorescence light from the subject's retina fundus using a fluorescence sensor and/or camera. For example, a wavelength of the excitation light source may be selected to cause fluorescence in one or more molecules of interest in the subject's retina fundus, such that detection of the fluorescence light may indicate the location of the molecule(s) in an image. In accordance with various embodiments, fluorescence of a particular molecule may be determined based on a lifetime, intensity, spectrum, and/or other attribute of the detected light.

As described herein, an imaging apparatus may include fluorescence and white light imaging components configured to share at least some components such that the imaging components share at least a portion of an optical path. As a result, imaging apparatuses including such components may be more compact and less expensive to produce while providing high quality medical images. It should be appreciated that some embodiments may include only fluorescence imaging components or only white light imaging components, as techniques described herein may be implemented alone or in combination.

Figure 16A:
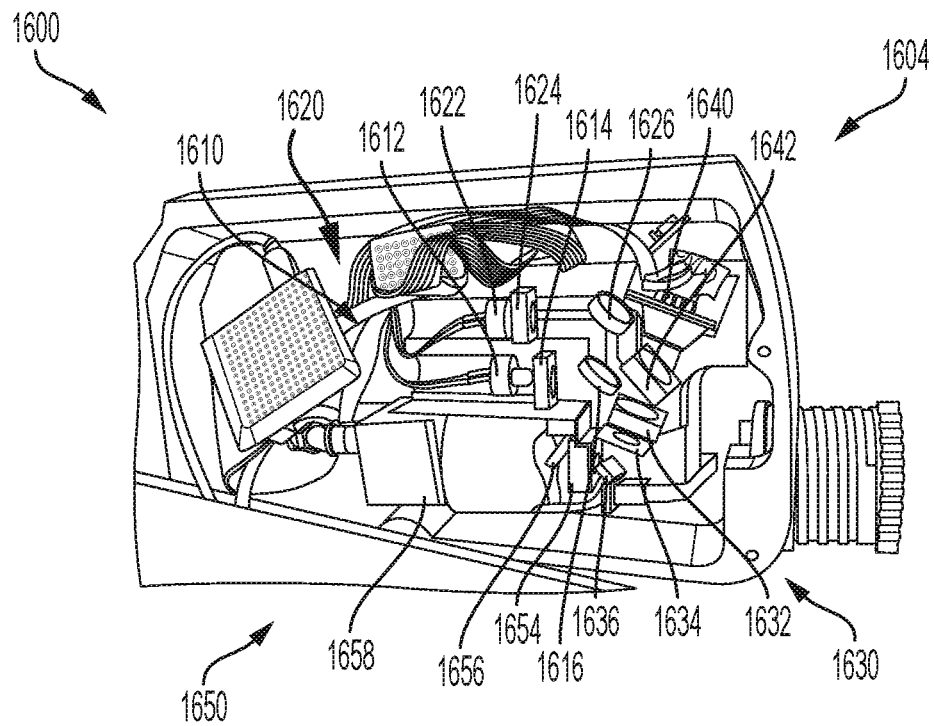
FIG. 16A is a top view of white light and fluorescence imaging components of a multimodal imaging apparatus, according to some embodiments.
Figure 16B:
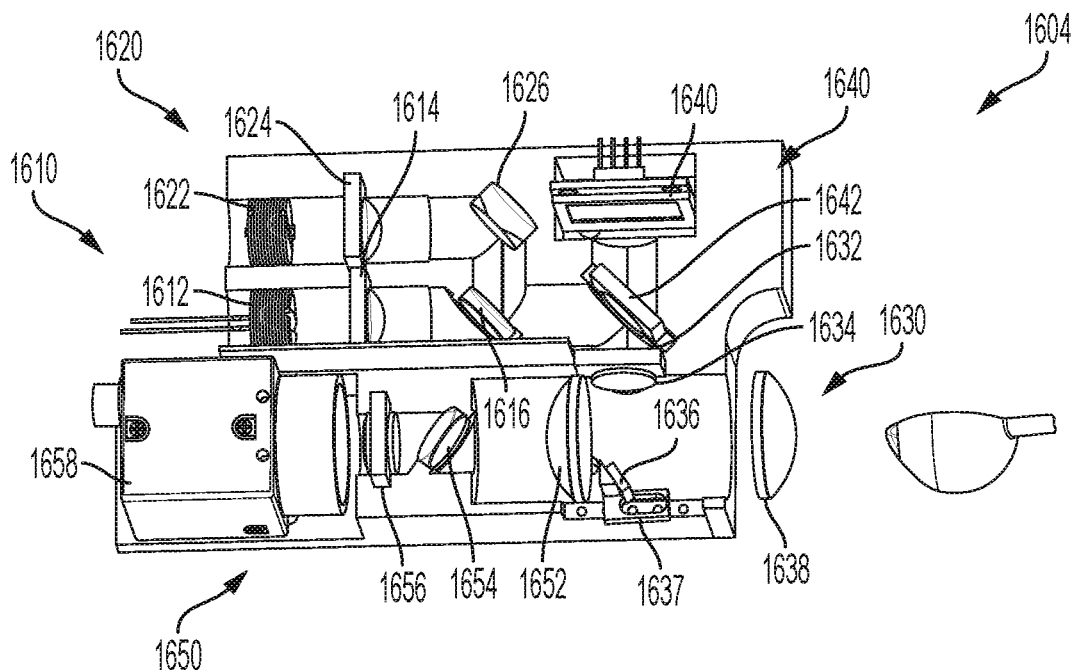
FIG. 16B is a top view of the white light and fluorescence imaging components of FIG. 16A with portions of the imaging apparatus removed, according to some embodiments.

FIGS. 16A-16B are top views of white light and fluorescence imaging components 1604 of multi-modal imaging apparatus 1600, according to some embodiments. FIG. 16A is a top view of multi-modal imaging apparatus 1600 with a partial view of white light and fluorescence imaging components 1604, and FIG. 16B is a top view of white light and fluorescence imaging components 1604 with portions of imaging apparatus 1600 removed. As shown in FIGS. 16A-16B, white light and fluorescence imaging components 1604 include white light source components 1610, excitation source components 1620, sample components 1630, fixation display 1640, and detection components 1650. In some embodiments, white light source components 1610 and excitation source components 1620 may be configured to illuminate the subject's retina fundus via sample components 1630 such that reflected and/or fluorescent light from the subject's retina fundus may be imaged using detection components 1650. In some embodiments, fixation display 1640 may be configured to provide a fixation object for the subject to focus on during imaging.

In some embodiments, white light source components 1610 may be configured to illuminate the subject's retina fundus such that light reflected and/or scattered by the retina fundus may be captured and imaged by detection components 1650, as described herein. As shown in FIGS. 16A-16B, white light source components 1610 include white light source 1612, collimating lens 1614, and laser dichroic 1616. In some embodiments, white light source 1612 may include a white LED. In some embodiments, white light source 1612 may include a plurality of color LEDs that combine to substantially cover the visible spectrum, thereby approximating a white light source. In some embodiments, white light source 1612 may include one or more blue or ultraviolet (UV) lasers.

In some embodiments, excitation source components 1620 may be configured to excite fluorescence in one or more molecules of interest in the subject's retina fundus, such that fluorescence light may be captured by detection components 1650. As shown in FIGS. 16A-16B, fluorescence source components include laser 1622, collimating lens 1624, and mirror 1626. In some embodiments, laser 1622 may be configured to generate light at one or more wavelengths corresponding to fluorescent characteristics of one or more respective molecules of interest in the subject's retina fundus. In some embodiments, such molecules may be naturally occurring in the retina fundus. In some embodiments, such molecules may be biomarkers configured for fluorescence imaging. For example, laser 1622 may be configured to generate excitation light having a wavelength between 405 nm and 450 nm. In some embodiments, laser 1622 may be configured to generate light having a bandwidth of 5-6 nm. It should be appreciated that some embodiments may include a plurality of lasers configured to generate light having different wavelengths.

As shown in FIGS. 16A-16B, white light source 1612 is configured to generate white light and transmit the white light via collimating lens 1614 to laser dichroic 1616. Laser 1622 is configured to generate excitation light and transmit the excitation light via collimating lens 1624 to mirror 1626, which reflects the excitation light to laser dichroic 1616. Laser dichroic 1616 may be configured to transmit white light and reflect excitation light such that the white and excitation light share an optical path to the subject's retina fundus. In some embodiments, laser dichroic 1616 may be configured as a long pass filter.

In some embodiments, fixation display 1640 may be configured to display a fixation object for the subject to focus on during imaging. Fixation display 1640 may be configured to provide fixation light to fixation dichroic 1642. In some embodiments, fixation dichroic 1642 may be configured to transmit fixation light and to reflect white light and excitation light such that the fixation light, white light, and excitation light all share an optical path from fixation dichroic 1642 to the subject's retina fundus.

In some embodiments, sample components 1630 may be configured to provide white light and excitation light to the subject's retina fundus and to provide reflected and/or fluorescent light from the subject's retina fundus to detection components 1650. As shown in FIGS. 16A-16B, sample components 1630 include achromatic lens 1632, iris 1634, illumination mirror 1636, and achromatic lens 1638. In some embodiments, achromatic lenses 1632 and 1638 may be configured to focus the white light, excitation light, and fixation light on the subject's retina fundus. In some embodiments, iris 1634 may be configured to scatter some of the white light, excitation light, and/or fixation light such that the light from the different sources focuses on respective portions of the subject's retina fundus. In some embodiments, illumination mirror 1636 may be adjustable, such as by moving positioning component 1637 in a direction parallel to the imaging axis. In some embodiments, achromatic lens 1638 may be further configured to provide reflected and/or fluorescent light from the subject's retina fundus to detection components 1650.

Detection components 1650 may be configured to focus and capture light from the subject's retina fundus to create an image using the received light. As shown in FIGS. 16A-16B, detection components 1650 include achromatic lens 1652, dichroic 1654, focusing lens 1656, and camera 1658. In some embodiments, achromatic lens 1652 and focusing lens 1656 may be configured to focus received light on camera 1658 such that camera 1658 may capture an image using the received light. In some embodiments, dichroic 1654 may be configured to transmit white light and fluorescent light and to reflect excitation light such that the excitation light does not reach camera 1658.

Figure 17:
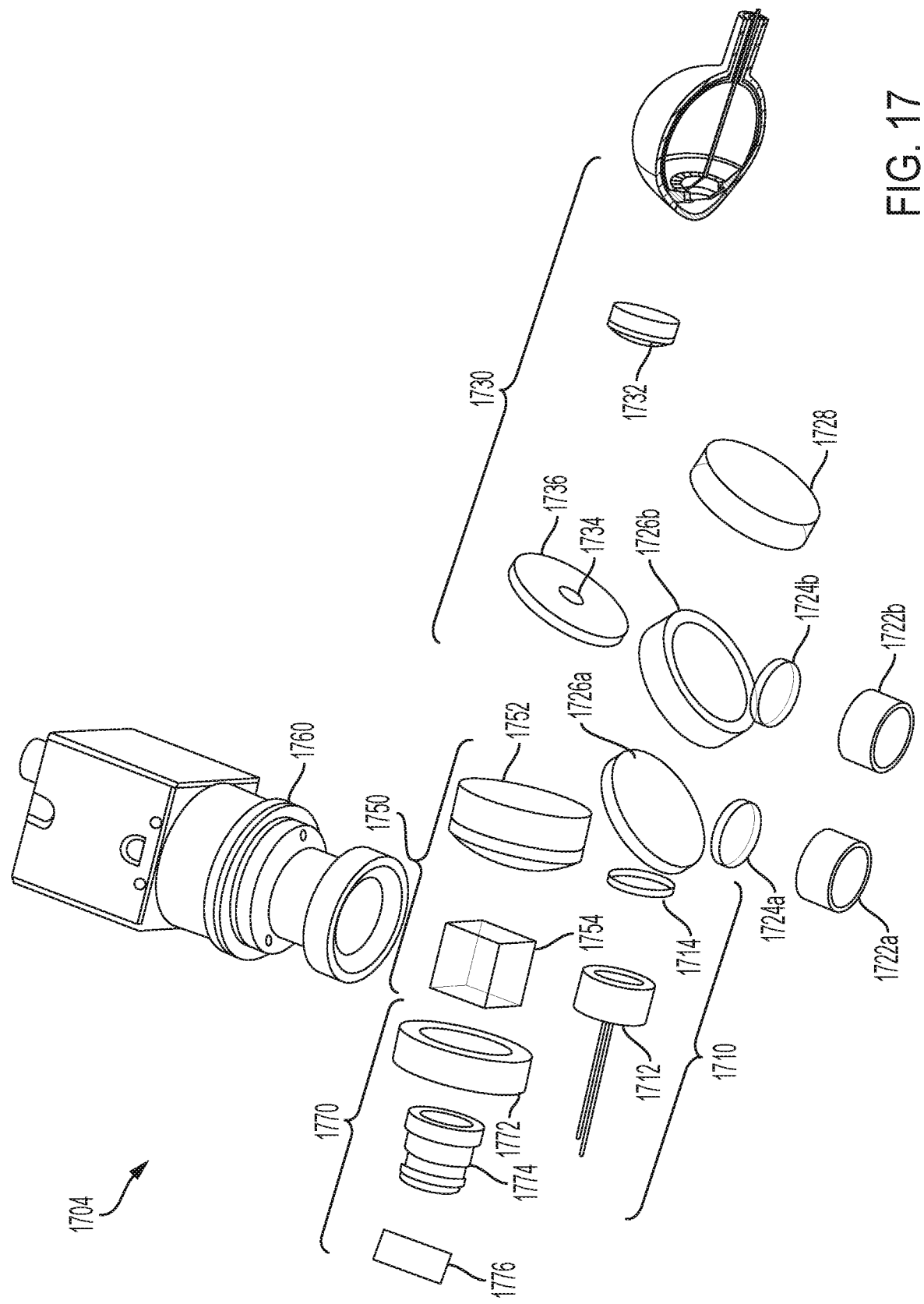
FIG. 17 is a perspective view of alternative white light and fluorescence imaging components that may be included in the imaging apparatus of FIG. 16A, according to some embodiments.

FIG. 17 is a perspective view of alternative fluorescence and white light imaging components 1704 that may be included in an imaging apparatus, according to some embodiments. For instance, in some embodiments, fluorescence and white light imaging components 1704 may be disposed in the first and/or second housing sections of the imaging apparatus, as discussed above. As shown in FIG. 17, fluorescence and white light imaging components 1704 includes white light imaging components, including white light source components 1710 and white light camera 1760, and fluorescence imaging components, including excitation source components and fluorescence detection components 1770. Fluorescence and white light imaging components 1704 further includes sample components 1730 and detection components 1750, which include a shared imaging path for fluorescence and white light imaging. In some embodiments, white light source components 1710 and excitation source components may be configured to provide light to sample components 1730, which may focus the light on a subject's retina fundus. In some embodiments, detection components 1750 may be configured to receive light reflected and/or emitted from the subject's retina fundus and provide received white light to white light camera 1760 and fluorescent light to fluorescence detection components 1770.

In some embodiments, white light source components 1710 may be configured to illuminate the subject's retina fundus such that light reflected and/or scattered by the retina fundus may be captured and imaged by white light camera 1760, as described herein. In FIG. 17, white light source components 1710 include white light source 1712 and collimating lens 1714. In some embodiments, white light source 1712 may include a white LED. In some embodiments, white light source 1712 may include a plurality of color LEDs that combine to substantially cover the visible spectrum, thereby approximating a white light source.

In some embodiments, excitation light source components may be configured to generate light to excite fluorescent molecules in the subject's retina fundus, such that fluorescent light may be captured and imaged by fluorescence detection components 1770. In FIG. 17, excitation light source components include first and second lasers 1722a and 1722b, first and second collimating lenses 1724a and 1724b, and first and second laser dichroics 1726a and 1726b. In some embodiments, first and second lasers 1722a and 1722b may be configured to generate light at wavelengths corresponding to fluorescent characteristics of one or more respective molecules of interest in the subject's retina fundus. In some embodiments, such molecules may be naturally occurring in the retina fundus. In some embodiments, such molecules may be biomarkers configured for fluorescent imaging. In some embodiments, first and second lasers 1722a and 1722b may be configured to generate light at wavelengths that may be combined in a single optical path for imaging the subject's retina fundus. In some embodiments, first laser 1722a may be configured to generate excitation light having a wavelength of 405 nm. In some embodiments, second laser 1722b may be configured to generate excitation light having a wavelength of 450 nm. In some embodiments, first laser 1722a and/or second laser 1722b may be configured to generate light having a bandwidth of 5-6 nm. It should be appreciated that some embodiments may include fewer or more lasers than shown in FIG. 17. In accordance with various embodiments, excitation light source components may include between 3 to 6 lasers configured to generate light at wavelengths of 405 nm, 450 nm, 473 nm, 488 nm, 520 nm, and 633 nm, respectively. In some embodiments, excitation light source components may be configured to provide excitation light suitable for fluorescence intensity measurements. In one example, excitation light source components may include a range of LEDs spanning the visible light spectrum.

As shown in FIG. 17, first laser 1722a is configured to emit excitation light through collimating lens 1724a toward first laser dichroic 1726a. In some embodiments, first laser dichroic 1726a may be configured to transmit light from white light source 1712 and to reflect light from first laser 1722a such that light from first laser 1722a shares an optical path with light from white light source 1712 from first laser dichroic 1726a to second laser dichroic 1726b. In some embodiments, first laser dichroic 1726a may be configured as a long pass filter. Also shown in FIG. 17, second laser 1722b is configured to emit excitation light through collimating lens 1724b toward second laser dichroic 1726b. In some embodiments, second laser dichroic 1726b may be configured to transmit light from white light source 1712 and first laser 1722a and to reflect light from second laser 1722b such that light from second laser 1722b shares an optical path with light from white light source 1712 and first laser 1722a. In some embodiments, second laser dichroic 1726b may be configured as a long pass filter. In FIG. 17, light from white light source 1712, first laser 1722a, and second laser 1722b share an optical path from second laser dichroic 1726b to beam splitter 1754, at which point received fluorescent light and white light are split between fluorescent detection components 1770 and white light camera 1760, respectively.

As shown in FIG. 17, Mirror 1728 is configured to reflect the combined light toward sample components 1730. In some embodiments, mirror 1728 may be a planar mirror. In some embodiments, mirror 1728 may be a spherical mirror configured to adjust size and/or divergence of reflected light.

In some embodiments, sample components 1730 may be configured to focus white and excitation light from white light source components 1710 and excitation source components on the subject's retina fundus. As shown in FIG. 17, sample components 1730 include first achromatic lens 1732 and scattering component 1734. Scattering component 1734 may be configured to reflect light from mirror 1728 toward first achromatic lens 1732. In some embodiments, scattering component 1734 may be a planar mirror. In some embodiments, scattering component 1734 may be a mirror having a scattering surface configured to provide a more uniform illumination of the subject's retina fundus than a planar mirror. In some embodiments, scattering component 1734 may have a 1200 grit scattering surface. According to various embodiments, scattering component 1734 may have a scattering surface of 800 grit, 1000 grit, 1400 grit, or 1600 grit.

As shown in FIG. 17, scattering component 1734 includes hole 1736 configured to allow some light to pass through scattering component 1734. In some embodiments, light received via second laser dichroic 1726b that passes through hole 1736 may not be used for imaging. In some embodiments, hole 1736 may be configured to allow scattered light received from the subject's retina fundus to pass through scattering component 1734 toward white light camera 1760 and fluorescence detection components 1770. In some embodiments, hole 1736 may be cylindrically shaped. In some embodiments, hole 1736 may be configured to prevent noise light from reaching white light camera 1760 and fluorescence detection components 1770. For example, hole 1736 may be configured to block light incident on scattering component 1734 from directions other than the direction(s) in which light is received from the subject's retina fundus from reaching white light camera 1760 and fluorescence detection components 1770. In some embodiments, at least a portion of an interior wall of hole 1736 may include an black material configured to reduce reflections. In some embodiments, the black material may be black tape. In some embodiments, hole 1736 may be shaped to reduce reflections. For example, in some embodiments, hole 1736 may have a conical shape.

First achromatic lens 1732 may be configured to focus light received via scattering component 1734 on the subject's retina fundus. In some embodiments, first achromatic lens 1732 may be configured to collimate light received from the subject's retina fundus. In some embodiments, first achromatic lens 1732 may be positioned at a distance from the retina fundus that results in the received light being nearly collimated. In one example, the focal length of first achromatic lens 1732 may be 20 mm, and a distance from first achromatic lens 1732 to the front of the subject's eye may be 37 mm.

In some embodiments, excitation source components may be configured to cause fluorescence in the subject's retina fundus when light is focused on the retina fundus by sample components 1730. In some embodiments, the fluorescence may cause the subject's retina fundus to emit light at a different wavelength than the excitation light wavelength(s). For example, depending on the molecule of interest that may be excited by the excitation light and respond by emitting fluorescence light, the fluorescence light may have a wavelength that is 30-50 nm, 50-70 nm, or 70-80 nm longer than the excitation light wavelength(s). In some embodiments, sample components 1730 may be configured to receive both the excitation light and the fluorescence light from the subject's retina fundus and provide the received light to detection components 1750.

In some embodiments, detection components 1750 may be configured to receive light from sample components 1730 and provide received white light to white light camera 1760 and fluorescent light to fluorescence detection components 1770. As shown in FIG. 17, detection components 1750 include second achromatic lens 1752 and beam splitter 1754. In some embodiments, second achromatic lens 1752 may be configured to further collimate light received from the subject's retina fundus via sample components 1730. In some embodiments, received light may have a larger spread at second achromatic lens 1752 than at first achromatic lens 1732. Accordingly, in some embodiments, second achromatic lens 1752 may have a larger diameter than first achromatic lens 1732. In one example, first achromatic lens 1732 may have a half-inch diameter, and second achromatic lens 1752 may have a one-inch diameter.

In some embodiments, beam splitter 1754 may be configured to reflect some of the received light to white light camera 1760 and transmit some of the received light to fluorescent detection components 1770. In some embodiments, the beam splitter 1754 may be configured to reflect half of the received light to white light camera 1760 and to transmit half of the received light to fluorescence detection components 1770. In some embodiments, light levels may be lower in fluorescence detection components 1770 than in white light camera 1760. Accordingly, in some embodiments, beam splitter 1754 may be configured to transmit more of the received light to fluorescence detection components 1770 than is reflected to white light camera 1760. In some embodiments, beam splitter 1754 may be configured to transmit 90%, 95%, 99% or 99.9% of the light to the fluorescence detection components 1770 and to reflect 10%, 5%, 1%, or 0.1% of the light to white light camera 1760. As shown in FIG. 17, beam splitter 1754 separates the optical paths for fluorescence and white light imaging.

In some embodiments, white light camera 1760 may be configured to detect light reflected from beam splitter 1754 and store the image data for analysis. In some embodiments, white light camera 1760 may be a high resolution color digital camera. In some embodiments, white light camera 1760 may have a resolution between 3-10 Megapixels. In some embodiments, white light camera 1760 may be a high resolution monochrome digital camera. In some embodiments, white light source 1712 may include a plurality of color LEDs, and white light camera 1760 may be configured to capture a color image of the subject's retina fundus. In one example, light source 1712 includes a red LED, a blue LED, and a green LED, each LED being configured to emit light in a sequence over time, and white light camera 1860 may be configured to capture separate images for each emission of the sequence. White light camera 1760 and/or processing circuitry coupled to white light camera 1760 may be configured to combine the images captured for each emission of the sequence to create a color image of the retina fundus.

In some embodiments, fluorescence detection components 1770 may be configured to detect fluorescent light transmitted via beam splitter 1754 and capture fluorescence information from the light. As shown in FIG. 17, fluorescence detection components 1770 include spectral filter 1772, field lenses 1774, and fluorescence sensor 1776. In some embodiments, spectral filter 1772 may be configured to block the excitation light and transmit fluorescence light. In one example, spectral filter 1772 may be configured to block light having wavelengths of 405 nm and 450 nm. In some embodiments, field lenses 1774 may be configured to focus received light on fluorescence sensor 1776.

In some embodiments, fluorescence sensor 1776 may be configured to distinguish between fluorescent emissions from at least two different molecules. In some embodiments, fluorescence sensor 1776 may be configured to distinguish between molecules whose fluorescent emissions have different lifetimes. For example, in some embodiments, fluorescence sensor 1776 may be configured to determine the location of the different molecules in the subject's retina fundus by determining the lifetime of the received light. In some embodiments, fluorescence sensor 1776 may be configured to distinguish between molecules whose fluorescent emissions have different wavelengths. For example, in some embodiments, fluorescence sensor 1776 may be configured to determine the location of different molecules in the retina fundus by determining the lifetime of the received light. In some embodiments, fluorescence sensor 1776 may be configured to distinguish between molecules whose fluorescent emissions have different intensities. For example, in some embodiments, fluorescence sensor 1776 may be configured to determine the location of different molecules in the retina fundus by determining the intensity of the received light. It should be appreciated that, according to various embodiments, fluorescence sensor 1776 may be configured for lifetime, spectral, intensity, and/or other measurements alone or in combination.

Figure 18:
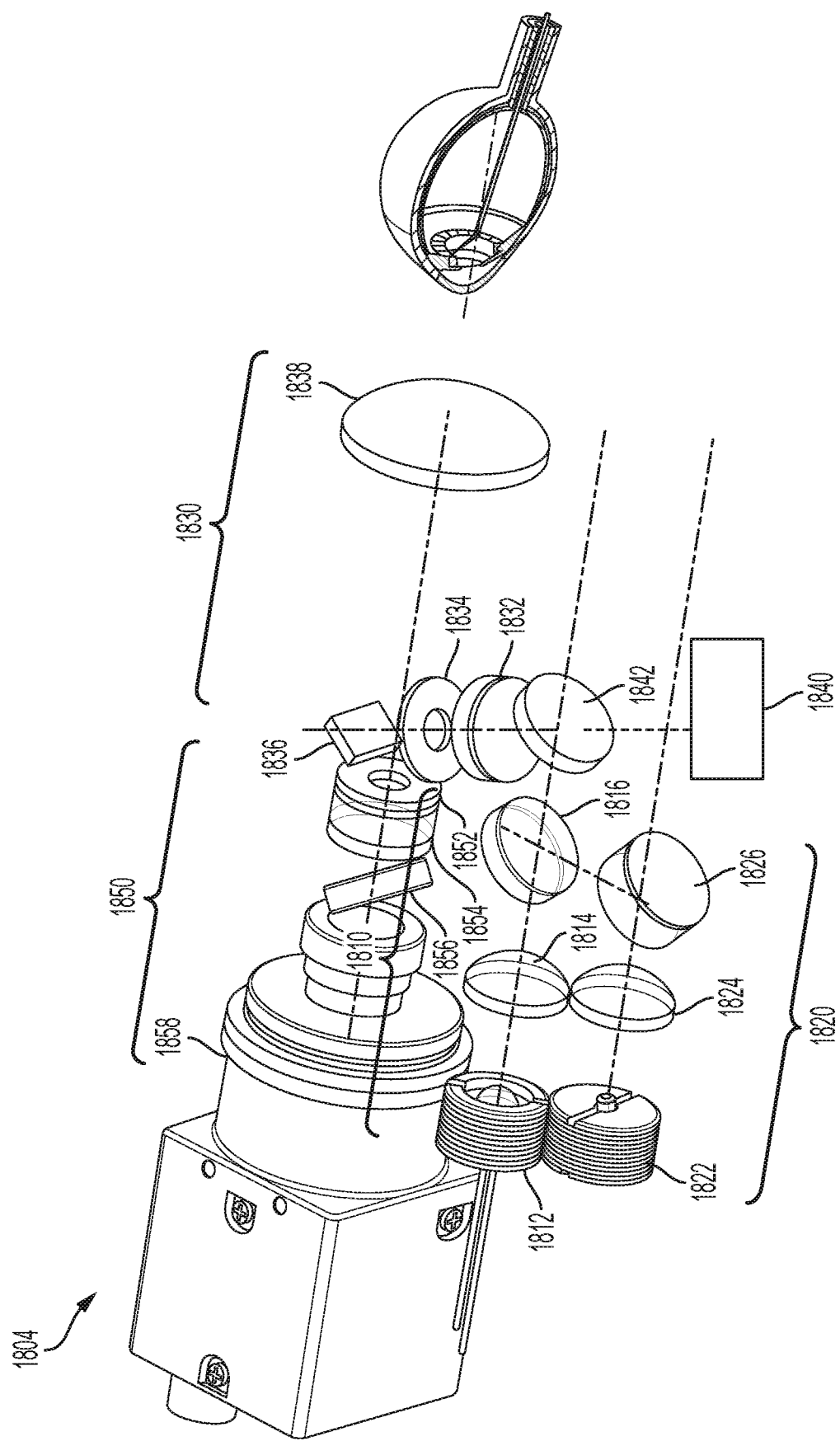
FIG. 18 is a perspective view of further alternative white light and fluorescence imaging components that may be included in the imaging apparatus of FIG. 16A, according to some embodiments.

FIG. 18 is a perspective view of further alternative fluorescence and white light imaging components 1804 that may be included in an imaging apparatus, according to some embodiments. As shown in FIG. 18, fluorescence and white light imaging components 1804 include white light source components 1810, excitation source components 1820, sample components 1830, and detection components 1850. In some embodiments, white light source components 1810 and excitation source components 1820 may be configured to provide light to sample components 1830 for imaging a subject's retina fundus. In some embodiments, sample components 1830 may be configured to focus the light on the subject's retina fundus and receive light reflected and/or emitted by the subject's retina fundus in response. In some embodiments, detection components 1850 may be configured to capture images using light received via sample components 1830. In contrast, to fluorescence and white light components 1704, which include white light camera 1760 and fluorescence detection components 1770, detection components 1850 include combination white light and fluorescence sensor 1858. Moreover, in contrast to excitation source components, which include first and second lasers 1722a and 1722b, excitation source components 1820 are shown in FIG. 18 including single laser 1822. In the embodiment illustrated in FIG. 18, white light and fluorescence sensor 1858 is configured to distinguish between molecules having different fluorescence emission wavelengths. Fluorescence and white light imaging components 1804 further include fixation display 1840, which is configured to provide a fixation object for the subject to visually focus on during imaging.

In some embodiments, white light source components 1810 may be configured to provide white light for transmitting to the subject's retina fundus. As shown in FIG. 18, white light source components 1820 include white light source 1812 and collimating lens 1814, which may be configured in the manner described for white light source 1712 and collimating lens 1714 in connection with FIG. 17.

In some embodiments, excitation light source components 1820 may be configured to provide excitation light for exciting fluorescence emissions from one or more molecules of interest in the subject's retina fundus. As shown in FIG. 18, excitation light source components 1820 include laser 1822, collimating lens 1824, mirror 1826, and laser dichroic 1816. In some embodiments, laser 1822 may be configured in the manner described for first and/or second laser 1722a and/or 1722b, collimating lens 1824 may be configured in the manner described for first and/or second collimating lenses 1724a and/or 1724b, and laser dichroic 1816 may be configured in the manner described for first and/or second laser dichroic 1726a and/or 1726b. Mirror 1826 may be configured to reflect light from laser 1822 to laser dichroic 1816. As shown in FIG. 18, excitation and white light share an optical path from laser dichroic 1816 to white light and fluorescence sensor 1858.

In some embodiments, fixation display 1840 may be configured to provide a fixation object for the subject to focus on during imaging such that the subject's eyes are oriented in desirable direction for imaging. For example, in some embodiments, fixation display 1840 may be configured to display a dot or a house as a fixation object. As shown in FIG. 18, fixation display is configured to provide fixation light to fixation dichroic 1842. In some embodiments, fixation dichroic 1842 may be configured to reflect white and excitation light and to transmit fixation light, such that the white, excitation, and fixation light are combined for transmitting to the subject's retina fundus via sample components 1830.

In some embodiments, sample components 1830 may be configured to provide the white, excitation, and fixation light to the subject's retina fundus. As shown in FIG. 18, sample components 1830 include first achromatic lens 1832, iris 1834, injection mirror 1836, and second achromatic lens 1838. In some embodiments, second achromatic lens 1838 is configured to receive reflected and/or emitted light from the subject's retina fundus and to collimate the received light for transmitting to detection components 1850.

In some embodiments, detection components 1850 may be configured to capture images using light received from the subject's retina fundus. As shown in FIG. 18, detection components 1850 include iris 1852, focusing lens 1854, dichroic 1856, and white light and fluorescence sensor 1858. In some embodiments, iris 1852 may be configured to block light received from directions other than the direction(s) in which light is received from the subject's retina fundus from reaching white light and fluorescence sensor 1858. In some embodiments, focusing lens 1854 may be configured to focus light received from the subject's retina fundus on white light and fluorescence sensor 1858. In some embodiments, dichroic 1856 may be configured to block reflected excitation light from reaching white light and fluorescence sensor 1858. In some embodiments, dichroic 1856 may be configured as a long pass filter.

Figure 19:
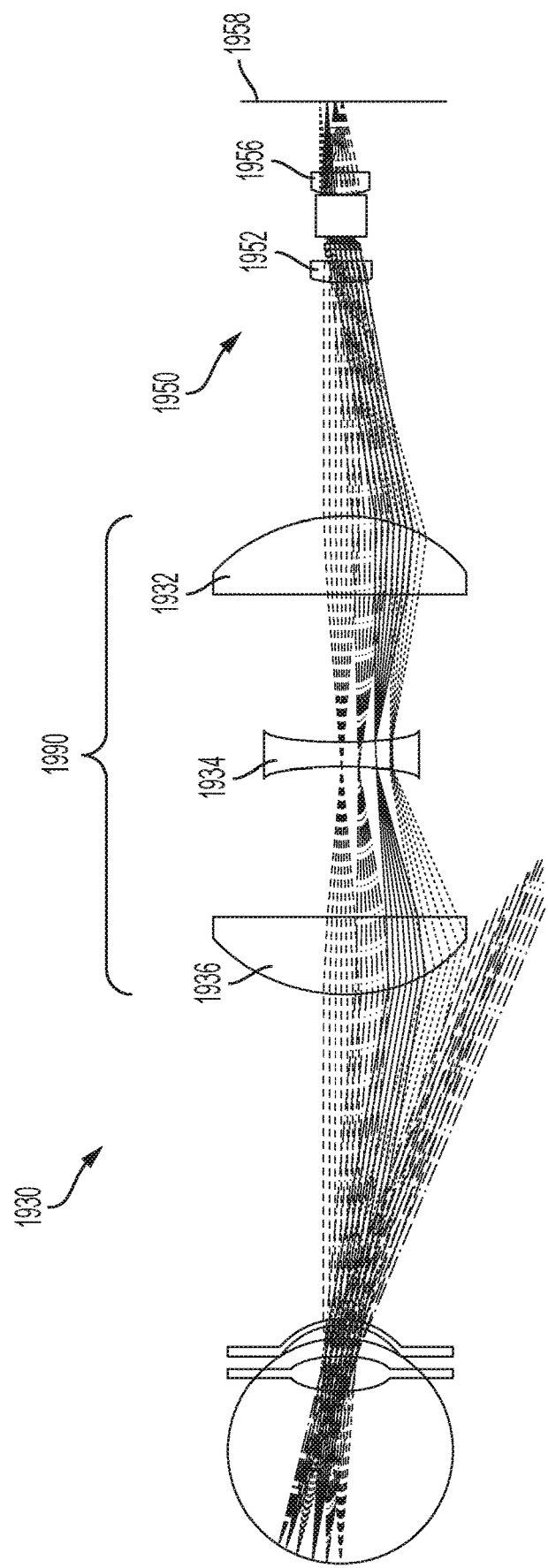
FIG. 19 is a side view of alternative sample and detection components that may be included in the white light and fluorescence imaging components of FIG. 17 or 18, according to some embodiments.

FIG. 19 is a side view of alternative sample components 1930 and detection components 1950 that may be included in combination with other white light and/or fluorescence imaging components of a multi-modal imaging apparatus, according to some embodiments. As shown in FIG. 19, sample components 1930 include pupil relay lenses 1990, which include plano-convex lenses 1932 and 1936 and bi-concave lens 1934. In some embodiments, bi-concave lens 1934 may be configured to provide negative dispersion and/or field flattening. In some embodiments, bi-concave lens 1934 may be configured to provide a negative focal length. In some embodiments, sample components 1930 may further include other sample components such as described herein in connection with FIGS. 17-18. According to various embodiments, sample components 1930 may be configured to illuminate the subject's retina fundus from an on-axis or off-axis illumination ring.

Also shown in FIG. 19, detection components 1950 include achromatic lenses 1952 and 1956 and camera 1958. In some embodiments, achromatic lenses 1952 and 1956 may be configured to flatten the illuminated field, adjust the chief ray angle, and achieve diverging chief rays. In some embodiments, camera 1958 may be a white light and/or fluorescence imaging sensor. In some embodiments, pupil relay lenses 1990 may be adjusted to correct for field curvature of camera 1958. For example, as shown in FIG. 19, pupil relay lenses 1990 are configured to spatially distribute light of different wavelengths at different angles. As shown, achromatic lenses 1952 and 1956 are configured to focus the light of different wavelengths on different respective portions of camera 1958.

IV. Applications

The inventors have developed improved imaging techniques that may be implemented using imaging apparatuses described herein. According to various embodiments, such imaging techniques may be used for biometric identification, health status determination, and disease diagnosis, and others.

The inventors have recognized that various health conditions may be indicated by the appearance of a person's retina fundus in one or more images captured according to techniques described herein. For example, diabetic retinopathy may be indicated by tiny bulges or micro-aneurysms protruding from the vessel walls of the smaller blood vessels, sometimes leaking fluid and blood into the retina. In addition, larger retinal vessels can begin to dilate and become irregular in diameter. Nerve fibers in the retina may begin to swell. Sometimes, the central part of the retina (macula) begins to swell, such as macular edema. Damaged blood vessels may close off, causing the growth of new, abnormal blood vessels in the retina. Glaucomatous optic neuropathy, or Glaucoma, may be indicated by thinning of the parapapillary retinal nerve fiber layer (RNFL) and optic disc cupping as a result of axonal and secondary retinal ganglion cell loss. The inventors have recognized that RNFL defects, for example indicated by OCT, are one of the earliest signs of glaucoma. In addition, age-related macular degeneration (AMD) may be indicated by the macula peeling and/or lifting, disturbances of macular pigmentation such as yellowish material under the pigment epithelial layer in the central retinal zone, and/or drusen such as macular drusen, peripheral drusen, and/or granular pattern drusen. AMD may also be indicated by geographic atrophy, such as a sharply delineated round area of hyperpigmentation, nummular atrophy, and/or subretinal fluid. Stargardt's disease may be indicated by death of photoreceptor cells in the central portion of the retina. Macular edema may be indicated by a trench in an area surrounding the fovea. A macular hole may be indicated by a hole in the macula. Eye floaters may be indicated by non-focused optical path obscuring. Retinal detachment may be indicated by severe optic disc disruption, and/or separation from the underlying pigment epithelium. Retinal degeneration may be indicated by the deterioration of the retina. Central serous retinopathy (CSR) may be indicated by an elevation of sensory retina in the macula, and/or localized detachment from the pigment epithelium. Choroidal melanoma may be indicated by a malignant tumor derived from pigment cells initiated in the choroid. Cataracts may be indicated by opaque lens, and may also cause blurring fluorescence lifetimes and/or 2D retina fundus images. Macular telangiectasia may be indicated by a ring of fluorescence lifetimes increasing dramatically for the macula, and by smaller blood vessels degrading in and around the fovea. Alzheimer's disease and Parkinson's disease may be indicated by thinning of the RNFL. It should be appreciated that diabetic retinopathy, glaucoma, and other such conditions may lead to blindness or severe visual impairment if not properly screened and treated.

Accordingly, in some embodiments, a person's predisposition to various medical conditions may be determined based on one or more images of the person's retina fundus captured according to techniques described herein. For example, if one or more of the above described signs of a particular medical condition (e.g., macula peeling and/or lifting for age-related macular degeneration) is detected in the captured image(s), the person may be predisposed to that medical condition.

The inventors have also recognized that some health conditions may be detected using fluorescence imaging techniques described herein. For example, macular holes may be detected using an excitation light wavelength between 340-500 nm to excite retinal pigment epithelium (RPE) and/or macular pigment in the subject's eye having a fluorescence emission wavelength of 540 nm and/or between 430-460 nm. Fluorescence from RPE may be primarily due to lipofuscin from RPE lysomes. Retinal artery occlusion may be detected using an excitation light wavelength of 445 nm to excite Flavin adenine dinucleotides (FAD), RPE, and/or nicotinamide adenine dinucleotide (NADH) in the subject's eye having a fluorescence emission wavelength between 520-570 nm. AMD in the drusen may be detected using an excitation light wavelength between 340-500 nm to excite RPE in the subject's eye having a fluorescence emission wavelength of 540 nm and/or between 430-460 nm. AMD including geographic atrophy may be detected using an excitation light wavelength of 445 nm to excite RPE and elastin in the subject's eye having a fluorescence emission wavelength between 520-570 nm. AMD of the neovascular variety may be detected by exciting the subject's choroid and/or inner retina layers. Diabetic retinopathy may be detected using an excitation light wavelength of 448 nm to excite FAD in the subject's eye having a fluorescence emission wavelength between 590-560 nm. Central serous chorio-retinopathy (CSCR) may be detected using an excitation light wavelength of 445 nm to excite RPE and elastin in the subject's eye having a fluorescence emission wavelength between 520-570 nm. Stargardt disease may be detected using an excitation light wavelength between 340-500 nm to excite RPE in the subject's eye having a fluorescence emission wavelength of 540 nm and/or between 430-460 nm. Choroideremia may be detected using an excitation light wavelength between 340-500 nm to excite RPE in the subject's eye having a fluorescence emission wavelength of 540 nm and/or between 430-460 nm.

The inventors have also developed techniques for using a captured image of a person's retina fundus to diagnose various health issues of the person. For example, in some embodiments, any of the health conditions described above may be diagnosed.

In some embodiments, imaging techniques described herein may be used for health status determination, which may include determinations relating to cardiac health, cardiovascular disease, anemia, retinal toxicity, body mass index, water weight, hydration status, muscle mass, age, smoking habits, blood oxygen levels, heart rate, white blood cell counts, red blood cell counts, and/or other such health attributes. For example, in some embodiments, a light source having a bandwidth of at least 40 nm may be configured with sufficient imaging resolution capturing red blood cells having a diameter of 6 μm and white blood cells having diameters of at least 15 μm. Accordingly, imaging techniques described herein may be configured to facilitate sorting and counting of red and white blood cells, estimating the density of each within the blood, and/or other such determinations.

In some embodiments, imaging techniques described herein may facilitate tracking of the movement of blood cells to measure blood flow rates. In some embodiments, imaging techniques described herein may facilitate tracking the width of the blood vessels, which can provide an estimate of blood pressure changes and profusion. For example, an imaging apparatus as described herein configured to resolve red and white blood cells using a 3-dimensional (3D) spatial scan completed within 1 μs may be configured to capture movement of blood cells at 1 meter per second. In some embodiments, light sources that may be included in apparatuses described herein, such as superluminescent diodes, LEDs, and/or lasers, may be configured to emit sub-microsecond light pulses such that an image may be captured in less than one microsecond. Using spectral line scan techniques described herein, an entire cross section of a scanned line versus depth can be captured in a submicrosecond. In some embodiments, a 2-dimensional (2D) sensor described herein may be configured to capture such images for internal or external reading at a slow rate and subsequent analysis. In some embodiments, a 3D sensor may be used. Embodiments described below overcome the challenges of obtaining multiple high quality scans within a single microsecond.

In some embodiments, imaging apparatuses described herein may be configured to scan a line aligned along a blood vessel direction. For example, the scan line may be rotated and positioned after identifying a blood vessel configuration of the subject's retina fundus and selecting a larger vessel for observation. In some embodiments, a blood vessel that is small and only allows one cell to transit the vessel in sequence may be selected such that the selected vessel fits within a single scan line. In some embodiments, limiting the target imaging area to a smaller section of the subject's eye may reduce the collection area for the imaging sensor. In some embodiments, using a portion of the imaging sensor facilitates increasing the imaging frame rate to 10 s of KHz. In some embodiments, imaging apparatuses described herein may be configured to perform a fast scan over a small area of the subject's eye while reducing spectral spread interference. For example, each scanned line may use a different 2D section of the imaging sensor array. Accordingly, multiple line scans may be captured at the same time, where each line scan is captured by a respective portion of the imaging sensor array. In some embodiments, each line scan may be magnified to result in wider spacing on the imaging sensor array, such as wider than the dispersed spectrum, so that each 2D line scan may be measured independently.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The acts performed as part of the methods may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. An apparatus for imaging and/or measuring a retina fundus of a subject, the apparatus comprising:
   a housing;
   a white light imaging device supported by the housing; and
   a fluorescence imaging device supported by the housing, the fluorescence imaging device comprising a fluorescence imaging sensor configured to detect a fluorescence wavelength of at least one molecule in the subject's eye,
   wherein the white light imaging device and the fluorescence imaging device share at least a portion of a shared optical path within the housing.

2. The apparatus of claim 1, wherein the white light imaging device and the fluorescence imaging device share an imaging sensor.

3. The apparatus of claim 2, wherein:
   the white light imaging device comprises a white light source;
   the fluorescence imaging device comprises at least one laser; and
   the apparatus further comprises an optical element configured to combine an optical path of light emitted from the white light source with an optical path of light emitted from the at least one laser such that the light emitted from the white light source and the light emitted from the at least one laser share the shared optical path.

4. The apparatus of claim 3, wherein:
   the fluorescence imaging device comprises a first laser configured to emit light at a first wavelength and a second laser configured to emit light at a second wavelength; and
   the apparatus comprises:
      a first optical element configured to combine the optical path of light emitted from the white light source with an optical path of light emitted from the first laser; and
      a second optical element configured to combine the optical path of the light emitted from the white light source and the optical path of the light emitted from the first laser with an optical path of light emitted from the second laser, such that the light emitted from the white light source, the light emitted from the first laser, and the light emitted from the second laser share the shared optical path.

5. The apparatus of claim 3, wherein the shared optical path includes a path from the first optical element to an eye of the subject, and from the eye of the subject to the imaging sensor.

6. The apparatus of claim 1, further comprising a scattering component in the shared optical path, the scattering component comprising an opening configured to allow light reflected from the retina fundus to pass through the scattering component.

7. The apparatus of claim 1, further comprising a beam splitter configured to transmit light for the fluorescence imaging device to the fluorescence imaging sensor and reflect light for the white light imaging device to a white light image sensor.

8. The apparatus of claim 7, wherein a transmissivity of the beam splitter is greater than a reflectivity of the beam splitter.

9. The apparatus of claim 8, wherein the fluorescence imaging sensor is configured to detect a fluorescence lifetime of at least one molecule in the subject's eye.

10. A method comprising:
imaging a retina fundus of a subject with a white light imaging device and a fluorescence imaging device which share, at least in part, an optical path, wherein the imaging includes imaging the retina fundus with a fluorescence imaging sensor of the fluorescence imaging device, the fluorescence imaging sensor configured to detect a fluorescence wavelength of at least one molecule in the subject's eye.

11. A method comprising:
imaging and/or measuring a retina fundus of a subject using an apparatus comprising at least two imaging and/or measuring devices selected from a group comprising:
a white light imaging device;
a fluorescence imaging device comprising a fluorescence imaging sensor configured to detect a fluorescence wavelength of at least one molecule in the subject's eye; and
an optical coherence tomography device; and
determining a medical status of the subject based on an image captured during imaging and/or measuring.

12. The method of claim 11, wherein determining the medical status comprises determining whether the subject suffers from an ocular disease.

13. The method of claim 12, wherein the ocular disease comprises age-related macular degeneration (AMD).

14. The method of claim 12, wherein the ocular disease comprises Stargardt's disease.

15. The method of claim 12, wherein the ocular disease comprises diabetic retinopathy.

16. The method of claim 12, wherein the ocular disease comprises macular edema.

17. The method of claim 12, wherein the ocular disease comprises a macular hole.

18. The method of claim 12, wherein the ocular disease comprises eye floaters.

19. The method of claim 12, wherein the ocular disease comprises glaucoma.

20. The method of claim 12, wherein the ocular disease comprises retinal detachment.

21. The method of claim 12, wherein the ocular disease comprises cataracts.

22. The method of claim 12, wherein the ocular disease comprises macular telangiectasia.

23. The method of claim 11, wherein determining the medical status comprises determining whether the subject suffers from a non-ocular disease.

24. The method of claim 23, wherein the non-ocular disease comprises Alzheimer's.

25. The method of claim 24, wherein determining whether the subject suffers from Alzheimer's comprises determining a thickness of a retinal nerve fiber layer of the subject using the image.

26. The method of claim 23, wherein the non-ocular disease comprises Parkinson's.

27. The method of claim 26, wherein determining whether the subject suffers from Parkinson's comprises determining a thickness of a retinal nerve fiber layer of the subject using the image.

28. The method of claim 26, wherein determining whether the subject suffers from Parkinson's comprises determining a measure of eye-tracking capability using the image.

29. The method of claim 23, wherein the non-ocular disease comprises a concussion.

\* \* \* \* \*